United States Patent
Marazzi

(10) Patent No.: US 11,173,154 B2
(45) Date of Patent: Nov. 16, 2021

(54) METHODS OF TREATING EXACERBATED INFLAMMATORY RESPONSE WITH TOPOISOMERASE I INHIBITORS

(71) Applicant: ICAHN SCHOOL OF MEDICINE AT MOUNT SINAI, New York, NY (US)

(72) Inventor: Ivan Marazzi, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 523 days.

(21) Appl. No.: 16/063,009

(22) PCT Filed: Dec. 15, 2016

(86) PCT No.: PCT/US2016/066873
§ 371 (c)(1),
(2) Date: Jun. 15, 2018

(87) PCT Pub. No.: WO2017/106466
PCT Pub. Date: Jun. 22, 2017

(65) Prior Publication Data
US 2020/0222385 A1 Jul. 16, 2020

Related U.S. Application Data

(60) Provisional application No. 62/267,608, filed on Dec. 15, 2015.

(51) Int. Cl.
| | | |
|---|---|---|
| *A61K 31/4745* | (2006.01) | |
| *A61K 31/05* | (2006.01) | |
| *A61K 31/473* | (2006.01) | |
| *A61K 38/00* | (2006.01) | |
| *A61K 45/06* | (2006.01) | |

(52) U.S. Cl.
CPC .......... *A61K 31/4745* (2013.01); *A61K 31/05* (2013.01); *A61K 31/473* (2013.01); *A61K 38/005* (2013.01); *A61K 45/06* (2013.01)

(58) Field of Classification Search
CPC .... A61K 31/05; A61K 31/453; A61K 31/473; A61K 31/4745; A61K 31/551; A61K 38/005; A61K 38/00; A61K 45/06
See application file for complete search history.

(56) References Cited

U.S. PATENT DOCUMENTS

| | | | | |
|---|---|---|---|---|
| 5,622,959 A | * | 4/1997 | Priel | A61K 31/00 514/283 |
| 9,345,768 B2 | * | 5/2016 | Jordan | A61K 9/1676 |
| 2003/0139353 A1 | | 7/2003 | Jackson et al. | |
| 2004/0228876 A1 | * | 11/2004 | Nishiyama | A61P 43/00 424/199.1 |

FOREIGN PATENT DOCUMENTS

| | | |
|---|---|---|
| CN | 103864810 A | 6/2014 |
| EP | 2457572 A1 | 5/2012 |
| WO | 2011064152 A1 | 6/2011 |
| WO | 2015/011732 A2 | 1/2015 |

OTHER PUBLICATIONS

Cortes et al. (Expert Opinion, Ther. Patents (2007), 17(5):521-532) (Year: 2007).*
O'Brien et al. (The Am J of Medicine, 2007, 120, 1012-1022). (Year: 2007).*
European Search Report issued in EP Application No. 16876662.4 dated Oct. 22, 2019.
International Search Report and Written Opinion dated Apr. 10, 2017, issue by the International Searching Authority.
Pommier et al., The indenoisoquinoline noncamptothecin topoisomerase I inhibitors: update and perspectives. Mol Cancer Ther. (May 2009) vol. 8, No. 5, pp. 1008-1014 abstract.
Jackson et al., Topoisomerase inhibitors as anti-arthritic agents. Inflamm Res. (Mar. 2008) vol. 57, No. 3, pp. 120-134, abstract, p. 127 col. 1 para 2.
Rialdi et al., Topoisomerase 1 inhibition suppresses inflammatory genes and protects from death by inflammation. Science. (May 27, 2016) vol. 352, No. 6289 and 7993, entire document.
International Preliminary Report on Patentability and Written Opinion dated Jun. 19, 2018 by the International Searching Authority for International Application No. PCT/US2016/066873.
Supplementary Partial European Search Report dated Jul. 18, 2019 for EP Patent Application No. 16876662.4.
Seo et al., "Protective Effect of Lignans against Sepsis from the Roots of Saururus chinensis", Biol. Pharm. Bull, vol. 31, No. 3, pp. 523-526, 2008.
Lee et al., "Inhibition of DNA Topoisomerases I and II and Cytotoxicity by Lignans from Saururus chinensis", Archives of Pharmacal Research, vol. 32, No. 10, pp. 1409-1415, 2009.

(Continued)

*Primary Examiner* — Umamaheswari Ramachandran
(74) *Attorney, Agent, or Firm* — Troutman Pepper Hamilton Sanders LLP

(57) ABSTRACT

A method of treating a disease, condition or state characterized by an exacerbated immune response is disclosed. The method of treatment can include topoisomerase I inhibitors and pharmaceutical compositions comprising topoisomerase I inhibitors, which can be administered alone or in combination with another therapeutic agent. The method can be used to treat a range of diseases, disorders, conditions and states, including but not limited to sepsis, acute liver failure, and endotoxic and/or exotoxic shock. These diseases, disorders, conditions and states can be caused by a variety of microorganisms and/or portions of microorganisms including but not limited to Ebola virus, Lassa virus, Influenza virus, *Legionella*, lipopolysaccharide (LPS), and bacterial endotoxins/exotoxins.

7 Claims, 42 Drawing Sheets
Specification includes a Sequence Listing.

(56) References Cited

OTHER PUBLICATIONS

Van der Poll et al., "The immunopathology of sepsis and potential therapeutic targets", Nature Reviews, 2017, vol. 17, pp. 407-420.
Fajgenbaum et al., "Cytokine Storm", The New England Journal of Medicine, 2020, vol. 383, No. 23, pp. 2255-2273.
Kaukonen et al., "Systemic Inflammatory Response Syndrome Criteria in Defining Severe Sepsis", The New England Journal of Medicine, 2015, vol. 372, No. 17, pp. 1629-1638.
Pommier, "Topoisomerase I inhibitors: camptothecins and beyond", Nature Reviews, 2006, vol. 6, pp. 789-802.

\* cited by examiner

FIG. 3F

SEQUENCE LISTING

<160> NUMBER OF SEQ ID NOS: 66

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
accttctaca atgagctgcg                                                   20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cctggatagc aacgtacatg g                                                 21

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcaaattcca tggcaccgt                                                    19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

```
gccccacttg attttggagg                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtaacccgtt gaaccccatt                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccatccaatc ggtagtagcg                                               20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aggctttgca tgtcttgg                                                 18

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gagtcttcat ctgcttgttg c                                             21

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ttcggagaaa ggcattaga                                                19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tccagggctt cattcatat                                                19
```

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tctggcacaa caggtagtag gc                                                22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gagaagcaca acaggagagc aa                                                22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gaaaaggacc ccacgaagtg t                                                 21

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agtcaagggc atatcctaca aca                                               23

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gagctaccca cagaagaaac c                                                 21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gagtcgatgc ttgagttgtg tt                                                22

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
atgatggctt attacagtgg caa                                           23

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gtcggagatt cgtagctgga                                               20

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
actcacctct tcagaacgaa ttg                                           23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccatctttgg aaggttcagg ttg                                           23

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttttgccaag gagtgctaaa ga                                            22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aaccctctgc acccagtttt c                                             21

```
<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
atggcaaagc agtacgactc g                                              21

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gcaaggctgt aatggggaac                                                20

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
acaacaaacg gtggtatttc act                                            23

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cctgctggcg ataagaaagt t                                              21

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ttacggatgt caacgtcaca gttc                                           24

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
actattggca acgagcggtt c                                              21

<210> SEQ ID NO 29
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cgagtaccag tcccttttct gttc                                          24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aagacttggt tgcagagtgt catg                                          24

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tgagatctac tcggcaaacc tagtg                                         25

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cttcgtagag aacaacataa gtcagatacc                                    30

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gcctatcgcc aagatttaga tga                                           23

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ttctggattt aaccggacag c                                             21

<210> SEQ ID NO 35
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
agaaccaaaa cgagagagag tgagg                                          25

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tccagacggt agttcgcaat g                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gtccctcaac ggaagaacca a                                              21

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
actctcagac agcgaggcac at                                             22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tgcccacgtc aaggagtatt tc                                             22

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tcctagctca tctccaaata gttgatg                                        27

<210> SEQ ID NO 41
<211> LENGTH: 22
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 41
gcaactgttc ctgaactcaa ct                                              22

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
atcttttggg gtccgtcaac t                                               21

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gaggggagag ggggtaaaa                                                  19

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
agccataaaa ggcaactttc g                                               21

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
agaggagcct ggctaagca                                                  19

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ggttgctgta aattaggcag c                                               21

<210> SEQ ID NO 47
<211> LENGTH: 18
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 47
tgcactgcaa ccatgagg                                                    18

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tgactcaaca gcactaccga                                                  20

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cccaataaat ataggactgg agatg                                            25

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gagttcatag ctgggctcct                                                  20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tataaaaagc caccggagca                                                  20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gccagcttgg aagtcatgtt                                                  20

<210> SEQ ID NO 53
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 53
gggctacagt gggtgaaagg                                                    20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gggctacagt gggtgaaagg                                                    20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tgaaaagagc acaccccta                                                     20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ctcctcagaa acctgccttg                                                    20

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
agccacaccc gactaacg                                                      18

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cttggtgctt tgagggatct                                                    20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 59
aatgtgggat tttcccatga                                                    20

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gcggtttctg gaattgacta tc                                                 22

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gggcttttcc agacatcgt                                                     19

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tgaagtgtgg ctggagtctg                                                    20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gatcggaaga gcacacgtct                                                    20

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
acactctttc cctacacgac gctcttccga tct                                     33

<210> SEQ ID NO 65
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 65
aatgatacgg cgaccaccga gatctacact ctttccctac acgacgctct tccgatct      58

<210> SEQ ID NO 66
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(30)
<223> OTHER INFORMATION: a, c, t, g, unknown or other

<400> SEQUENCE: 66
caagcagaag acggcatacg agatnnnnnn gtgactggag ttcagacgtg tgctcttccg     60
atct                                                                  64
```

METHODS OF TREATING EXACERBATED INFLAMMATORY RESPONSE WITH TOPOISOMERASE I INHIBITORS

CROSS-REFERENCE TO RELATED APPLICATION

This application is a United States National Stage Application of, and claims the benefit pursuant to 35 U.S.C. § 371 of, International Patent Application Serial No. PCT/US2016/066873, filed Dec. 15, 2016, which claims priority to U.S. Provisional Application No. 62/267,608, filed on 15 Dec. 2015, the disclosure of which all is herein incorporated by reference in its entirety.

SEQUENCE LISTING

The instant application contains a Sequence Listing which has been submitted electronically in ASCII format and is hereby incorporated by reference in its entirety. Said ASCII copy, created on Dec. 14, 2016, is named 242096_000030_SL.txt and is 15,983 bytes in size.

STATEMENT AS TO FEDERALLY SPONSORED RESEARCH

The United States Government has certain rights to this invention by virtue of funding reserved from: NIAID-Funded Center of Excellence for Influenza Research and Surveillance Grant No. HHSN272201400008C—Center for Research on Influenza Pathogenesis, Public Health Service Institutional Research Training Award AI07647, Department of Defense Grant No. W911NF-14-1-0353, and National Institute of Health Grant Nos. U19AI106754, 1R01AN3663134 and 1R56AI114770-01A1.

BACKGROUND OF THE INVENTION

1. Field of the Invention

Embodiments of the present invention relate generally to methods of treating exacerbated immune responses caused by various infections, diseases, conditions and/or states, and more specifically to therapies using inhibitors of topoisomerase I (Top1). Provided herein are methods of using Top1 inhibitors to control the transcriptional response to such infections, diseases, conditions and/or states, and thus to protect the subject against infections, diseases, conditions and/or states caused by the exacerbated immune response.

2. Background

The host innate immune response is the first line of defense against pathogens and is orchestrated by the concerted expression of genes induced by microbial stimuli. Deregulated expression of these genes is linked to the initiation and progression of numerous diseases associated with exacerbated inflammation. Top1 has been identified as a critical positive regulator of RNA polymerase II (RNAPII) transcriptional activity at pathogen-induced genes. Notably, depletion or chemical inhibition of Top1 suppresses the host response against replicating Influenza and Ebola viruses as well as bacterial products. As a result, pharmacological inhibition of Top1 protects mice from death in experimental models of septic shock and acute liver failure. Top1 inhibition could therefore be used as therapy against life threatening infections characterized by an exacerbated immune response as it controls the magnitude of the transcriptional response to such infections.

The innate immune response is a key defense mechanism against infections. Activation of innate immune cells relies on the expression of a large family of Pattern Recognition Receptors (PRRs), which detect distinct conserved microbial structures, called Pathogen-Associated Molecular Patterns (PAMPs)(1, 2). The immunological response that follows PRR downstream signaling is then governed by the combinatorial expression of PAMP-response genes(3). While the function of many of the PAW-response genes and their antiviral/inflammatory activity still remains elusive, their expression is essential for the host defense against pathogens(4). Failure in regulating the induction-, and post-induction repression of these anti-microbial genes can alter the balance between pro- and anti-inflammatory states, often leading to detrimental effects for the host(5-7). Indeed, hyper activation of anti-microbial genes has been suggested to be responsible for the high mortality rates during highly pathogenic infections (8, 9). Another well-known example is the syndrome called "septic shock," where the uncontrolled expression of pro-inflammatory genes in response to bacterial PAMPs leads to severe collateral effects, such as local and systemic tissue injury, which can often be lethal to the host(10). In these contexts, pharmacological inhibition of factors that control the magnitude of the innate immune response could be useful for therapy.

Herein it is demonstrated that the enzyme Topoisomerase-1 (Top1) exerts an activating role on the transcriptional response against infection and/or an exacerbated immune response in both cells and at the organismal level. This effect is achieved via Top1-mediated regulation of transcriptional activation of pro-inflammatory genes. It is further shown that chemical inhibition, as well as reduced expression of Top1, limits the overexpression of inflammatory genes characteristic of those induced in cytokine storms, such as infection with influenza and Ebola viruses and bacterial products. Notably, Top1 inhibition rescues the mortality in mouse models of septic shock and acute liver failure caused by overexposure to bacterial PAMPs. These results suggest the therapeutic usage of Top1 inhibitors for treatment of diseases and conditions characterized by exacerbated innate immune responses. Importantly, the regime of Top1 inhibitors used herein are lower than those typically used to treat cancer. The use of lower regime of such inhibitors allows a reversible inhibition of Top1 such that no or minimal DNA damage can result from the treatment, as evidence by the lack of effect of topoisomerase inhibition cell viability This reversible inhibition, as well as other unexpected results of using Top1 inhibitors for inflammatory genes inhibition, are discussed further herein.

What is needed, therefore, is a method of treatment of diseases and conditions characterized by exacerbated immune responses, preferably by means of inhibiting the activity of Top1. Such inhibition may occur by chemical or biological/genetic means. It is to such a method of treatment that embodiments of the present invention are primarily directed.

BRIEF SUMMARY OF THE INVENTION

As specified in the Background Section, there is a great need in the art to identify technologies for treating diseases, disorders, states and conditions characterized by exacerbated immune responses and use this understanding to develop novel therapeutics and methods for the treatment of such diseases, disorders, states and conditions. The present invention satisfies this and other needs. Embodiments of the present invention relate generally to methods of controlling inflammatory gene expression by using Top1 inhibitors to cause reversible inhibition of Top1 while still allowing for control of expression.

In some embodiments of the present invention, a method of treating a disease, condition, disorder or state characterized by an exacerbated immune response comprises administration of a therapeutically effective amount of at least one compound that inhibits Top1 activity. In other embodiments, a method of treating such disease, condition, disorder or state comprises administration of a pharmaceutical composition comprising at least one compound that inhibits Top1 activity and may comprise other pharmaceutically acceptable compounds such as a carrier.

In some embodiments of the present invention, a compound that inhibits Top1 activity comprises chemical and/or biological inhibitors and combinations thereof.

In some embodiments of the present invention, the chemical inhibitor is selected from the group consisting of camptothecin, topotecan, irinotecan, plant-derived phenols, indenoisoquinolines and lamellarin D and derivatives thereof. More than one chemical inhibitor may be utilized in the treatment method. Indenoisoquinolines are preferred in some embodiments.

In other embodiments of the present invention, the biological inhibitor is selected from the group consisting of (i) silencing or interfering nucleic acids specific to and/or capable of binding Top1; (ii) transcriptional regulators of Top1; (iii) translational regulators of Top1; and (iv) post-translational regulators of Top1. Exemplary silencing or interfering nucleic acids include but are not limited to siRNA specific to Top1. Exemplary transcriptional regulators of Top1 include but are not limited to transcription factors, transcription activators, repressors, and/or small molecules affecting transcription and the proteins involved in such process. Exemplary translational and post-translational regulators include but are not limited to regulators that phosphorylate and/or dephosphorylate Top1. More than one biological inhibitor may be utilized in the treatment method. In some embodiments, siRNA is a preferred biological inhibitor.

In some embodiments of the present invention, the at least one compound that inhibits Top1 activity is an aptamer that is capable of binding to the Top1 protein or a nucleic acid encoding Top1. More than one aptamer may be utilized in the treatment method.

In some embodiments of the present invention, the method comprises treating a disease, condition, state and/or disorder selected from the group consisting of sepsis, septic shock, acute liver failure, endotoxic or exotoxic shock, inflammatory bowel disease (IBD), graft-versus host disease (GVHD), ulcerative colitis (UC), Crohn's disease, diabetes (e.g., diabetes mellitus type 1), multiple sclerosis, arthritis (e.g., rheumatoid arthritis), Graves' disease, lupus erythematosus, ankylosing spondylitis, psoriasis, Behcet's disease, autistic enterocolitis, Guillain-Barre Syndrome, myasthenia gravis, pemphigus vulgaris, acute disseminated encephalomyelitis (ADEM), transverse myelitis autoimmune cardiomyopathy, Celiac disease, dermatomyositis, Wegener's granulomatosis, allergy, asthma, contact dermatitis, atherosclerosis (or any other inflammatory condition affecting the heart or vascular system), autoimmune uveitis, as well as other autoimmune skin conditions, autoimmune kidney, lung, or liver conditions and autoimmune neuropathies.

In some embodiments, the disease, condition, state and/or disorder preferably comprises sepsis, septic shock and/or acute liver failure.

In some embodiments, the method comprises treating a disease, condition, infection, state and/or disorder that is characterized by an exacerbated immune response and/or cytokine storm.

In some embodiments, the disease, condition, state and/or disorder may be caused and/or exacerbated by a microorganism or portion of a microorganism. Exemplary microorganisms and portions of microorganisms include but are not limited to Ebola virus, Lassa virus, Influenza virus, *Legionella*, lipopolysaccharide (LPS), and bacterial endotoxins/exotoxins.

In some embodiments, the treatment method comprises the co-administration of at least one other therapeutic agent.

In some embodiments, the co-administered therapeutic agent is selected from the group consisting of (i) therapeutic agents that block inflammation; (ii) one or more anti-tumor antibodies or antibodies directed at a pathogenic antigen or allergen; (iii) other immunomodulatory treatments; (iv) one or more bromodomain inhibitors; and (v) one or more antibiotics, anti-fungal drugs, anti-viral drugs, anti-parasitic drugs, or anti-protozoal drugs, including any combination of the foregoing.

In some embodiments, the therapeutically effective amount of the at least one compound is determined by the disease, condition, infection, state and/or disorder. Certain diseases, conditions, infections, states and/or disorders may require a higher amount of the at least one compound than other such diseases, conditions, infections, states and/or disorders in order to be therapeutically effective. Further, certain microorganisms and/or portions of microorganisms may cause and/or exacerbate, directly or indirectly, diseases, conditions, infections, states and/or disorders with exacerbated immune responses that may require a higher amount of the at least one compound than those caused and/or exacerbated by other microorganisms and/or portions of microorganisms. However, the therapeutically effective regime used in methods of the present invention will likely be shorter than the therapeutically effective Top1 inhibitor regime required to treat cancers and/or tumors, meaning that the duration of administration can be shorter. It is also possible that the therapeutically effective amount of Top1 inhibitor used in methods of the present invention may be lower than the therapeutically effective amounts of Top1 inhibitor used to treat cancers and/or tumors.

Surprising evidence is provided herein demonstrating that during a cytokine storm or exacerbated immune response, short and reversible inhibition of Top1, as well as Top1 depletion, specifically suppresses genes induced by microbial agents. Such short and reversible inhibition results reveal a surprising gene specific activator-like role for Top1. Without wishing to be bound by theory, it is possible that the short and reversible inhibition results from decreased or non-existent cleavage complexes resulting in less DNA damage.

These and other objects, features and advantages of the present invention will become more apparent upon reading the following specification in conjunction with the accompanying drawing figures.

DESCRIPTION OF THE DRAWINGS

FIG. 3A-F shows that Top1 inhibition blocks inflammation-induced death in vivo. (3A, 3B) Gene expression in A549 (3A) or RAW 264.7 (3B) cells, left untreated (−) or treated with 0.5 μM DMSO, CPT or 100 nM TPT, in the presence of LPS stimulation or not (UT). (3C, 3D) Survival curves of C57BL/6J mice left untreated or treated with CPT in response to LPS-induced septic shock (C) or D-GalN/LPS induced acute liver failure (3D). (3E) Serum titers of indicated cytokines 4 hours after LPS injection to induce septic shock (as in (3C)). (3F) THP-1 cells were mock treated or infected with wild-type (WT) Ebola virus (Zaire-Mayinga strain) in the presence of 0.5 μM of DMSO or CPT and 100 nM TPT. Bar graphs show the relative expression of selected genes. *P<0.05, P<0.005 and *P<0.0005, calculated with a student's t-test (3A), (3B), (3E), (3F) or long rank test (3C-3D). Data are from three independent experiments (3A), (3B), (3E) with (3E) n=10 individual mice; four independent trials (3C) n=11 untreated and n=12 CPT-treated individual mice, (3D) n=10 untreated and n=12 CPT-treated individual mice, and two independent experiments (3F). Mean and s.d. are indicated in (3A, 3B) and (3E, 3F).

Figure 8A:
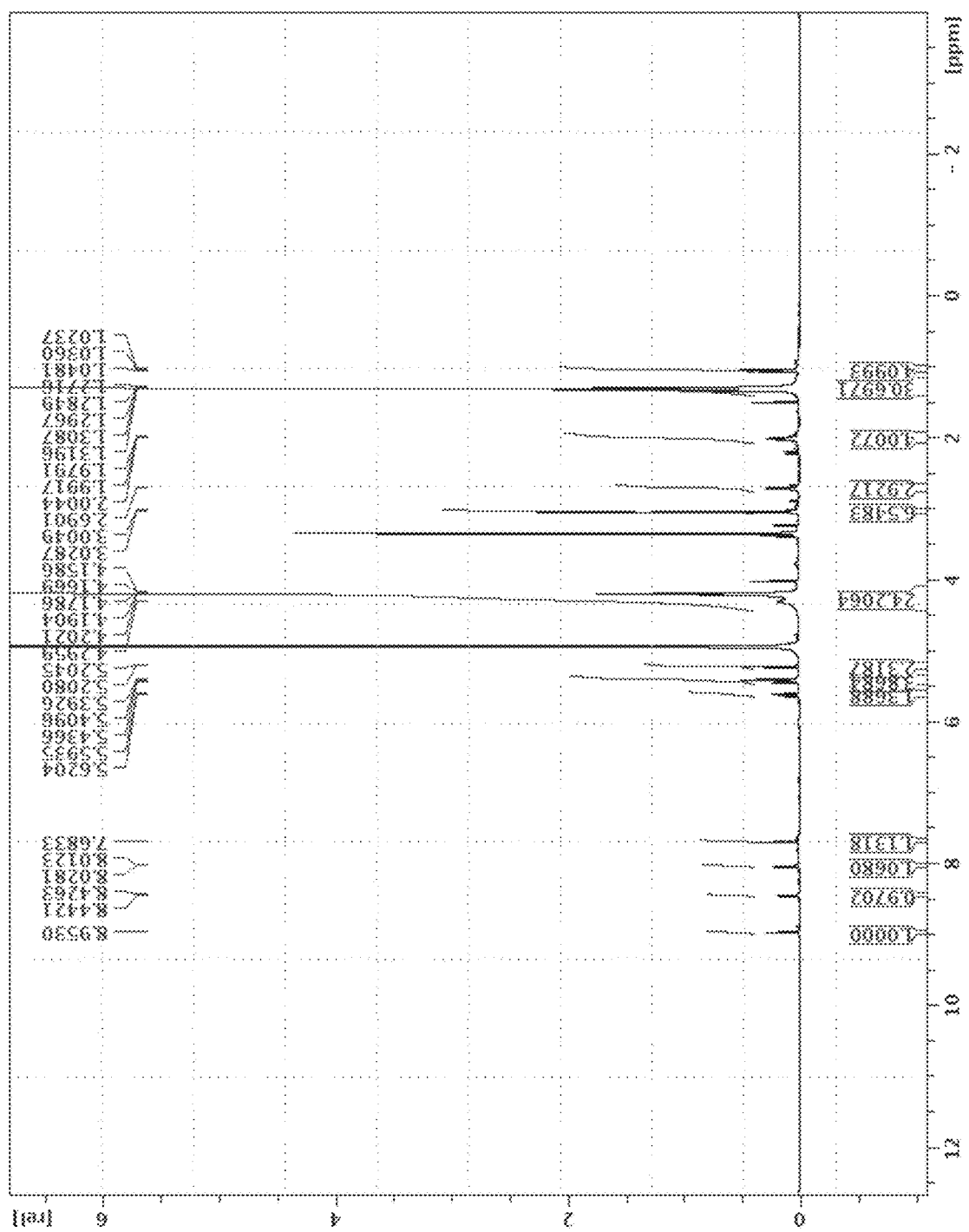
Figure 8A:
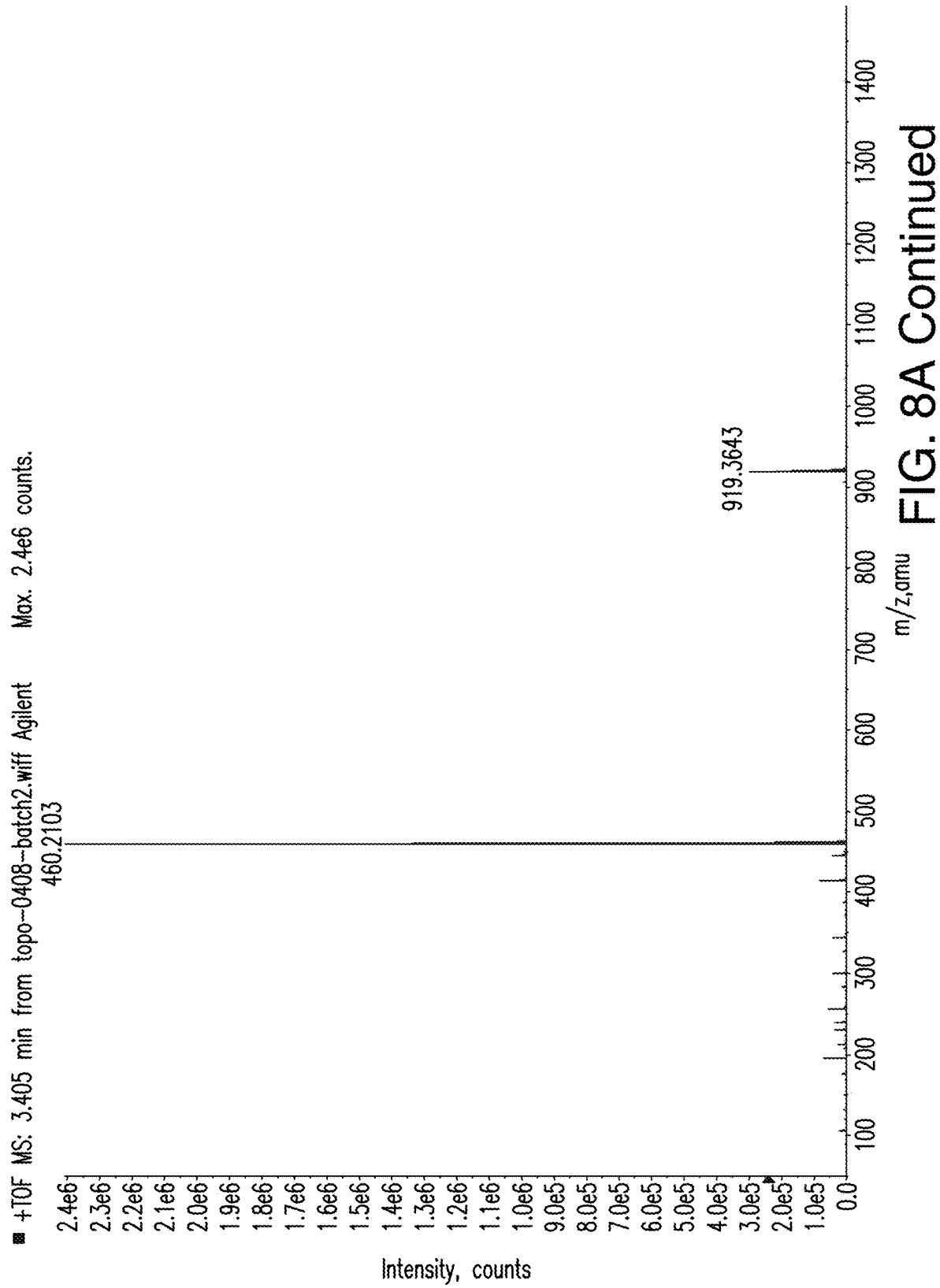
Figure 8A:
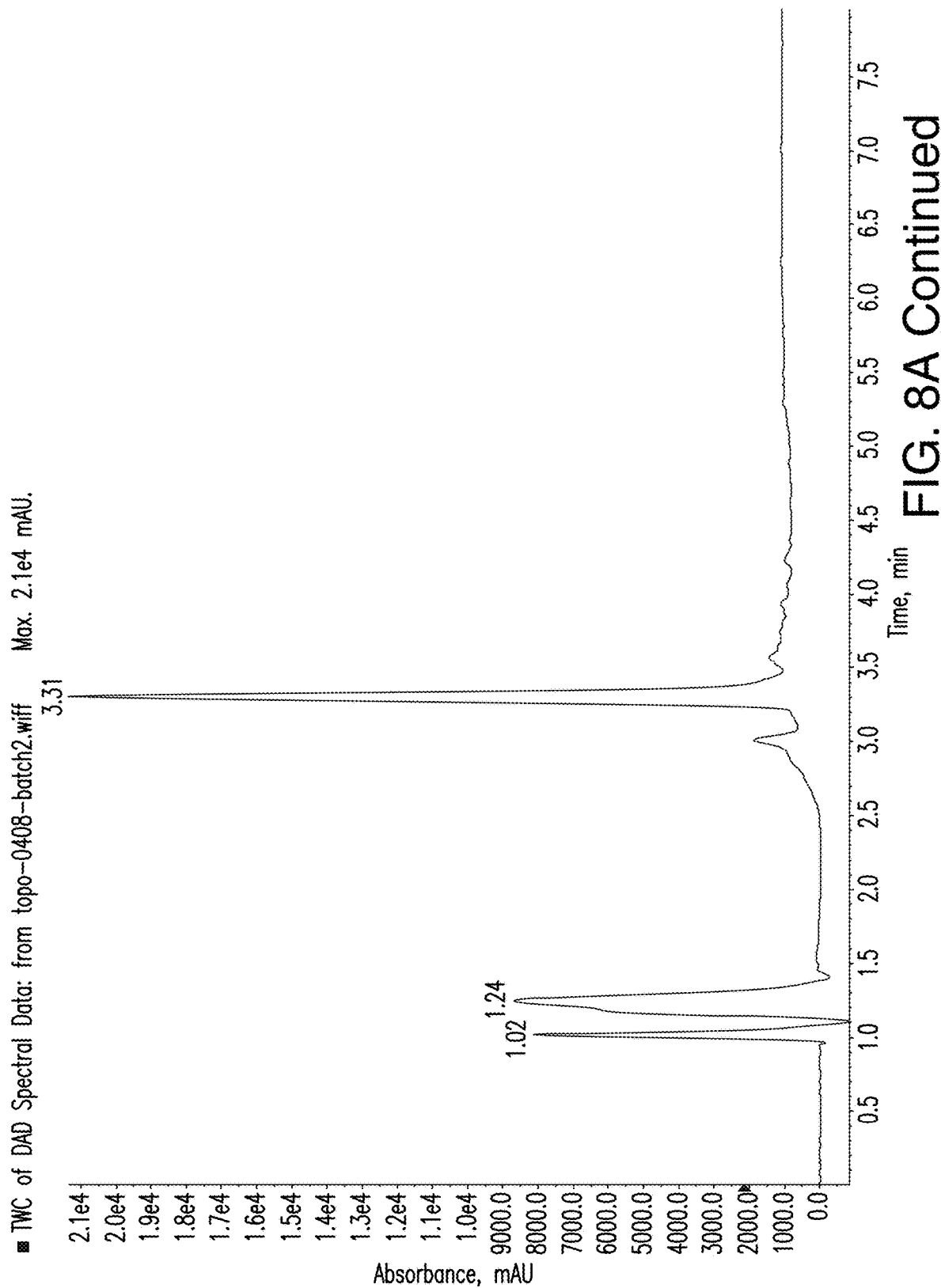
Figure 8B:
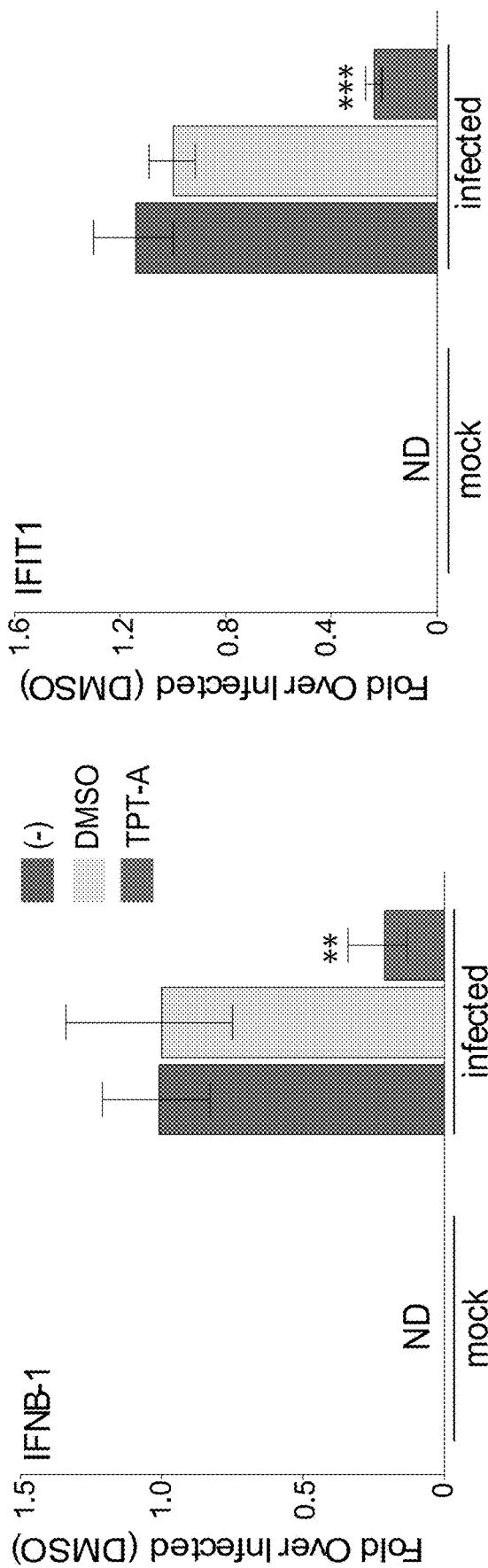
Figure 8C:
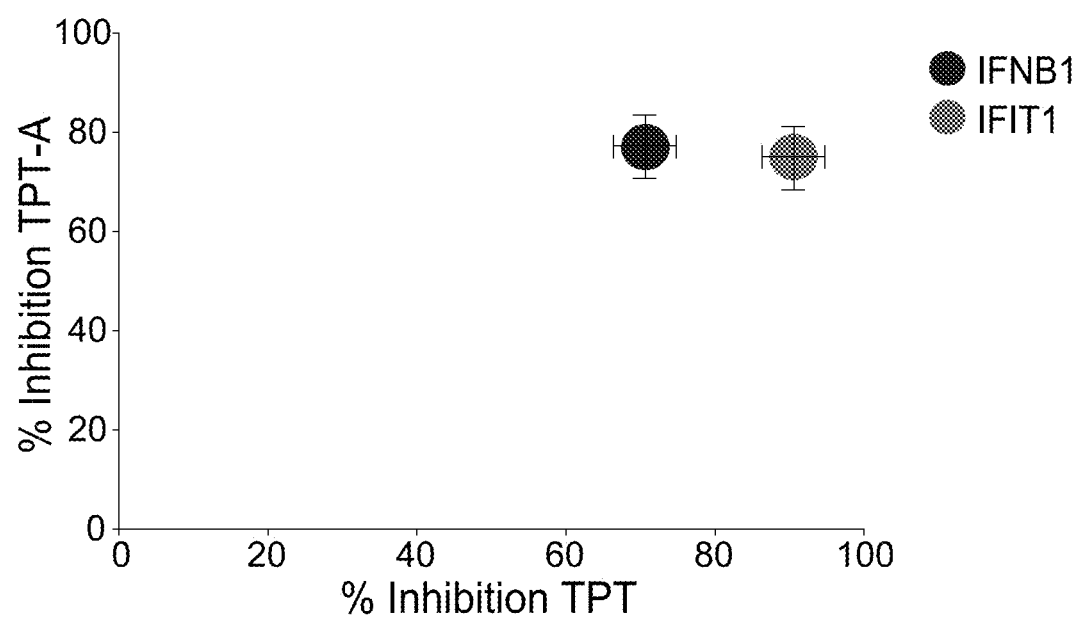

FIG. 8A-C depicts the synthesis and activity of Topotecan-Alkyne (TPT-A). (8A) 1HNMR (MeOH-d4, 600 MHz) and HRMS spectral confirmation for the synthesis and purity of TPT-A. (8B) Gene expression in A549 cells left untreated (−) (left columns) or treated with 100 nM of DMSO (middle columns) or Topotecan-Alkyne (TPT-A) (right columns), assessed 4 hours after mock treatment or infection with PR8ΔNS1 virus. (8C) Percent inhibition of the representative antiviral genes shown in (8B) in A549 cells treated with 100 nM of TPT (x-axis) or TPT-A (y-axis), assessed 4 hours after infection with PR8ΔNS1 virus. *P<0.05, P<0.005 and *P<0.0005 (calculated with a student's t-test). nd=not detected. Data are from three independent experiments and mean and s.d. are indicated (8B, 8C).

Figure 9A:
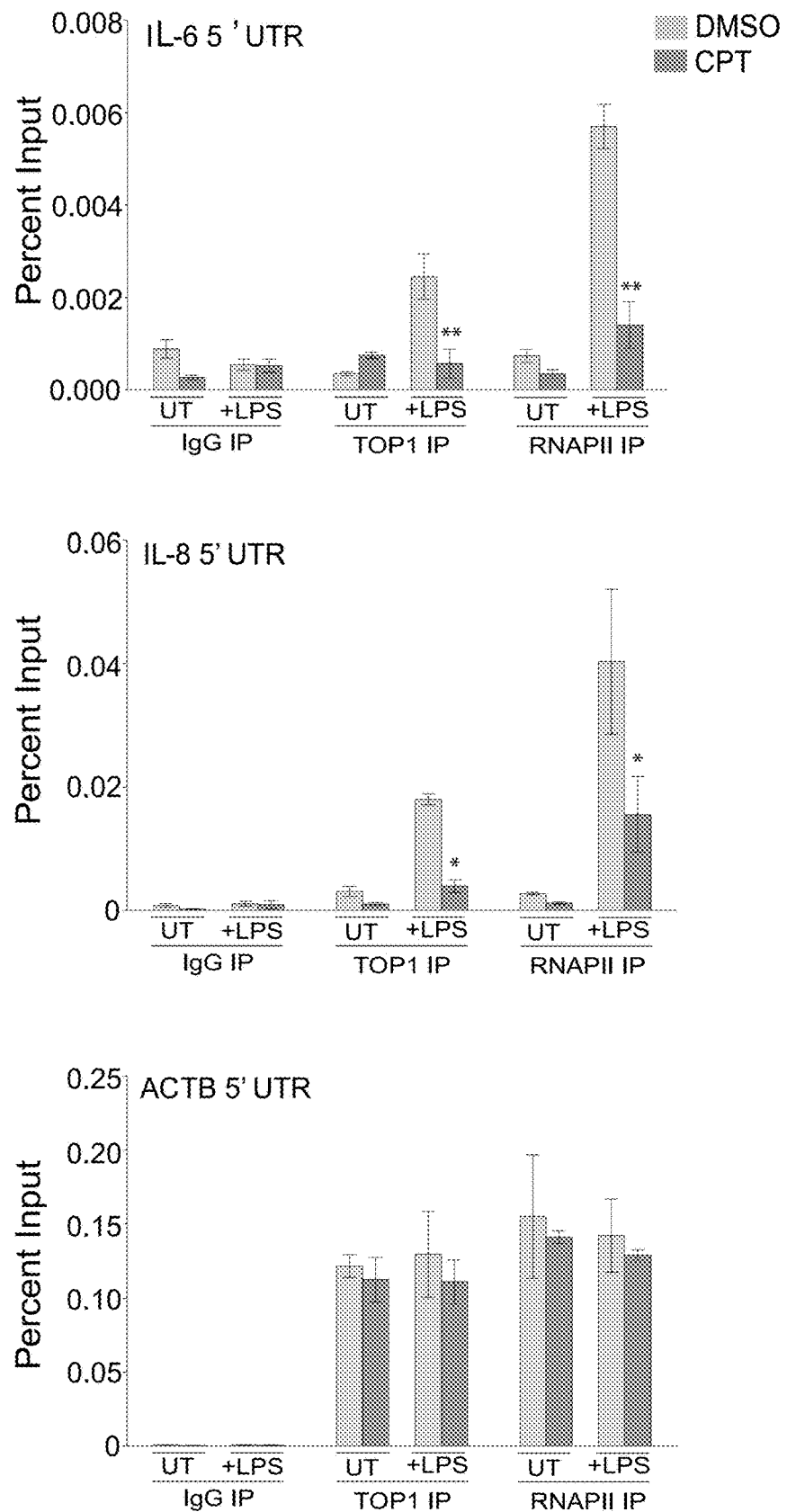
Figure 9B:
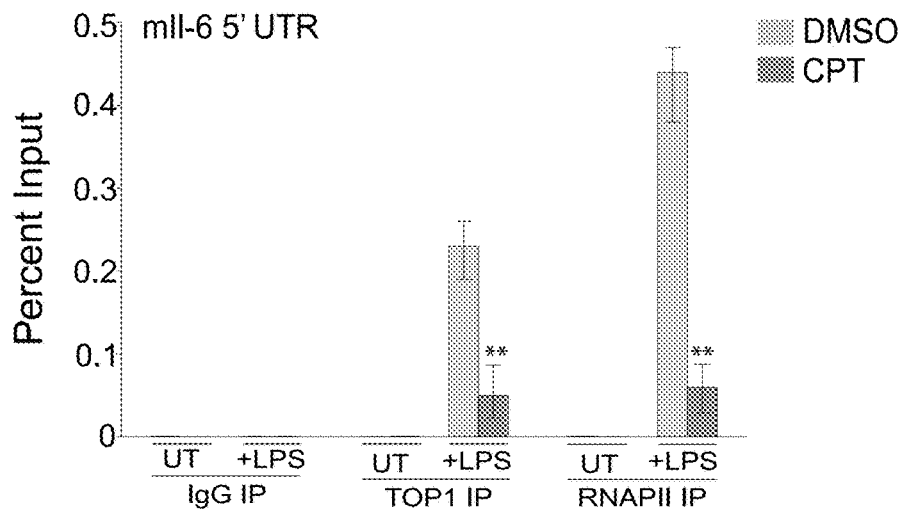
Figure 9B:
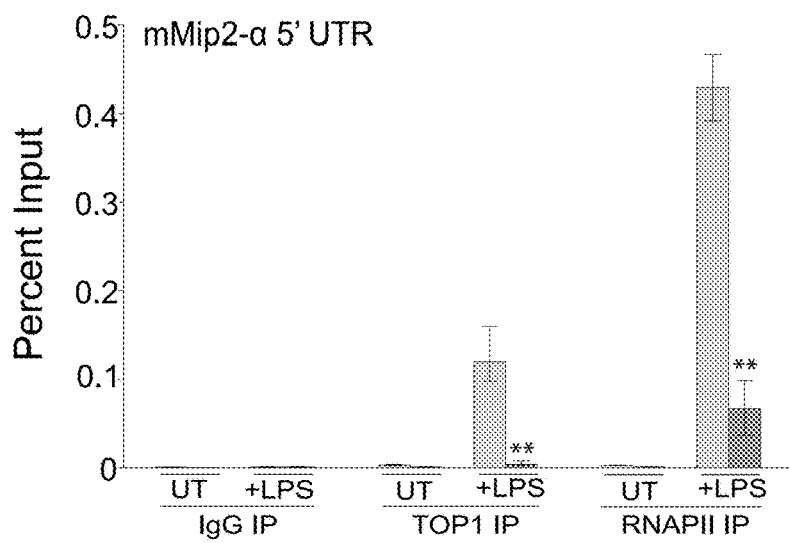
Figure 9B:
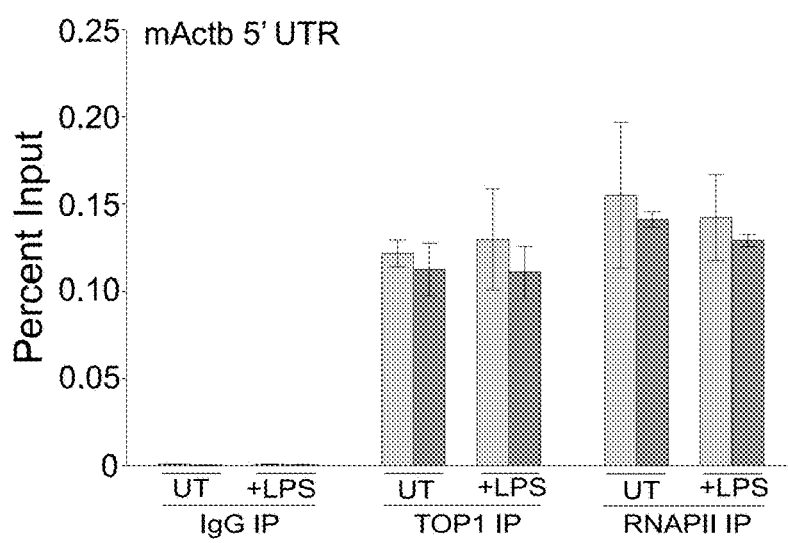
Figure 10A:
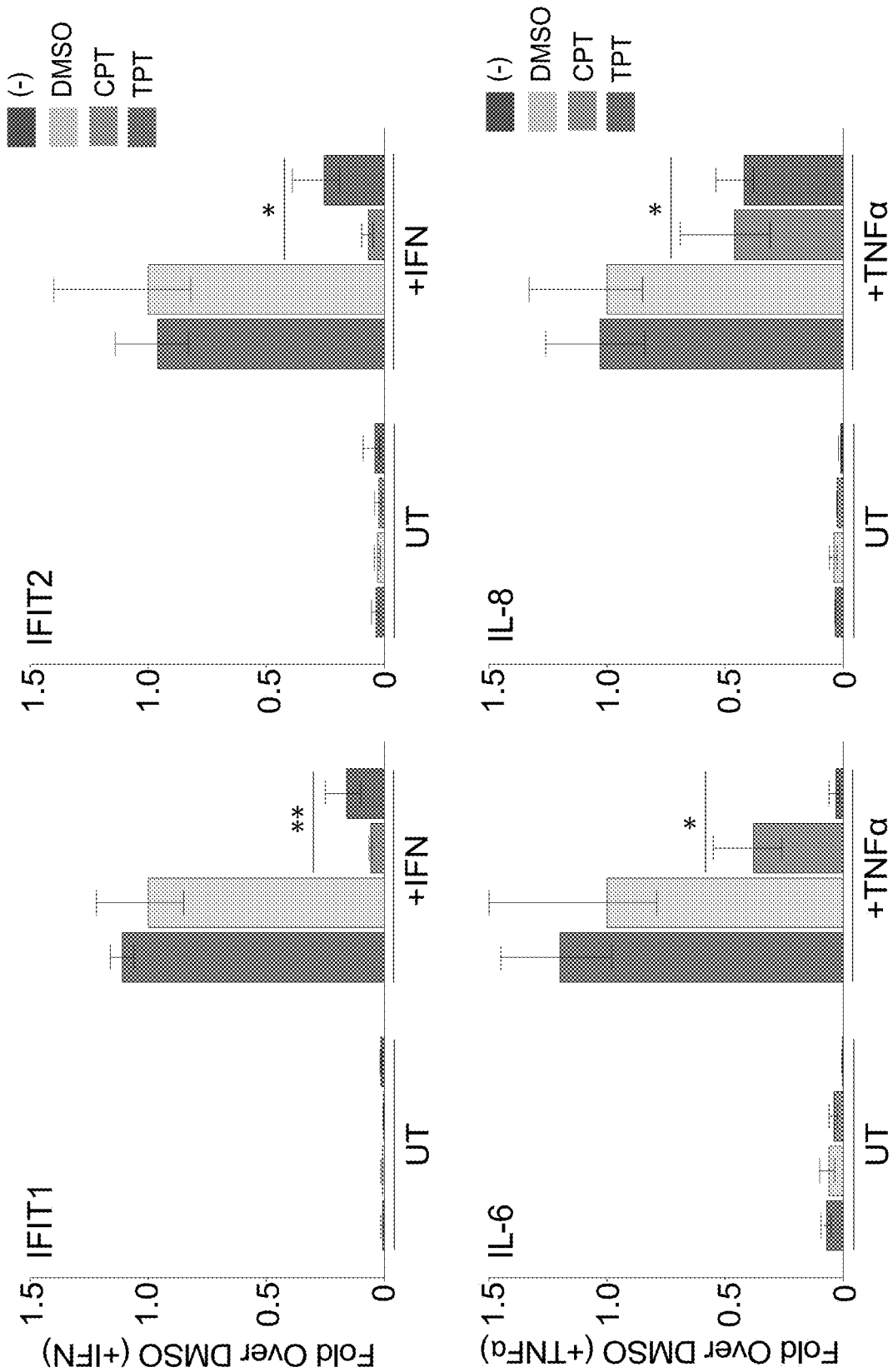
Figure 10B:
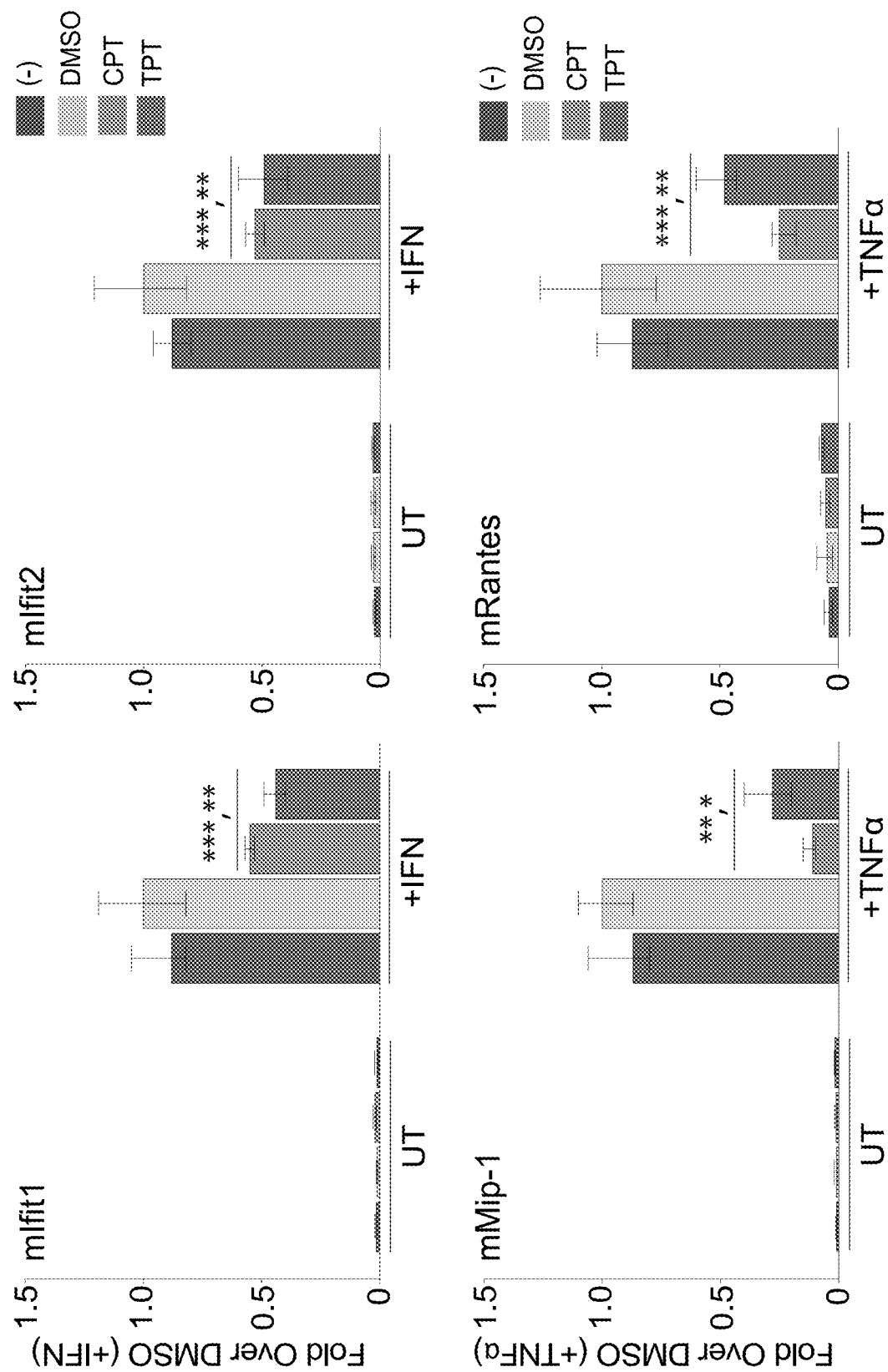
Figure 10C:
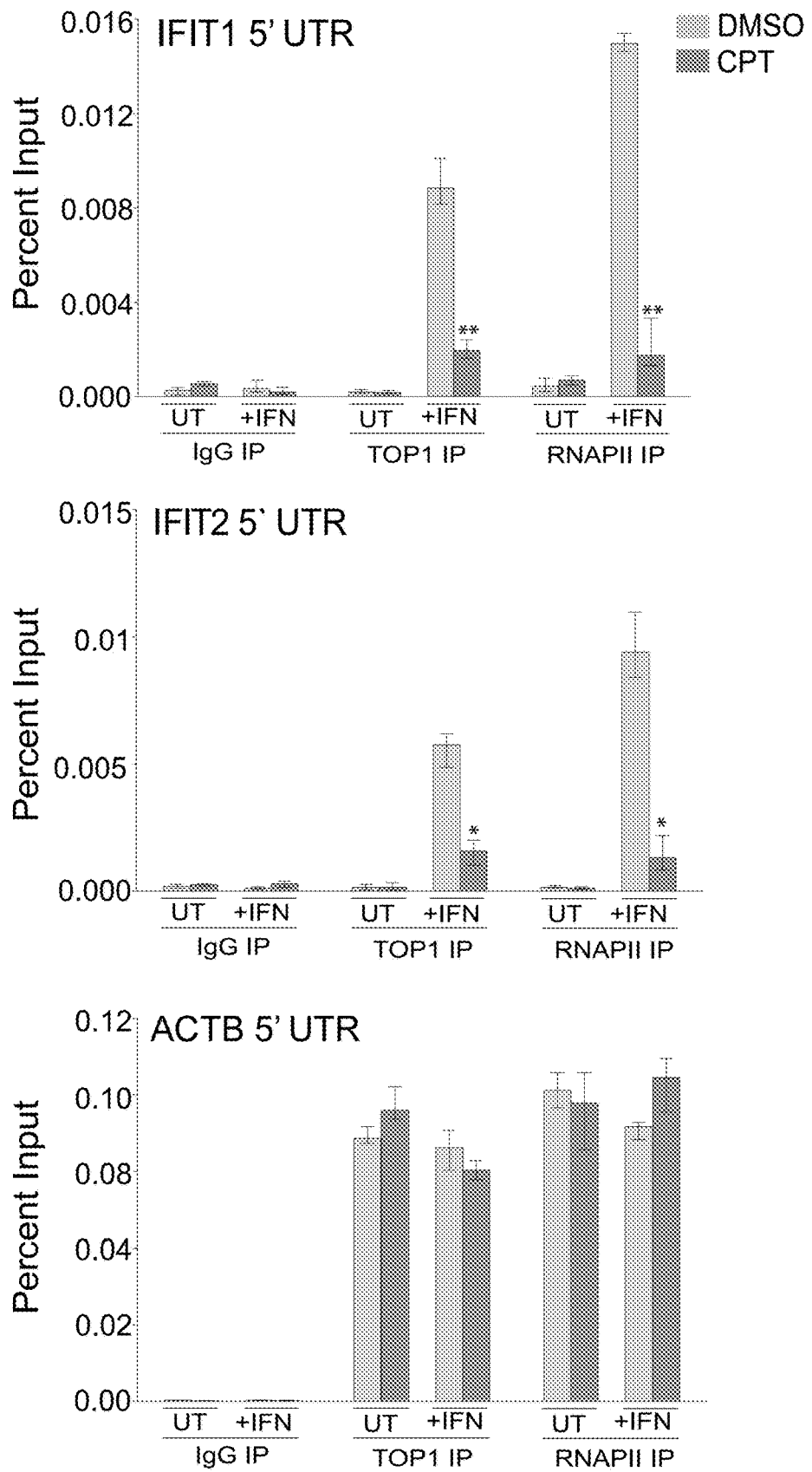
Figure 10D:
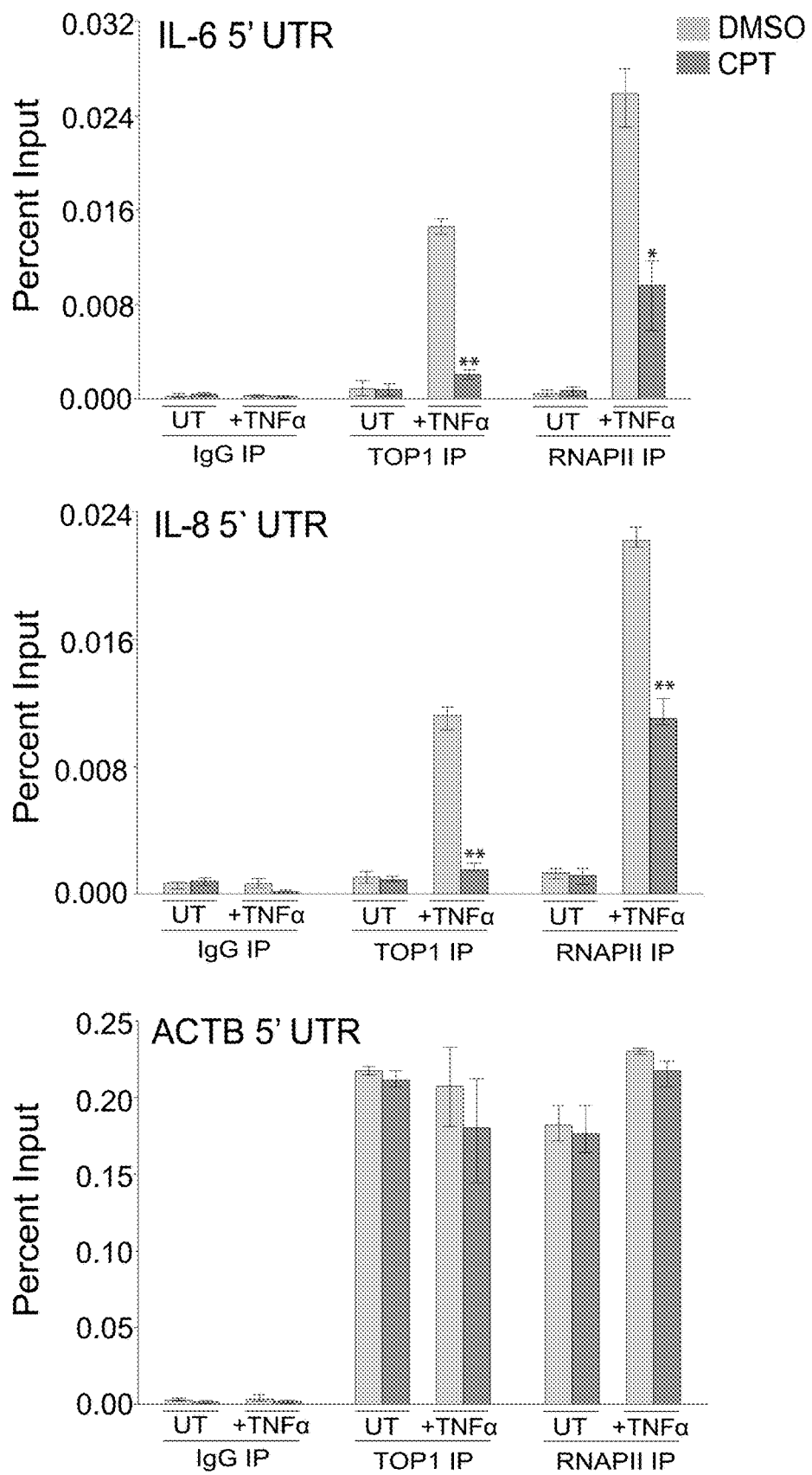

FIG. 9A-B shows RNAPII and Top1 chromatin occupancy during LPS treatment. ChIP-qPCR analysis of endogenous RNAPII and Top1 at the transcriptional start sites of IL-6, IL-8 and ACTB in A549 cells (9A) and of mIL-6, mCxcl2 and mActb in RAW 264.7 cells (9B), treated with DMSO or CPT, in the presence of LPS (+LPS) or not (UT). *P<0.05 and **P<0.005 (calculated with a student's t-test). Data are from two independent experiments (mean and s.d.)

FIG. 10A-D demonstrates that CPT and TPT inhibit expression of genes induced by inflammatory cytokines. (10A, 10B) Gene expression levels in A549 (10A) or RAW 264.7 (10B) cells left untreated (−) (left-most columns) or treated with DMSO (middle left columns), CPT (middle right columns) or TPT (right-most columns), in presence or not (UT) of exogenous IFN-β(+IFN, top panel) or TNFα(+ TNFα, lower panel). (10C, 10D) ChIP-qPCR analysis of endogenous RNAPII and Top1 at the transcriptional start sites of IFIT1, IFT2 and ACTB (C) or IL-6, IL-8 and ACTB (10D) in A549 cells treated with DMSO or CPT, in presence or not (UT) of exogenous IFN-β (+IFN) (C) or TNFα (+TNF) (10D). *P<0.05, P<0.005 and *P<0.0005 (calculated with a student's t-test). Data are from two (10C, 10D) or three independent experiments (10A, 10B). Mean and s.d. are indicated.

FIG. 11A-D shows that CPT treatment inhibits inflammatory gene transcription without inducing cell death in vivo. C57BL/6J mice were treated (LPS+CPT) or not (LPS) with CPT before and after LPS injection to induce septic shock. Ninety minutes later, spleens were harvested and used for flow cytometry and qPCR analyses. (11A) Left, Side scatter (SSC-A) and forward scatter (FSC-A) of the whole hematopoietic splenic population showing the original gate used in 11A, 11B and 11C. Center and left, dot plots showing further gating strategies. (11B) Histograms comparing the incorporation of a Live/Dead dye after gating on R1, R2, R3 and R4. (11C) CD69 expression after gating on R3. (11D) Transcriptional levels of indicated inflammatory genes in the tissue. Data are representative (11A-11C) or a pool (11D) of two independent experiments, n=6 untreated (LPS) and n=7 CPT-treated (LPS+CPT) individual mice. **P<0.005, calculated with a student's t-test and mean and s.d. are indicated.

Figure 12:
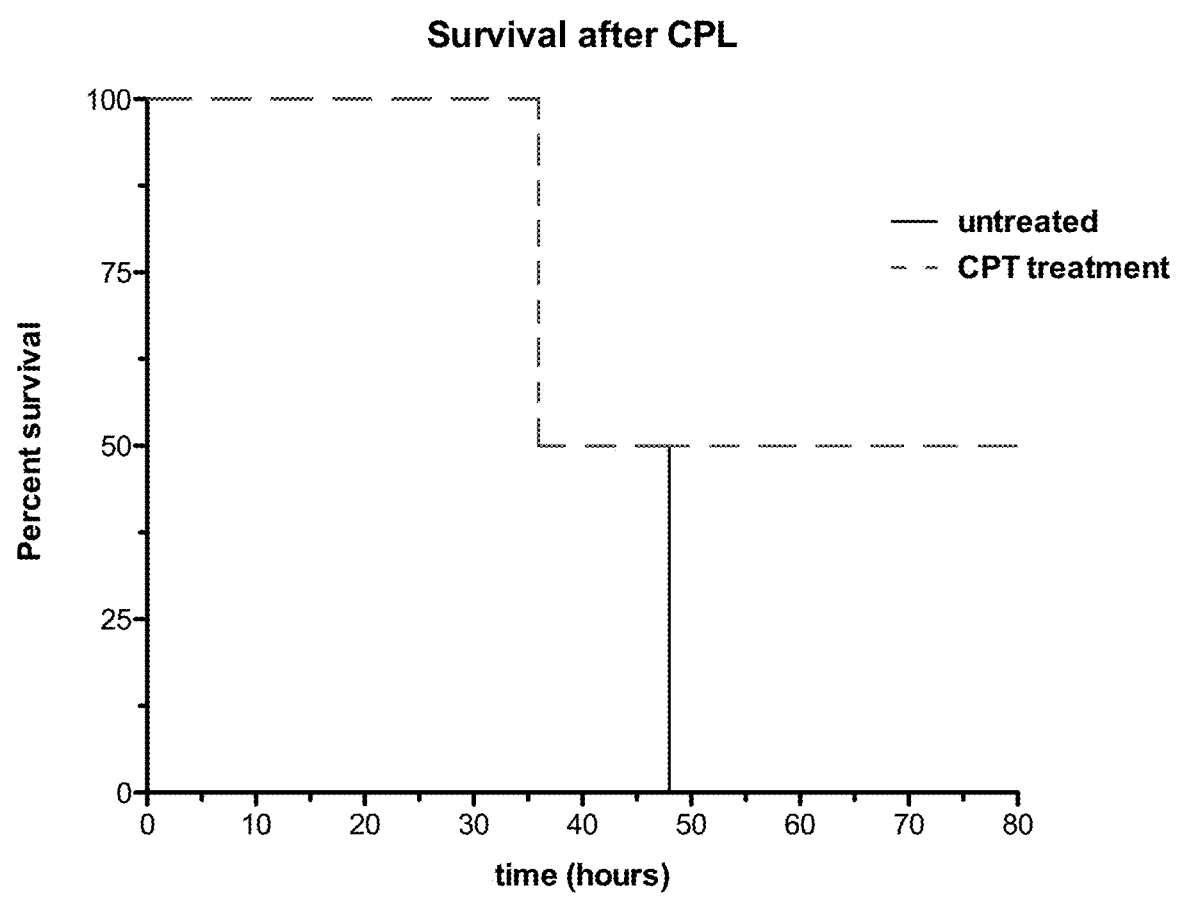

FIG. 12 shows the effects of CPT treatment in mice after cecal ligation puncture (CLP). 10-12 weeks old C57BL/6J mice underwent cecal ligation puncture procedure. In order to test the protective effect of the Top1 inhibitor camptothecin (CPT, dotted line), mice were allowed to recover from surgery and anesthesia for 6 hours and then injected intravenously with CPT at the dose of 30 mg/kg of body weight. Animals were further injected intravenously with 30 mg/kg of CPT twice at day 2 post-surgery, and intraperitoneally (i.p.) with 60 mg/kg of the drug at day 3 post-surgery. n=4 individual mice per group.

Figure 13:
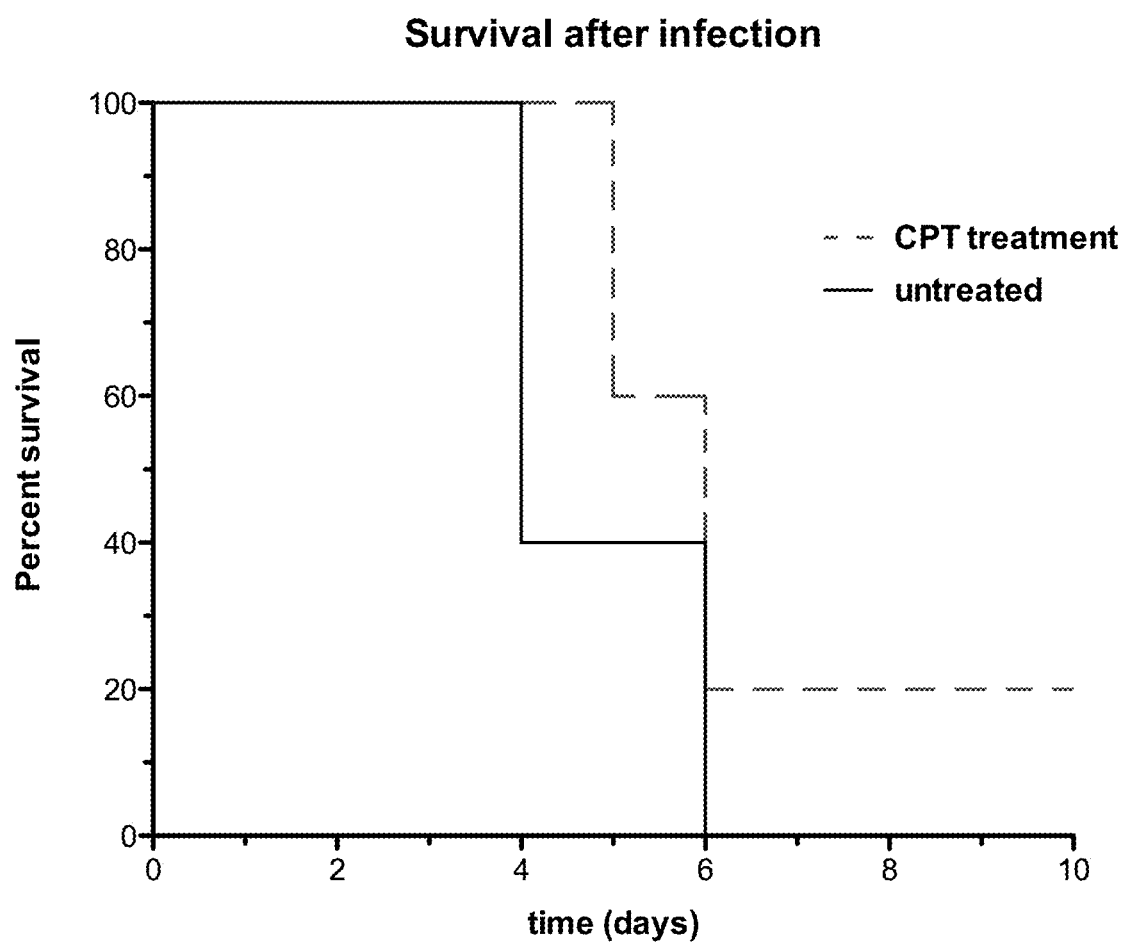

FIG. 13 shows the effects of CPT treatment on mice infected with Ebola virus (EBOV). Survival curve of seven week old female BALB/c mice i.p. infected with $10^3$ PFU of the murine adapted EBOV. Infected mice were left untreated, or treated with CPT (dotted line) i.p.: 30 mg/kg at day 1, 2, 3 and 4 post-infection. n=5 individual mice per group.

Figure 14:
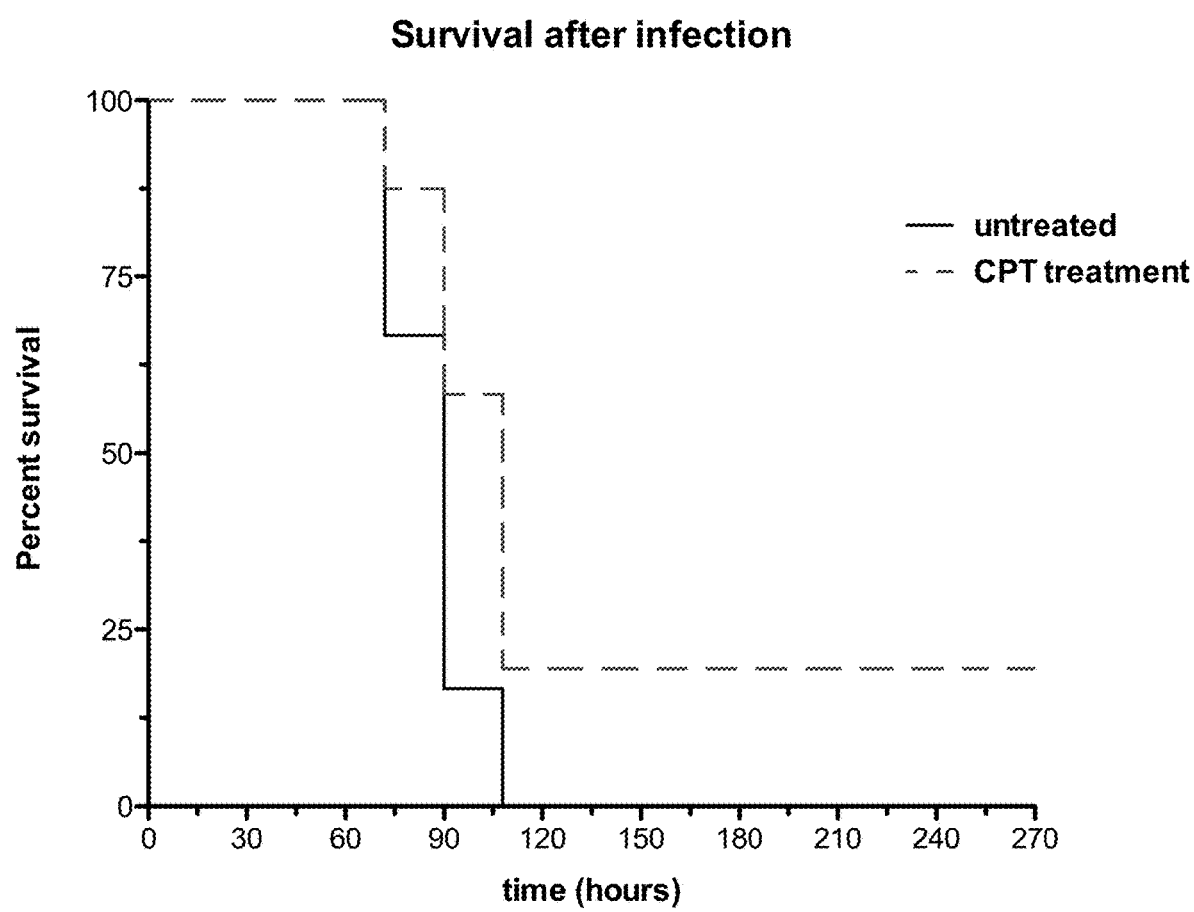

FIG. 14 shows the effects of CPT treatment in Guinea Pigs infected with *Legionella pneumophila*. Young female Hartley stock guinea pigs (4-5 weeks old) were infected intratracheally under anesthesia with a clinical isolate strain of *Legionella pneumophila* serogroup 1, isolated from a patient by the Mount Sinai Hospital clinical microbiology laboratory and designated *L. pneumophila* strain Mount Sinai 1. Each animal received $10^6$ colony-forming units (CFU) of *Legionella* in sterile water. Animals were injected intraperitoneally with 30 mg/kg of the compound CPT (dotted line) at 12 and 36 hours after infection and then with 60 mg/kg of the compound at 60 and 84 hours after infection. n=9 individuals guinea pigs per group.

DETAILED DESCRIPTION OF THE INVENTION

As specified in the Background Section, there is a great need in the art to identify technologies for treating diseases and conditions characterized by exacerbated immune responses and use this understanding to develop novel therapeutics for the treatment of such diseases and conditions.

Embodiments of the present invention relate generally to methods of treating such diseases, states or conditions and more specifically to use of inhibitors of topoisomerase I to control the exacerbated immune response elicited by these diseases, states or conditions. Surprisingly, as demonstrated herein, the use of low amounts of such inhibitors cause inhibition of Top1 without affecting cell viability, while still providing the required effects on inflammatory gene expression that can result in the exacerbated immune response. The Top1 inhibitor at the therapeutically effective dosage and/or duration of treatment used in the methods does not form the typical long-lasting cleavage complex resulting in DNA damage, as evidenced by the absence of detrimental effect in vitro and in vivo on cellular viability.

In some embodiments of the present invention, a method of treating a disease, condition, disorder or state characterized by an exacerbated immune response comprises administration of a therapeutically effective amount of at least one compound that inhibits Top1 activity. In other embodiments, a method of treating such disease, condition, disorder or state comprises administration of a pharmaceutical composition comprising at least one compound that inhibits Top1 activity and may comprise other pharmaceutically acceptable compounds such as a carrier.

In some embodiments of the present invention, a compound that inhibits Top1 activity comprises chemical and/or biological inhibitors and combinations thereof.

In some embodiments of the present invention, the chemical inhibitor is selected from the group consisting of camptothecin, topotecan, irinotecan, plant-derived phenols, indenoisoquinolines and lamellarin D and derivatives thereof.

More than one chemical inhibitor may be utilized in the treatment method. Indenoisoquinolines are preferred in some embodiments.

In other embodiments of the present invention, the biological inhibitor is selected from the group consisting of (i) silencing or interfering nucleic acids specific to and/or capable of binding Top1; (ii) transcriptional regulators of Top1; (iii) translational regulators of Top1; and (iv) post-translational regulators of Top1. Exemplary silencing or interfering nucleic acids include but are not limited to siRNA specific to Top1. Exemplary transcriptional regulators of Top1 include but are not limited to transcription factors, transcription activators, repressors, and/or small molecules affecting transcription and the proteins involved in such process. Exemplary translational and post-translational regulators include but are not limited to regulators that phosphorylate and/or dephosphorylate Top1. More than one biological inhibitor may be utilized in the treatment method. In some embodiments, siRNA is a preferred biological inhibitor.

In some embodiments of the present invention, the at least one compound that inhibits Top1 activity is an aptamer that is capable of binding to the Top1 protein or a nucleic acid encoding Top1. More than one aptamer may be utilized in the treatment method.

In some embodiments of the present invention, the method comprises treating a disease, condition, state and/or disorder selected from the group consisting of sepsis, septic shock, acute liver failure, endotoxic or exotoxic shock, inflammatory bowel disease (IBD), graft-versus host disease (GVHD), ulcerative colitis (UC), Crohn's disease, diabetes (e.g., diabetes mellitus type 1), multiple sclerosis, arthritis (e.g., rheumatoid arthritis), Graves' disease, lupus erythematosus, ankylosing spondylitis, psoriasis, Behcet's disease, autistic enterocolitis, Guillain-Barre Syndrome, myasthenia gravis, pemphigus vulgaris, acute disseminated encephalomyelitis (ADEM), transverse myelitis autoimmune cardiomyopathy, Celiac disease, dermatomyositis, Wegener's granulomatosis, allergy, asthma, contact dermatitis, atherosclerosis (or any other inflammatory condition affecting the heart or vascular system), autoimmune uveitis, as well as other autoimmune skin conditions, autoimmune kidney, lung, or liver conditions and autoimmune neuropathies.

In some embodiments, the disease, condition, state and/or disorder preferably comprises sepsis, septic shock and/or acute liver failure.

In some embodiments, the method comprises treating a disease, condition, infection, state and/or disorder that is characterized by an exacerbated immune response and/or cytokine storm.

In some embodiments, the disease, condition, state and/or disorder may be caused and/or exacerbated by a microorganism or portion of a microorganism. Exemplary microorganisms and portions of microorganisms include but are not limited to Ebola virus, Lassa virus, Influenza virus, *Legionella*, lipopolysaccharide (LPS), and bacterial endotoxins/exotoxins.

In some embodiments, the treatment method comprises the co-administration of at least one other therapeutic agent.

In some embodiments, the co-administered therapeutic agent is selected from the group consisting of (i) therapeutic agents that block inflammation; (ii) one or more anti-tumor antibodies or antibodies directed at a pathogenic antigen or allergen; (iii) other immunomodulatory treatments; (iv) one or more bromodomain inhibitors; and (v) one or more antibiotics, anti-fungal drugs, anti-viral drugs, anti-parasitic drugs, or anti-protozoal drugs, including any combination of the foregoing.

In some embodiments, the therapeutically effective amount of the at least one compound is determined by the disease, condition, infection, state and/or disorder. Certain diseases, conditions, infections, states and/or disorders may require a higher amount of the at least one compound than other such diseases, conditions, infections, states and/or disorders in order to be therapeutically effective. Further, certain microorganisms and/or portions of microorganisms may cause and/or exacerbate, directly or indirectly, diseases, conditions, infections, states and/or disorders with exacerbated immune responses that may require a higher amount of the at least one compound than those caused and/or exacerbated by other microorganisms and/or portions of microorganisms. However, the therapeutically effective amount used in methods of the present invention will be lower and/or administered or provided less frequently than the therapeutically effective amount of a Top1 inhibitor required to treat cancers and/or tumors. The therapeutically effective amount used to inhibit inflammatory gene expression does not affect cell viability both in vitro and in vivo.

Surprising evidence is provided herein demonstrating that during a cytokine storm or exacerbated immune response, inhibition of Top1, as well as Top1 depletion, specifically suppresses genes induced by microbial agents. Such short and reversible inhibition results from the use of low therapeutically effective doses of the Top1 inhibitor that do not result in cell death from DNA damage and/or shorter duration of administration. It is hypothesized that a reason for this reversible inhibition is that the characteristic long-lasting and stable cleavage complexes found with use of higher amounts of Top1 inhibitor and/or amounts administered over longer periods of time simply are not formed with use of lower amounts and/or shorter administration periods; however, there may be other causes of the reversible inhibition. Additional evidence demonstrated herein reveals a surprising gene specific activator-like role for Top1.

Though Top1 inhibitors such as the camptothecins, indenoisoquinolines and their derivatives have been shown to be effective in treating cancers and/or tumors, it is surprising that Top1 inhibitors (both biological and chemical) are effective in treating inflammatory conditions such as, for example and not limitation, exacerbated immune responses related to some diseases, conditions, infections, states and/or disorders. It is also unexpected that use of relatively low amounts of the inhibitor and/or administration for a relatively shorter period of time would be effective in controlling such exacerbated immune responses. It is further unexpected that Top1 inhibitors could enhance transcription of genes, including relatively short genes and/or genes under 200 kb in length (23). The findings described herein that Top1 inhibitors can enhance transcription of genes, especially relatively short genes, sharply contrasts with the long-held belief that inhibition of Top1 necessarily results in suppression of genes. It is further unexpected that a biological inhibitor of Top1, such as for example and not limitation siRNA, is capable of achieving the same effect on gene regulation as a chemical inhibitor, as demonstrated herein.

To simplify and clarify explanation, the method of treatment is described below as a method of treating immune responses exacerbated by certain diseases, disorders, conditions, states and/or infections, including but not limited to bacterial and/or viral infections. One skilled in the art will recognize, however, that the invention is not so limited. The method of treatment can also be used in treating any disease, disorder, condition, state and/or infection state that is characterized by an exacerbated immune response.

Definitions

To facilitate an understanding of the principles and features of the various embodiments of the invention, various illustrative embodiments are explained below and herein. Although exemplary embodiments of the invention are explained in detail, it is to be understood that other embodiments are contemplated. Accordingly, it is not intended that the invention is limited in its scope to the details of construction and arrangement of components set forth in the following description or examples. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. Any dimensions listed in the various drawings are for illustrative purposes only and are not intended to be limiting. Other dimensions and proportions are contemplated and intended to be included within the scope of the invention.

As used herein, the term "Topoisomerase I" or "Top1" refers to an enzyme that plays a role in coiling and uncoiling DNA. Specifically, Top1 is capable of cutting a single strand of the DNA double helix by an ATP-mediated reaction in order to repair damage and then rejoining the cut strand by ligation. The damaged DNA can be repaired by re-synthesizing the damaged section, homologous recombination or other repair method. In order for Top1 to repair damaged DNA, the enzyme must cause the relaxation of the coil of the two DNA strands, cleave the DNA in the proper area so the damage can be repaired, and then after the cuts are made and replication or repair is complete, re-ligate and pair the DNA strands back together to reform the coil. The Top1-DNA complex is transient. If the activity of Top1 is inhibited, then the enzyme is no longer able to rejoin the cleaved DNA strand after the cleavage step. This failure to repair the damage results in cell death.

The terms "Top1 inhibitor" or "topoisomerase I inhibitor" refer to a compound that is capable of blocking or preventing, whether permanently or only for a short term, the ability of Top1 to re-ligate the DNA strands. These inhibitors can be chemical or biological in nature or can be aptamers that are capable of specifically interacting with Top1. Exemplary chemical inhibitors serve to stabilize the Top1-DNA complex, also known as the cleavage complex, such that the DNA ligation is prevented and the single-strand breaks are not repaired. These breaks lead to lethal DNA damage. Known Top1 inhibitors include camptothecins and their derivatives such as topotecan (HYCAMTIN®, available from GlaxoSmithKline) and irinotecan (Pfizer). To overcome certain undesirable physical properties and physiological effects of camptothecins and derivatives, a second class of chemical inhibitors has been developed. This second class includes indenoisoquinolines and their derivatives. In contrast to camptothecins and their derivatives, the indenoisoquinolines are: 1) chemically stable in blood, 2) inhibitors of Top1 cleavable complexes at distinct sites, 3) not substrates of membrane transporters, and 4) more effective as anti-tumor agents in animal models. Indenoisoquinolines form ternary complexes of Top1 and DNA and act as interfacial inhibitors. Another class of Top1 inhibitors includes plant-derived phenols such as, for example and not limitation, genistein, quercetin, resveratrol and epigallocatechin gallate, all of which can have phytoalexin functionality. Lamellarin D is also known to be a Top1 chemical inhibitor. Indenoisoquinolines are preferred chemical inhibitors of Top1 in some embodiments of the present invention. Exemplary biological inhibitors include silencing and/or interfering nucleic acids, such as for example and not limitation siRNA, that is capable of binding with specificity to nucleic acids encoding the topoisomerase I gene, as well as molecules that can regulate the transcription, translation, and post-translational modification of topoisomerase I. As Top1 is known to have a phosphorylation site, molecules that regulate the phosphorylation and dephosphorylation of Top1 can also be considered Top1 inhibitors.

As used herein, the term "exacerbated immune response" is a synonym for "cytokine storm," "cytokine cascade" and/or "hypercytokinemia," all of which describe the exaggerated, often inappropriate immune response caused by rapidly proliferating T-cells or other immune cells and an ongoing positive feedback loop with both pro-inflammatory cytokines such as, for example and not limitation, TNF-alpha, IL-6, IL-8, and anti-inflammatory cytokines such as, for example and not limitation, IL-10 and IL-1 receptor antagonist serving to further increase the proliferation of T-cells and other immune cells. Such an immune response is potentially fatal, with suggested treatments including, for example and not limitation, compounds known to inhibit the T-cell response and TNF-alpha inhibitors. Different triggers for cytokines include but are not limited to lipopolysaccharide (LPS), Gram-positive toxins, fungal toxins, glycosylphosphatidylinositol (GPI) or modulation of RIG-1 gene expression. These varying causes usually generate different ranges, profiles, concentrations and kinetics of cytokine and chemokine generation and release.

As used herein, the term "bromodomain" or "BRD" refers to an approximately 110 amino acid protein structural motif that recognizes and binds to acetylated lysine residues, such as those on the N-terminal tails of histones or on chromatin-modifying/associated enzymes such as histone deacetylases, transcription factors and transcription activators. Lysine acetylation is similar to protein phosphorylation in its prevalence as a post-translational modification and also has a large effect on the physicochemical property of the modified residue. The addition of an acetyl moiety to the lysine leads to neutralization of charge, which can significantly influence protein conformation and protein-protein interactions, thus resulting in the modulation of enzyme activities and protein assembly. Proteins with BRD motifs have higher affinity for regions where multiple acetylation sites exist in proximity. This recognition is often a prerequisite for protein-histone association and chromatin remodeling. Acetylation is also often found in large macromolecular complexes that are present in the cell nucleus, suggesting a key role of acetylation in the regulation of chromatin and transcriptional control. In particular, the unstructured tails of histones commonly contain many acetyl lysine modifications. Histone acetylation levels are often associated with an open chromatin architecture and transcriptional activation, as well as chromatin condensation, regulation of metabolism and DNA repair. Acetylation or modification of lysine residues in transcription factors can either stimulate or silence gene transcription. Recruitment of proteins to macromolecular complexes by acetylated lysine residues is mediated by BRDs, which are evolutionarily highly conserved protein-interaction modules that recognize ɛ-N-lysine acetylation motifs. The conserved BRD fold contains a deep, mostly hydrophobic acetyl lysine binding site, which is a possible target for the development of small pharmaceutically active molecules. Proteins that contain BRDs have been implicated in the development of a large variety of diseases. Exemplary protein families containing BRDs include the BET (bromodomain and extraterminal domain) family as well as histone acetyltransferases, ATP-dependent chromatin-remodeling complexes, methyltransferases (e.g., ASH1L) and transcriptional coactivators. Exemplary BET family members include BRD2, BRD3, BRD4 and BRDT. Dysfunction of these BET family proteins has been linked to diseases such as human squamous cell carcinoma and other forms of cancer.

The term "bromodomain inhibitor" as used herein refers to molecules that can reversibly bind the BRDs of proteins containing these motifs. Such binding prevents protein-protein interaction between the BRD-containing proteins and acetylated histones and transcription factors. Bromodomain inhibitors can include, for example and not limitation, thienodiazepine, JQ1, I-BET 151 (GSK1210151A), I-BET 762 (GSK525762), OTX-015, TEN-010, CPI-203, CPI-0610, RVX-208, LY294002, bromosporine, PFI 1, PFI 3, PFI 4, OF 1 and XD 14.

The term "aptamer" as used herein refers to nucleic acid (i.e., DNA, RNA and/or XNA) or peptide molecules that bind to or interact with a specific target molecule such as Top1. Such binding can disrupt (directly or indirectly) the normal binding activities or interactions of the target molecule with its own target molecules. The aptamer may include a ribozyme to cause self-cleavage in the presence of the target molecule. Nucleic acid aptamers are usually short oligonucleotides and may be modified to prevent or lessen degradation by nucleases. Nucleic acid aptamers may be designed to bind to or interact with various molecular targets such as small molecules, proteins, nucleic acids, and even cells, tissues and organisms. Peptide aptamers are often designed to interfere with protein-protein interactions inside cells and can consist of a short variable peptide domain or loop attached at both ends to a protein scaffold that can serve to greatly increase the aptamer's binding affinity.

As used herein, the terms "silencing nucleic acid" and/or "interfering nucleic acid" refers to a nucleic acid that is capable of regulating expression of a gene and includes the concepts of gene silencing and RNA silencing, of which RNA interference is a specific example. These terms describe the ability of a cell to regulate gene expression during transcription or translation to reduce expression of certain genes. Transcriptional gene silencing can include, for example and not limitation, genomic imprinting, paramutation, transposon silencing, transgene silencing, position effect, RNA-directed DNA methylation, and modification of histones and associated induction of heterochromatin formation (RNA-induced transcriptional silencing). Translational gene silencing can include, for example and not limitation, RNA silencing, RNA interference, and nonsense-mediated decay. RNA silencing allows one or more genes to be downregulated or entirely suppressed by non-coding RNAs, particularly small RNAs. RNA silencing may also refer to the introduction of a synthetic antisense RNA molecule, or to sequence-specific regulation of gene expression triggered by double-stranded RNA (dsRNA). The most common method of RNA silencing is RNA interference (RNAi), in which endogenously expressed small RNAs such as, for example and not limitation, microRNA (miRNA), exogenously derived small interfering RNA (siRNA) and piwi-interacting RNA (piRNA), can induce the degradation of complementary messenger RNA (mRNA) or can repress translation of the mRNA. These small RNAs are typically non-coding RNAs approximately 20-30 nucleotides in length that can function as factors involved in, for example and not limitation, inactivating homologous sequences, promoting endonuclease activity, translational arrest, and/or chromatic or DNA modification. RNA silencing refers to the silencing activity of a range of small RNAs and is generally regarded as a broader category than RNAi. Specifically, RNA silencing may be thought of as referring to the broader scheme of small RNA related controls involved in gene expression and the protection of the genome against mobile repetitive DNA sequences, retroelements, and transposons to the extent that these can induce mutations. Further, the 3' untranslated regions (3'UTRs) of mRNAs often contain regulatory sequences that post-transcriptionally cause RNA interference. Such 3'-UTRs often contain both binding sites for miRNAs as well as for regulatory proteins. By binding to specific sites within the 3'-UTR, miRNAs can decrease gene expression of various mRNAs by either inhibiting translation or directly causing degradation of the transcript. The 3'-UTR also may have silencer regions that bind repressor proteins that inhibit the expression of a mRNA. The 3'-UTR often contains microRNA response elements (MREs), which are sequences to which miRNAs bind.

As used herein, the term "subject" refers to mammals and includes, without limitation, human and veterinary animals. In a preferred embodiment, the subject is human.

As used herein, the term "combination" and/or "co-administration" of a Top1 inhibitor and at least a second pharmaceutically active ingredient means at least two, but any desired combination of compounds can be delivered simultaneously or sequentially (e.g., within a 24 hour period).

In the context of the present invention insofar as it relates to any of the diseases, disorders, conditions or states recited herein, the terms "treat", "treatment", and the like mean to relieve or alleviate at least one symptom associated with such disease, disorder, condition or state, or to slow or reverse the progression of same. Within the meaning of the present invention, the term "treat" also denotes to arrest, delay the onset (i.e., the period prior to clinical manifestation of a disease, disorder, condition or state) and/or reduce the risk of developing or worsening same. E.g., in connection with cancer the term "treat" may mean eliminate or reduce a patient's tumor burden, or prevent, delay or inhibit metastasis, etc. The terms "treat", "treatment", and the like regarding a state, disease, disorder or condition may also include (1) preventing or delaying the appearance of at least one clinical or sub-clinical symptom of the state, disease, disorder or condition developing in a subject that may be afflicted with or predisposed to the state, disease, disorder or condition but does not yet experience or display clinical or subclinical symptoms of the state, disease, disorder or condition; or (2) inhibiting the state, disease, disorder or condition, i.e., arresting, reducing or delaying the development of the state, disease, disorder or condition or a relapse thereof (in case of maintenance treatment) or at least one clinical or sub-clinical symptom thereof; or (3) relieving the state, disease, disorder or condition, i.e., causing regression of the state, disease, disorder or condition or at least one of its clinical or sub-clinical symptoms.

As used herein, the term "therapeutically effective" applied to dose or amount refers to that quantity of a compound or pharmaceutical composition that is sufficient to result in a desired activity upon administration to a subject in need thereof. Within the context of the present invention, the term "therapeutically effective" refers to that quantity of a compound or pharmaceutical composition containing such compound that is sufficient to delay the manifestation, arrest the progression, relieve or alleviate at least one symptom of a state, disease, disorder or condition treated by the methods of the present invention. Note that when a combination of active ingredients is administered the effective amount of the combination may or may not include amounts of each ingredient that would have been effective if administered individually. The therapeutically effective amount of the compound or pharmaceutical composition may be influenced by the state, disease, disorder or condition itself, and/or by the microorganism or portion of the microorganism that is the causative agent of the state, disease, disorder or condition. Importantly, the therapeutically effective amount of the Top1 inhibitor as used to control inflammatory gene expression and thus decrease the exacerbated immune response can be lower than the therapeutically effective amount of such inhibitor in treating cancers and/or tumors, and/or is administered over a shorter period of time than that used to treat cancers and/or tumors. It is possible that the lower therapeutically effective amounts of Top1 inhibitor(s) used in the methods described herein result in decreased or non-existent cleavage complexes, resulting in reversible inhibition, increased cell viability, and/or less or non-existent DNA damage.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D.N. Glover ed. 1985); *Oligonucleotide Synthesis* (M. J. Gait ed. 1984); *Nucleic Acid Hybridization* (B. D. Hames & S. J. Higgins eds. (1985); *Transcription and Translation* (B. D. Hames & S. J. Higgins, eds. (1984); *Animal Cell Culture* (R. I. Freshney, ed. (1986); *Immobilized Cells and Enzymes* (IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994); among others.

Non-limiting examples of the infections, diseases, states and conditions eliciting the exacerbated immune response treatable by the methods of the present invention include, e.g., sepsis, Ebola virus, Lassa virus, Influenza virus, and *Legionella*.

Non-limiting examples of the inflammatory and autoimmune diseases, conditions, disorders and/or states treatable by the methods of the present invention include, e.g., sepsis, septic shock, acute liver failure, endotoxic or exotoxic shock, inflammatory bowel disease (IBD), graft-versus-host disease (GVHD), ulcerative colitis (UC), Crohn's disease, diabetes (e.g., diabetes mellitus type 1), multiple sclerosis, arthritis (e.g., rheumatoid arthritis), Graves' disease, lupus erythematosus, ankylosing spondylitis, psoriasis, Behcet's disease, autistic enterocolitis, Guillain-Barre Syndrome, myasthenia gravis, pemphigus vulgaris, acute disseminated encephalomyelitis (ADEM), transverse myelitis autoimmune cardiomyopathy, Celiac disease, dermatomyositis, Wegener's granulomatosis, allergy, asthma, contact dermatitis, atherosclerosis (or any other inflammatory condition affecting the heart or vascular system), autoimmune uveitis, as well as other autoimmune skin conditions, autoimmune kidney, lung, or liver conditions, autoimmune neuropathies, etc.

It is contemplated that when used to treat various states, diseases, disorders or conditions, the compositions and methods of the present invention can be combined with other therapeutic agents suitable for the same or similar states, diseases, disorders or conditions. Also, two or more embodiments of the invention may be also co-administered to generate additive or synergistic effects. When co-administered with a second therapeutic agent, the embodiment of the invention and the second therapeutic agent may be simultaneously or sequentially (in any order). Suitable therapeutically effective dosages for each agent may be lowered due to the additive action or synergy.

As a non-limiting example, the invention can be combined with other therapies that block inflammation (e.g., via blockage of IL1, INFα/β, IL6, TNF, IL13, IL23, etc.).

The methods of the invention can be combined with other therapies that suppress inflammatory gene expression, such as for example and not limitation, bromodomain inhibitors.

The methods of the invention can be also administered in combination with an anti-tumor antibody or an antibody directed at a pathogenic antigen or allergen.

The methods of the invention can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 41BB, OX40, etc.). The inhibitory treatments of the invention can be also combined with other treatments that possess the ability to modulate NKT function or stability, including but not limited to CD1d, CD1d-fusion proteins, CD1d dimers or larger polymers of CD1d either unloaded or loaded with antigens, CD1d-chimeric antigen receptors (CD1d-CAR), or any other of the five known CD1 isomers existing in humans (CD1a, CD1b, CD1c, CD1e), in any of the aforementioned forms or formulations, alone or in combination with each other or other agents.

For treatment of infections, combined therapy of the invention can encompass co-administering compositions and methods of the invention with an antibiotic, an anti-fungal drug, an anti-viral drug, an anti-parasitic drug, an anti-protozoal drug, or a combination thereof.

Non-limiting examples of useful antibiotics include lincosamides (clindomycin); chloramphenicols; tetracyclines (such as Tetracycline, Chlortetracycline, Demeclocycline, Methacycline, Doxycycline, Minocycline); aminoglycosides (such as Gentamicin, Tobramycin, Netilmicin, Amikacin, Kanamycin, Streptomycin, Neomycin); beta-lactams (such as penicillins, cephalosporins, Imipenem, Aztreonam); vancomycins; bacitracins; macrolides (erythromycins), amphotericins; sulfonamides (such as Sulfanilamide, Sulfamethoxazole, Sulfacetamide, Sulfadiazine, Sulfisoxazole, Sulfacytine, Sulfadoxine, Mafenide, p-Aminobenzoic Acid, Trimethoprim-Sulfamethoxazole); Methenamin; Nitrofurantoin; Phenazopyridine; trimethoprim; rifampicins; metronidazoles; cefazolins; Lincomycin; Spectinomycin; mupirocins; quinolones (such as Nalidixic Acid, Cinoxacin, Norfloxacin, Ciprofloxacin, Perfloxacin, Ofloxacin, Enoxacin, Fleroxacin, Levofloxacin); novobiocins; polymixins; gramicidins; and antipseudomonals (such as Carbenicillin, Carbenicillin Indanyl, Ticarcillin, Azlocillin, Mezlocillin, Piperacillin) or any salts or variants thereof. See also Physician's Desk Reference, 59th edition, (2005), Thomson P D R, Montvale N.J.; Gennaro et al., Eds. Remington's The Science and Practice of Pharmacy, 20th edition, (2000), Lippincott Williams and Wilkins, Baltimore Md.; Braunwald et al., Eds. Harrison's Principles of Internal Medicine, 15th edition, (2001), McGraw Hill, NY; Berkow et al., Eds. The Merck Manual of Diagnosis and Therapy, (1992), Merck Research Laboratories, Rahway N.J. Such antibiotics can be obtained commercially, e.g., from Daiichi Sankyo, Inc. (Parsipanny, N.J.), Merck (Whitehouse Station, N.J.), Pfizer (New York, N.Y.), Glaxo Smith Kline (Research Triangle Park, N.C.), Johnson & Johnson (New Brunswick, N.J.), AstraZeneca (Wilmington, Del.), Novartis (East Hanover, N.J.), and Sanofi-Aventis (Bridgewater, N.J.). The antibiotic used will depend on the type of bacterial infection.

Non-limiting examples of useful anti-fungal agents include imidazoles (such as griseofulvin, miconazole, terbinafine, fluconazole, ketoconazole, voriconazole, and itraconizole); polyenes (such as amphotericin B and nystatin); Flucytosines; and candicidin or any salts or variants thereof. See also Physician's Desk Reference, 59th edition, (2005), Thomson P D R, Montvale N.J.; Gennaro et al., Eds. Remington's The Science and Practice of Pharmacy 20th edition, (2000), Lippincott Williams and Wilkins, Baltimore Md.; Braunwald et al., Eds. Harrison's Principles of Internal Medicine, 15th edition, (2001), McGraw Hill, NY; Berkow et al., Eds. The Merck Manual of Diagnosis and Therapy, (1992), Merck Research Laboratories, Rahway N.J.

Non-limiting examples of useful anti-viral drugs include interferon alpha, beta or gamma, didanosine, lamivudine, zanamavir, lopanivir, nelfinavir, efavirenz, indinavir, valacyclovir, zidovudine, amantadine, rimantidine, ribavirin, ganciclovir, foscarnet, and acyclovir or any salts or variants thereof. See also Physician's Desk Reference, 59th edition, (2005), Thomson P D R, Montvale N.J.; Gennaro et al., Eds. Remington's The Science and Practice of Pharmacy 20th edition, (2000), Lippincott Williams and Wilkins, Baltimore Md.; Braunwald et al., Eds. Harrison's Principles of Internal Medicine, 15th edition, (2001), McGraw Hill, NY; Berkow et al., Eds. The Merck Manual of Diagnosis and Therapy, (1992), Merck Research Laboratories, Rahway N.J.

Non-limiting examples of useful anti-parasitic agents include chloroquine, mefloquine, quinine, primaquine, atovaquone, sulfasoxine, and pyrimethamine or any salts or variants thereof. See also Physician's Desk Reference, $59^{th}$ edition, (2005), Thomson P D R, Montvale N.J.; Gennaro et al., Eds. Remington's The Science and Practice of Pharmacy 20th edition, (2000), Lippincott Williams and Wilkins, Baltimore Md.; Braunwald et al., Eds. Harrison's Principles of Internal Medicine, $15^{th}$ edition, (2001), McGraw Hill, NY; Berkow et al., Eds. The Merck Manual of Diagnosis and Therapy, (1992), Merck Research Laboratories, Rahway N.J.

Non-limiting examples of useful anti-protozoal drugs include metronidazole, diloxanide, iodoquinol, trimethoprim, sufamethoxazole, pentamidine, clindamycin, primaquine, pyrimethamine, and sulfadiazine or any salts or variants thereof. See also Physician's Desk Reference, $59^{th}$ edition, (2005), Thomson P D R, Montvale N.J.; Gennaro et al., Eds. Remington's The Science and Practice of Pharmacy 20th edition, (2000), Lippincott Williams and Wilkins, Baltimore Md.; Braunwald et al., Eds. Harrison's Principles of Internal Medicine, $15^{th}$ edition, (2001), McGraw Hill, NY; Berkow et al., Eds. The Merck Manual of Diagnosis and Therapy, (1992), Merck Research Laboratories, Rahway N.J.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

EXAMPLE 1

Top1 Inhibitors Affect Immune Responses

Identification of Novel Chromatin Regulators Controlling PAMP-Induced Genes.

Figure 1A:
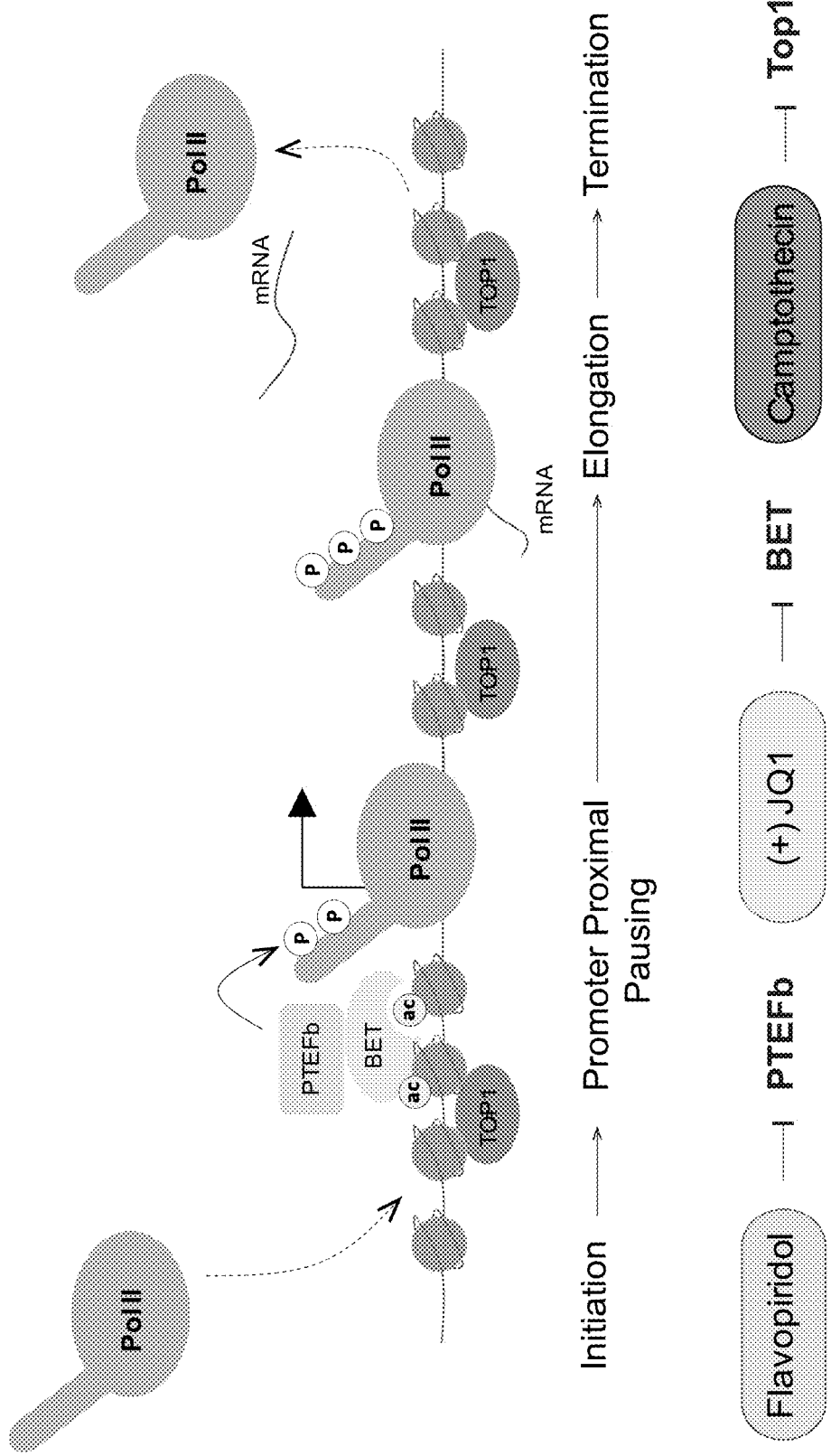
FIG. 1A-E demonstrates that Top1 inhibition limits RNA-PII at PAMP-induced loci. (1A) Schematic representation of factors controlling different phases of RNA polymerase II (RNAPII) mediated transcription. Chemical inhibitors Flavopiridol (medium gray), (+)JQ1 (light gray) and Camptothecin (dark gray) are color-coded according to their protein targets. (1B) Quantitative PCR (qPCR) results showing the expression levels of representative viral PAW-induced genes IFNB and IFIT1, in response to the influenza PR8ΔNS1 virus infection in untreated (−) or DMSO and inhibitors treated human A549 cells. (1C) Heatmap showing fold change in gene expression levels in A549 cells not transfected (UT) or transfected with a Top1-specific siRNA (siTop1) as compared to non-targeting control siRNA treated (siCtrl) cells during infection with influenza PR8ΔNS1 for genes differentially expressed between siTop1 and siCtrl 4 hours p.i. (p0.01; ANOVA with post-hoc TUKEY HSD test). Known interferon-stimulated (ISGs) and cytokine coding genes are indicated in the adjacent heat map. A table summarizing the top five pathways affected by Top1 depletion during infection is also shown (top right). (1D) Expression levels of IFIT1 and IFIT2 genes in response to influenza PR8ΔNS1 infection in A549 cells treated with 0.5 μM of DMSO or CPT or 100 nM Topotecan (TPT) at 4 hours p.i. (left sets of bars) or 16 hours after washout (white, right sets of bars). (1E) Mass-spectrometry data showing representative virus-induced and housekeeping protein levels in response to influenza PR8ΔNS1 infection in A549 cells treated with 0.5 μM of DMSO or CPT at 6 hours p.i. *P<0.05, P<0.005 and *P<0.0005 (calculated with a student's t-test). Data are from three independent experiments (1B-1D) and from two independent experiments (1E). Mean and standard deviation (s.d.) are indicated.
Figure 1B:
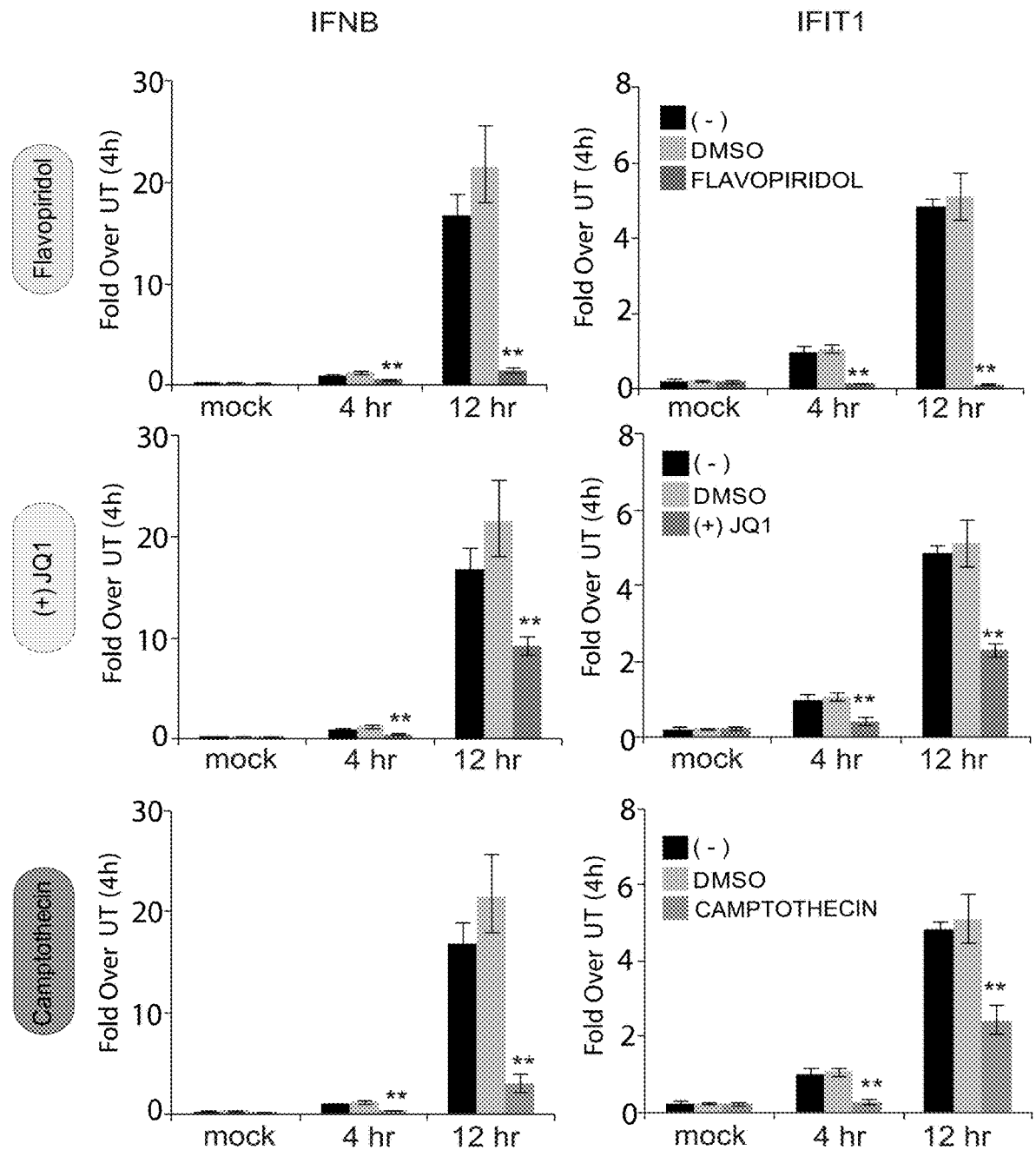
Figure 4A:
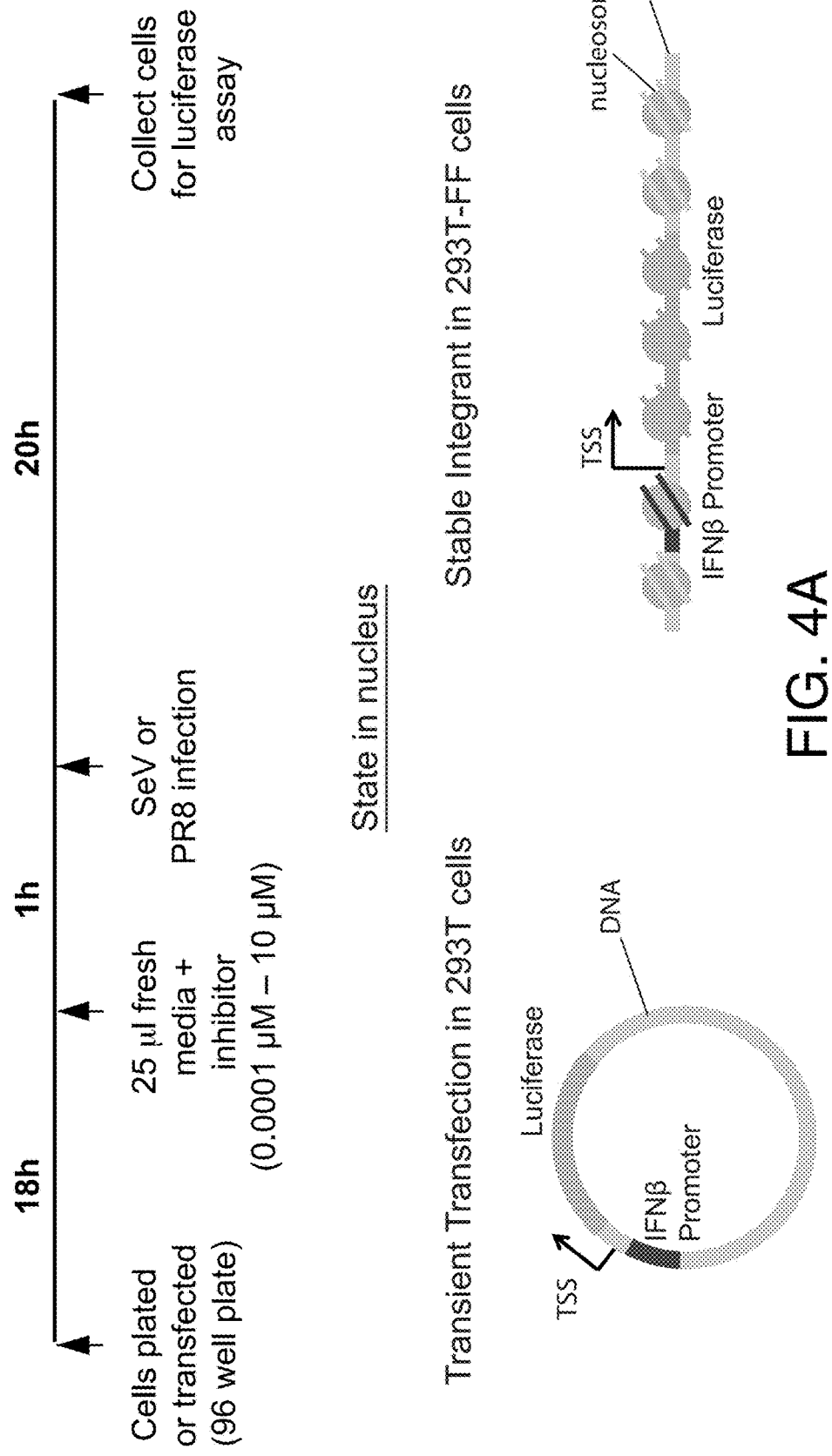
FIG. 4A-C depicts a screen for chemical compounds inhibiting antiviral gene expression according to some embodiments of the present invention. (4A) Schematic of the screening for chemical compounds inhibiting the antiviral response. (4B) Chemical structure of the compounds used in the screen and their corresponding known targets. (4C) Top panels, y-axis labeled % RLU, shows that the IFN-β-luciferase stable reporter cells, 293T-FF were infected with Sendai or PR8ΔNS1 virus in the presence of increasing concentrations (0.0001 to 10 μM) of DMSO or the indicated compounds. Compounds that at 20 hours post-infection (p.i.) showed inhibitory effects on luciferase expression are indicated in gray. Middle panels, 293T cells transiently-transfected with the IFN-β-luciferase reporter plasmid were infected with Sendai or PR8ΔNS1 virus in the presence of increasing concentrations (0.0001 to10 μM) of compounds. Lower panels, cytotoxicity of compounds used in the screening was determined by measuring release of ATP into supernatants.
Figure 4B:
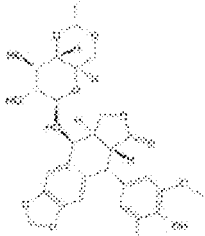
Figure 4C:
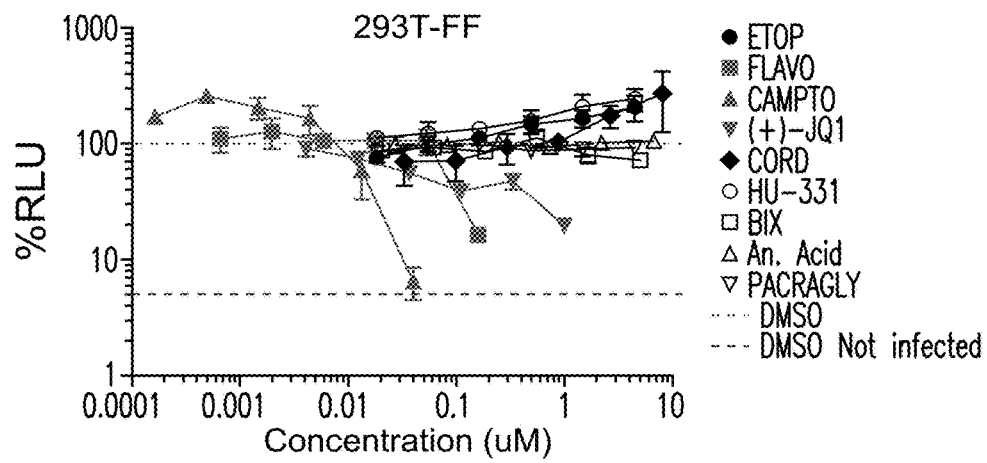
Figure 4C:
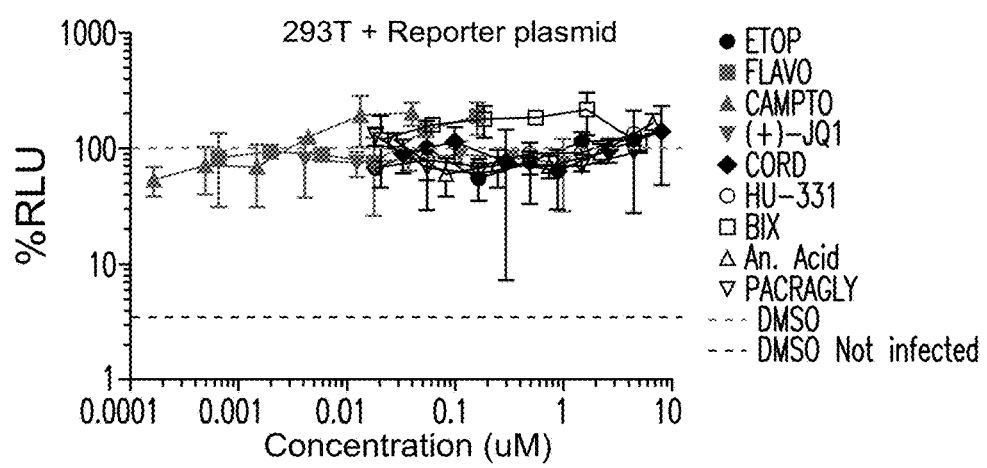
Figure 4C:
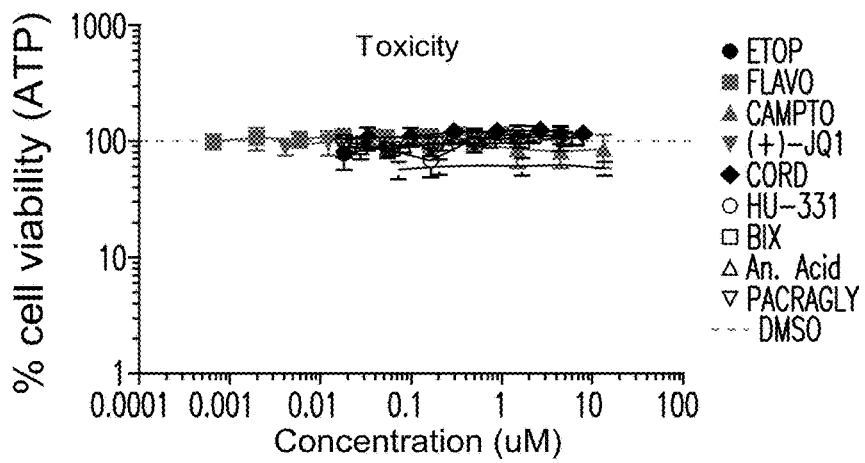
Figure 4C:
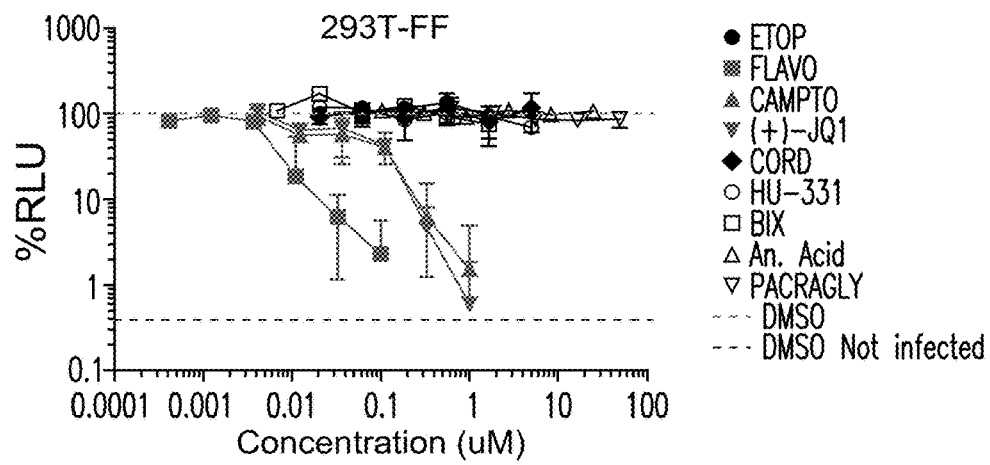
Figure 4C:
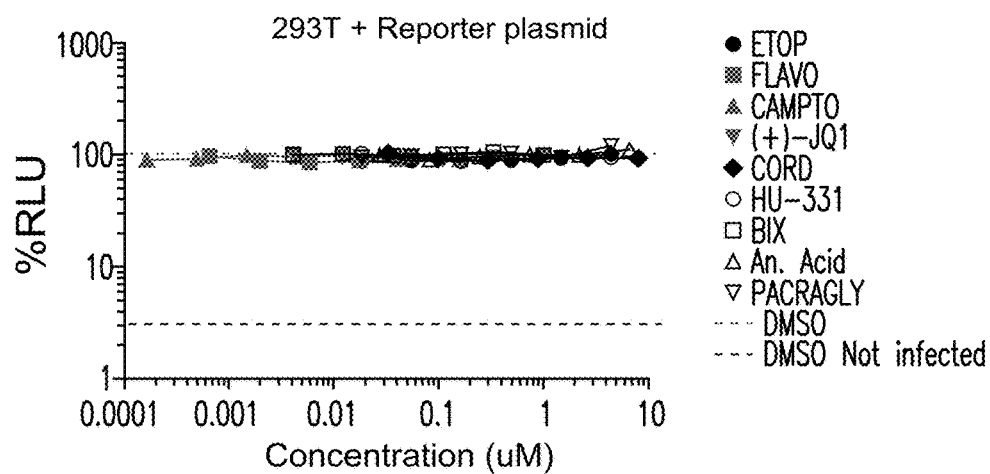
Figure 4C:
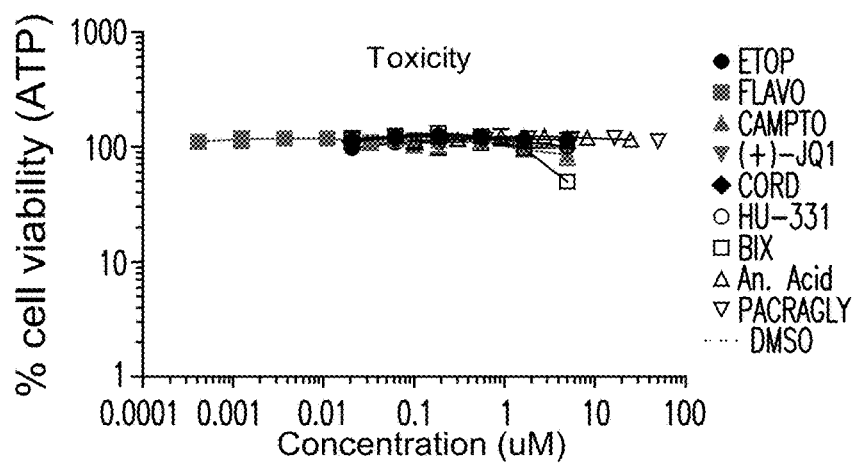

A goal was to identify novel regulatory mechanisms controlling the transcriptional response to pathogens by the innate immune system. A reporter assay was designed to compare the potency of the transcriptional response to viral PAMPs and its dependence on a chromatin environment (FIG. 4A). Both the influenza A virus strain PR8ΔNS1 and Sendai virus were used since they are known to be strong inducers of PAMP-mediated gene expression (FIG. 4C)(11). Nine chemical inhibitors (FIG. 4B) with already known or inferred chromatin targets were selected and their activity was gauged at various concentrations (FIG. 4C)(12-20). Notably, none of the inhibitors displayed cytotoxic effects across the concentration ranges we used (FIG. 4C, lower panels). This analysis revealed that flavopiridol (FVD), (+)-JQ1 and camptothecin (CPT) effectively inhibit the interferon-beta (IFN-β)-driven transcription from chromatinized templates (FIG. 1A and FIG. 4C). These observations were further reinforced by the efficacy of the three compounds to suppress the endogenous expression of two key PAW-induced genes, IFN-β and IFN-induced protein with tetratricopeptide repeats 1 (IFIT1) in the human lung epithelial cell line A549, at early (4 hours) and late (12 hours) time points following PR8ΔNS1 virus infection (FIG. 1B).

Figure 5A:
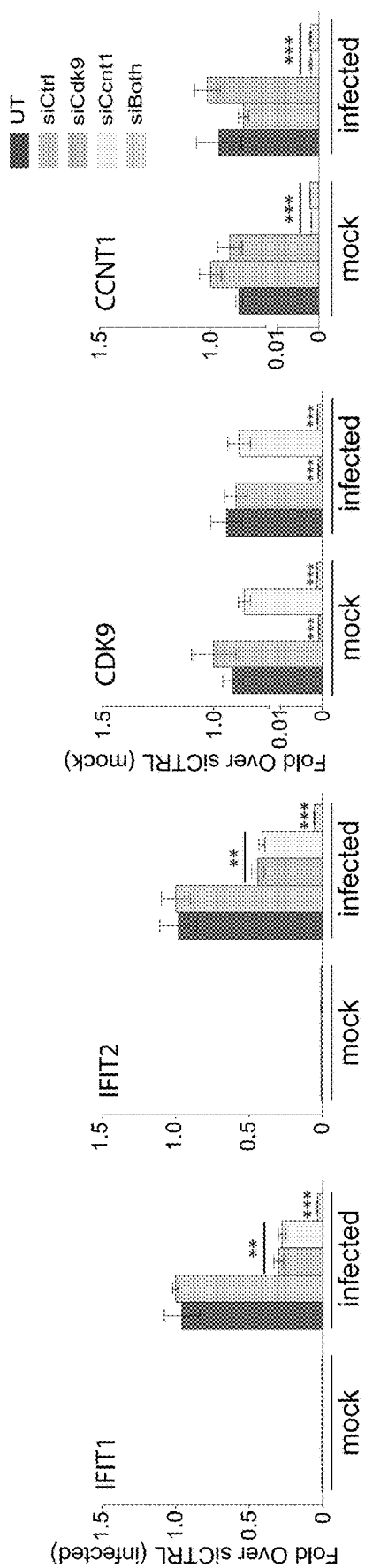
FIG. 5A-B depicts the validation of the screen hits by P-TEFb and Brd4 loss-of-function studies. (5A) IFN-β, IFIT1, CDK9 and CCNT1 mRNA expression levels in A549 cells 4 hours after mock treatment or post-infection (p.i.) with the PR8ΔNS1 virus. Cells were transfected with either individual siRNAs targeting P-TEFb complex components CDK9 (siCdk9) or CCNT1 (siCcntl) or both CDK9 and CCNT1 (siBoth). From left to right, columns represent data from untreated (UT), siCtrl, SiCdk9, siCcntl, and siBoth. (5B) IFIT1, IFIT2 and BRD4 mRNA expression levels in A549 cells treated as in (A) and transfected with siRNA targeting BRD4 gene (siBrd4). (5A, 5B) A549 cells left untransfected (UT) or transfected with non-targeting siRNA treated cells (siCtrl) are included as controls. *P<0.05, P<0.005 and *P<0.0005 (calculated with a student's t-test). Data are from three independent experiments (mean and s.d.).
Figure 5B:
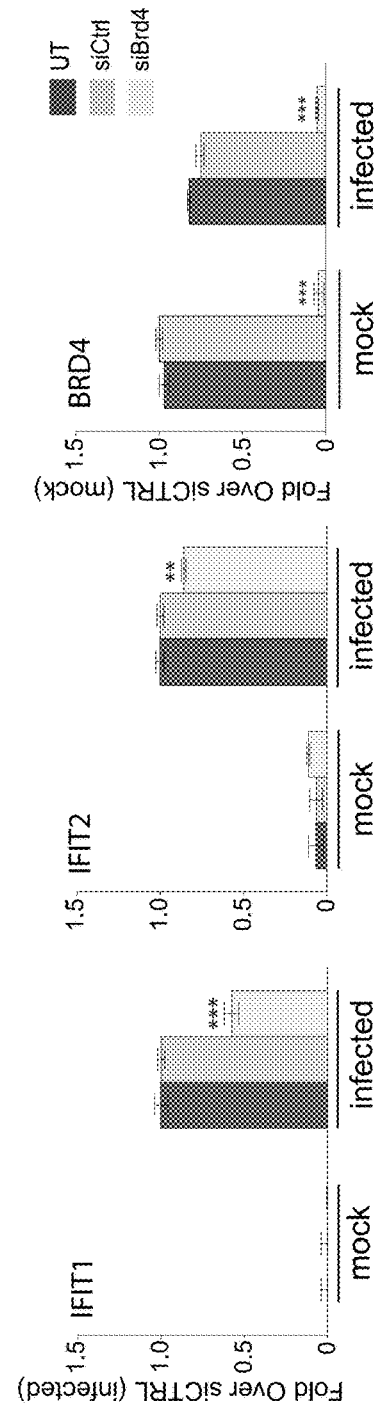

The cellular targets of FVD, (+)-JQ-1 and CPT are P-TEFb (the inhibitor of Positive Transcription Elongation Factor b), BET proteins (Bromodomain and Extra-Terminal motif), and Top1 (Topoisomerase 1), respectively(20-22). P-TEFb, BET proteins and Top1 are ubiquitously expressed, and thought to control basal transcriptional levels of many genes. However, recent studies showed that P-TEFb and BET protein inhibitors have a specific effect on genes induced by innate immune stimuli(23) and during oncogenic transformation(24), highlighting their usage in what is often referred to as epigenetic therapy(25). For this reason, the observation that FVD and (+)-JQ-1 suppress PAMP-induced genes, as well as the validation that such an effect is phenocopied by small interfering RNA (siRNA)-mediated depletion of their cellular targets (FIG. 5), was not surprising. In contrast, the pronounced impact of CPT on PAMP-induced genes was unexpected. Indeed, a previous genome-wide analysis demonstrated that Top1 inhibition suppresses the majority of long genes (>100 Kb) while inducing a fraction of smaller genes(26, 27). The inhibitory effect at long genes is believed to be caused by Top1-mediated resolution of topological constraints occurring on long templates as a result of RNAPII activity (26, 28).

Top1's activating effect is thought to be dependent on gene-specific features like topology, promoter sequence, or indirect effects(27-30). A concentration-dependent effect of the inhibitor CPT is also known, whereby high concentration and prolonged treatment leads to DNA damage(31).

Figure 1C:
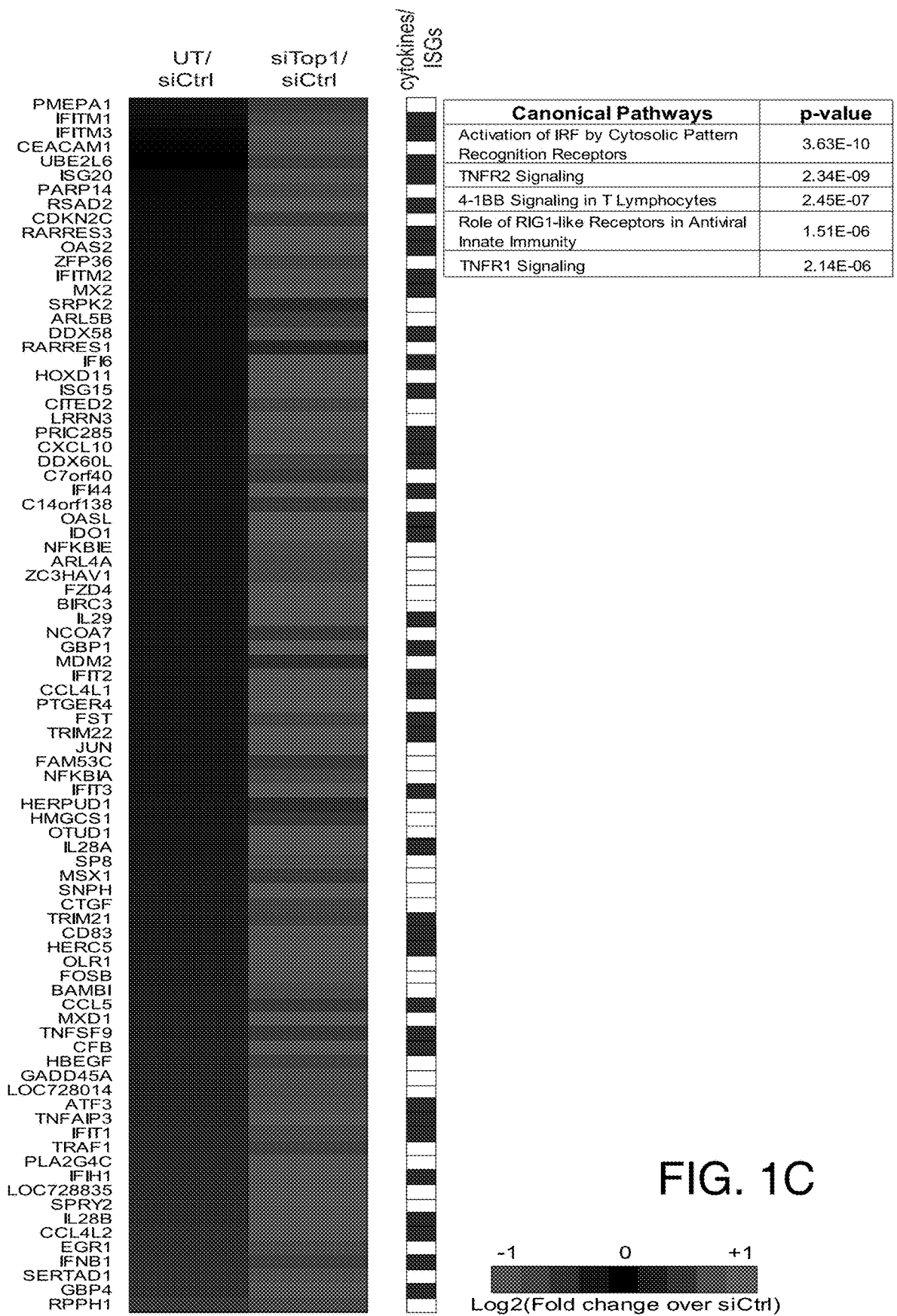
Figure 1D:
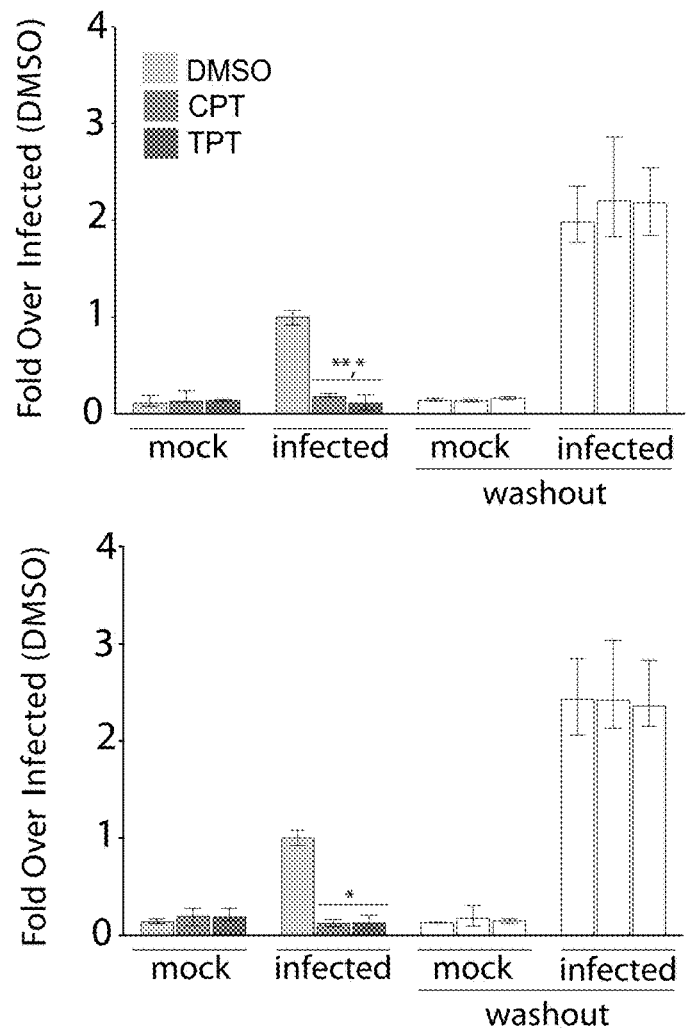
Figure 6A:
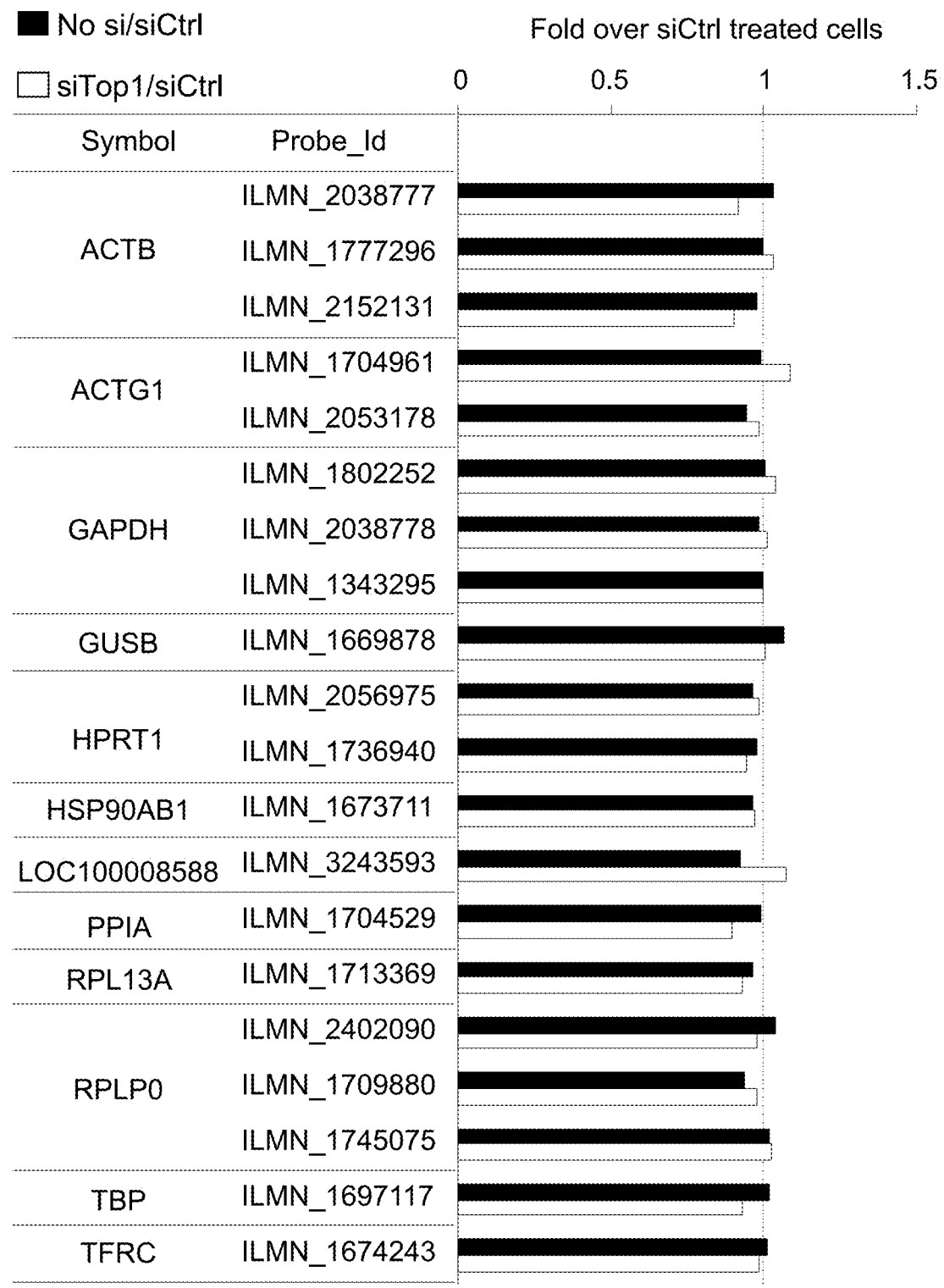
FIG. 6A-C demonstrates that reversible Top1 inhibition does not affect housekeeping gene expression or cellular damage. (6A) Expression levels of 12 housekeeping genes were determined by microarray analysis of untransfected (UT) and siTop1 or siCtrl transfected cells in absence of infection. Results for individual probe-sets are shown for genes that are represented by multiple probe-sets on the microarray. (6B, 6C) H2AX staining (light gray) in mock or PR8ΔNS1 virus infected A549 cells (6B) or H3N2 virus infected RAW 264.7 cells (6C), treated with either CPT (0.5 and 10 μM) or TPT (100 nM and 10 μM) and monitored by immunofluorescence. Nuclei (dark gray) are also shown by DAPI staining. Data are from two (6B, 6C) and three independent experiments (6A). For (6B) and (6C) representative images are shown.

To analyze the role of Top1 per se, i.e. independently of its chemical inhibition, the effect of transient Top1 depletion via siRNA was examined. Control (siCtrl) and Top1-depleted (siTop1) A549 cells were infected with influenza PR8ΔNS1virus and assessed global differences in gene expression by microarray analysis (FIG. 1C, FIG. 6A and Table 1). Upon infection, Top1 depletion significantly decreased expression of 84 genes in infected cells (as compared to the control (siCtrl)) (FIG. 1C). Remarkably, none of the downregulated genes were long but they were highly enriched for transcripts coding for inflammatory cytokines and interferon stimulated genes (ISGs) (FIG. 1C and Table 2). Importantly, the expression of housekeeping genes was unaffected independently of their level of expression (FIG. 6A) indicating that Top1 depletion does not suppress gene expression 'tout court' but predominantly affects genes induced in response to infection. Notably, these gene knockdown experiments rule out the possibility that the suppression of PAMP-induced genes is the consequence of covalent complexes or cell damage, which are known to be caused by high dosage and prolonged chemical inhibition of Top1(26). To strengthen this point, a wash-out experiment was performed in the presence and absence of Top1 inhibition. As shown in FIG. 1D, the effect of Top1 inhibition on inflammatory genes was fully reversible upon drug wash-out, indicating the absence of any permanent change or damage in treated cells.

Figure 1E:
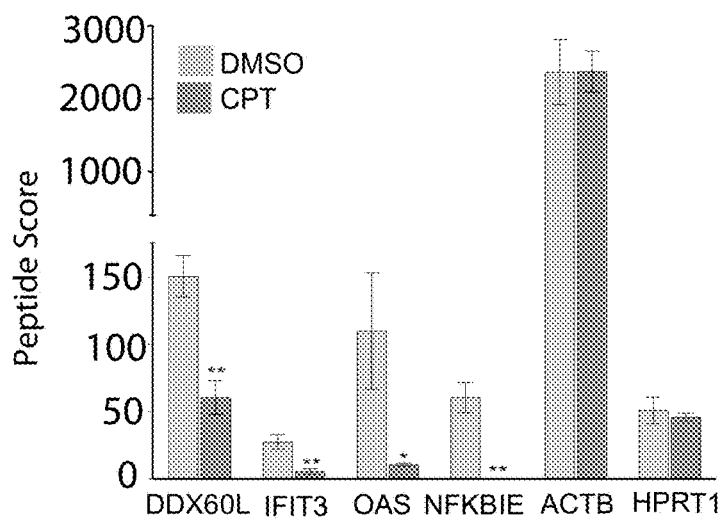

A global proteomic analysis was performed in influenza virus infected A549 cells in the presence and absence of CPT treatment. Mass spectrometry analysis indicates that the protein levels of PAMP-induced genes was compromised upon Top1 inhibition (FIG. 1E), as indicated by the representative proteins DEAD (Asp-Glu-Ala-Asp) Box Polypeptide 60-Like (DDX60L), Interferon-Induced Protein With Tetratricopeptide Repeats 3 (IFIT3), 2'-5' oligoadenylate synthetase (OAS) and NFBKIE. Importantly, the production of housekeeping proteins was unaffected independently of their expression level [(FIG. 1E, low expressed: HPRT, (hypoxanthine-guanine phosphoribosyltransferase), high expressed: ACTB (β-actin)]. Overall, these results indicate that Top1 is required to up-regulate antiviral gene expression after recognition of viral PAMPs.

Top1 Controls RNAPII Activity at PAMP-Induced Gene Loci.

Figure 2A:
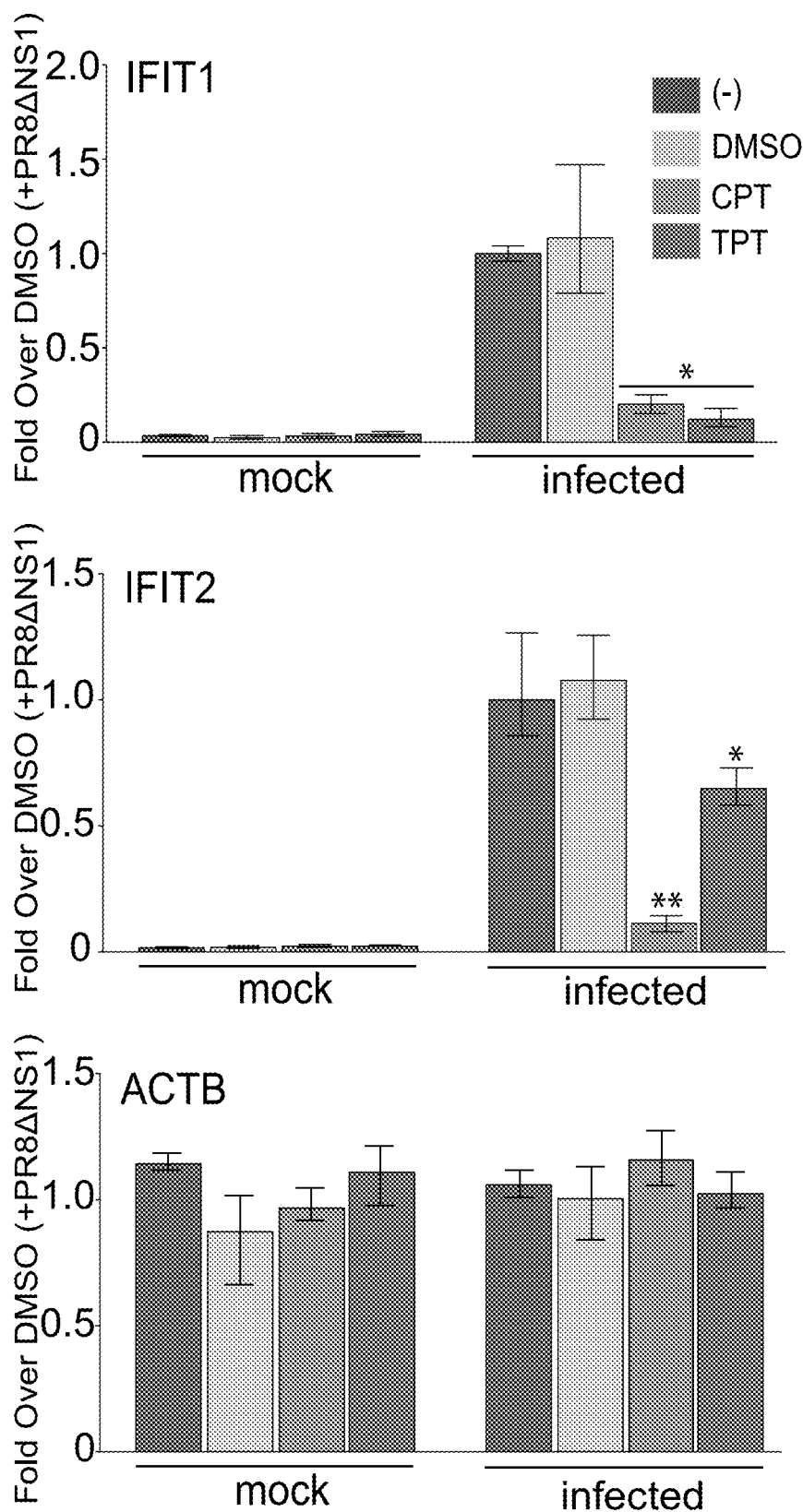
FIG. 2A-F demonstrates that Topotecan and Camptothecin suppress RNAPII at PAMP-induced genes. (2A) Gene expression in human A549 cells, left untreated (−) or treated with 0.5 μM DMSO, CPT or 100 nM TPT, assessed 4 hours after mock treatment or PR8ΔNS1 virus infection. (2B) ChIP-qPCR analysis of endogenous RNAPII and Top1 at the transcriptional start sites of IFIT1, IFIT2 and ACTB in A549 cells treated with 0.5 μM of DMSO or CPT, assessed 4 hours after mock treatment or infection with influenza PR8ΔNS1. (2C) ChIP-seq metaplot of endogenous RNAPII in A549 cells treated with DMSO (black, top line) or CPT (dark gray, lower line) 6 hours after mock treatment or PR8ΔNS1 virus infection. Plots represent RNAPII occupancy at genes showing a 2-fold upregulation in their expression after infection. (2D) Tracks of representative antiviral genes IFIT1 and IFIT2, and housekeeping genes ACTB and HPRT1 (2E) Schematic representation of the chemical synthesis of Topotecan-Alkyne (TPT-A) from TPT. (2F) Chemical-ChIP qPCR analysis of TPT-A occupancy at the transcriptional start sites of IFIT1, IFIT2 and ACTB in A549 cells treated with DMSO or 100 nM TPT-A, assessed 6 hours after mock treatment or PR8ΔNS1 infection. *P<0.05, P<0.005 and *P<0.0005 (calculated with a student's t-test). Data are from three independent experiments (2A) and from two independent experiments (2B, 2F). Mean and s.d. are indicated.
Figure 6B:
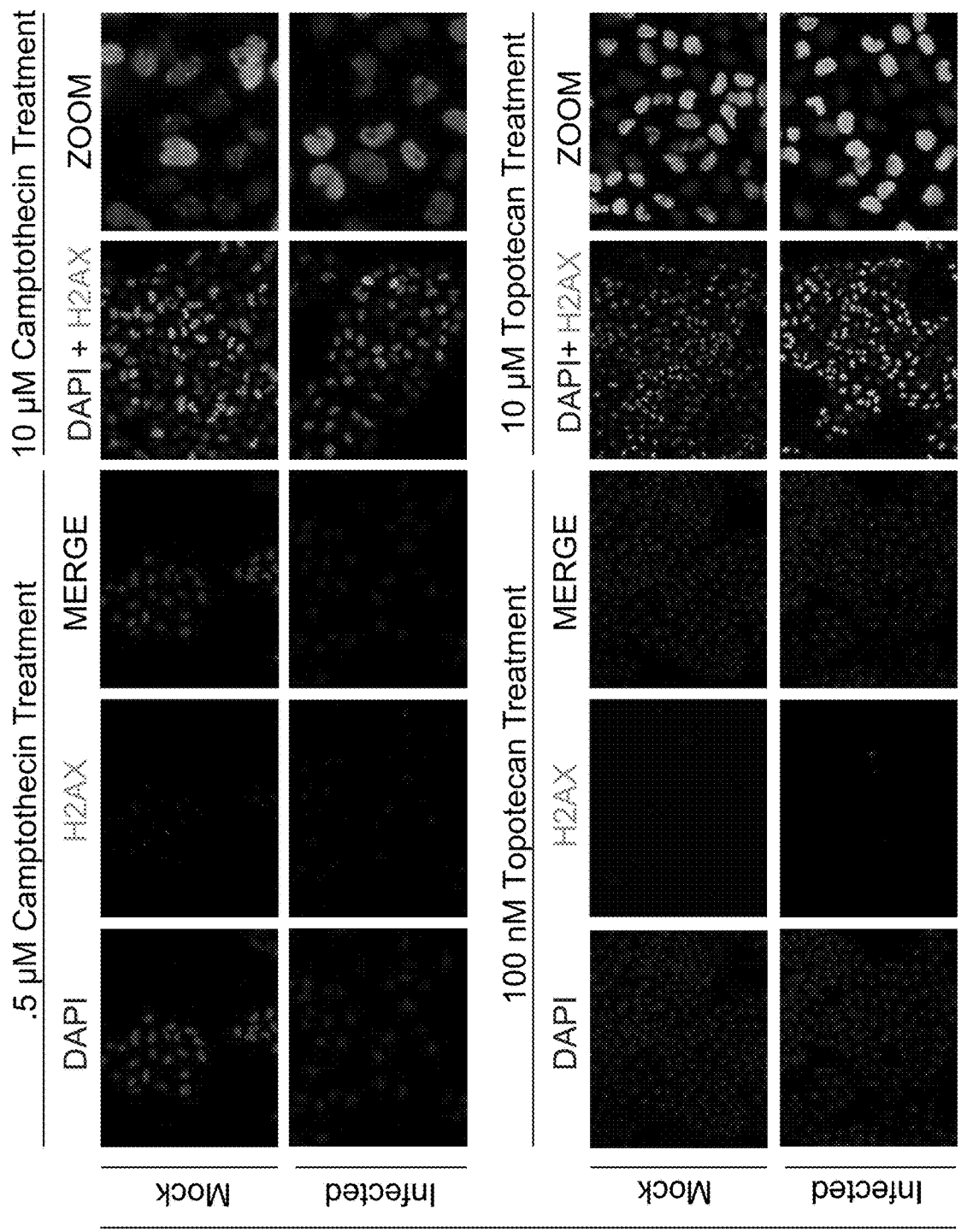
Figure 6C:
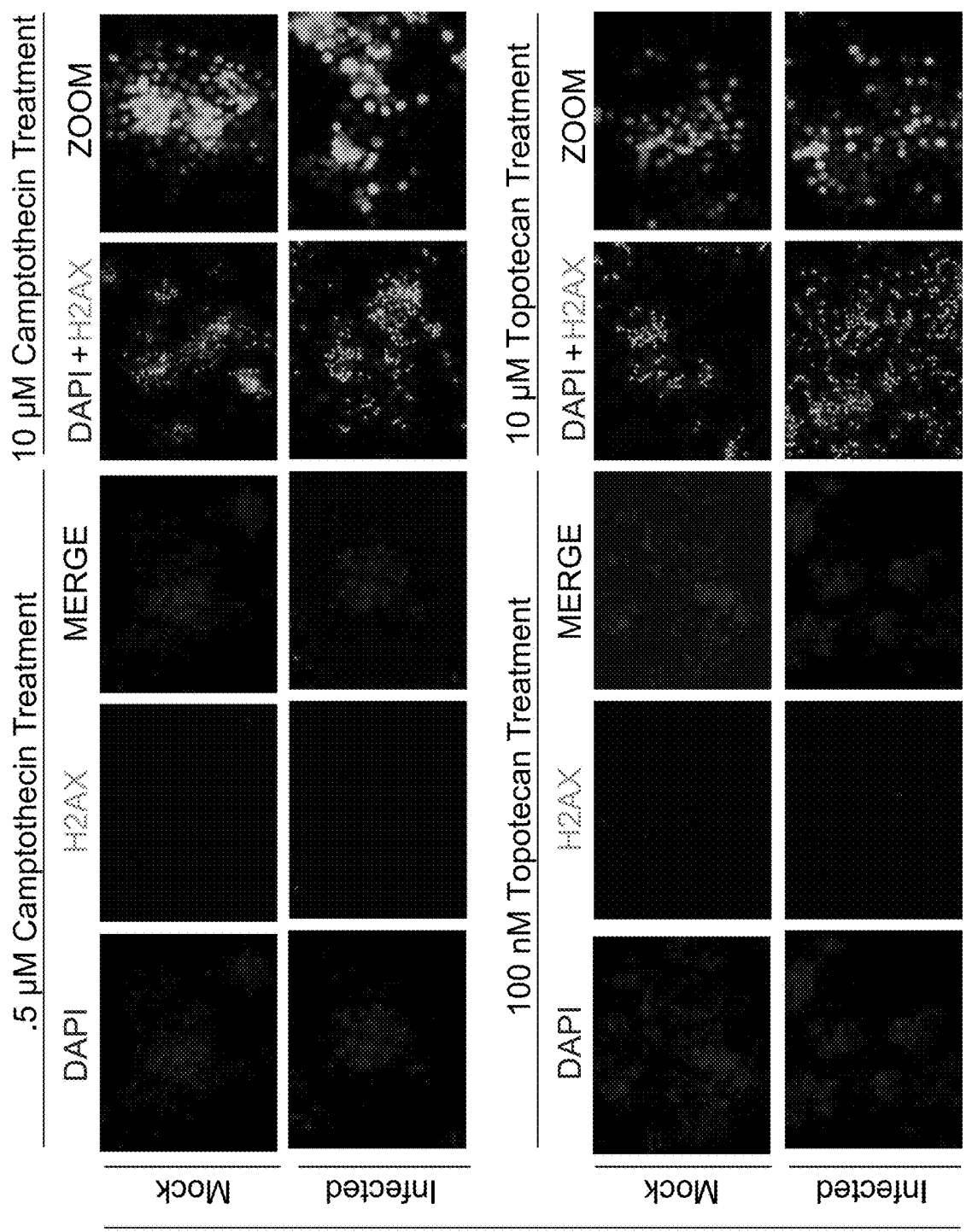
Figure 7A:
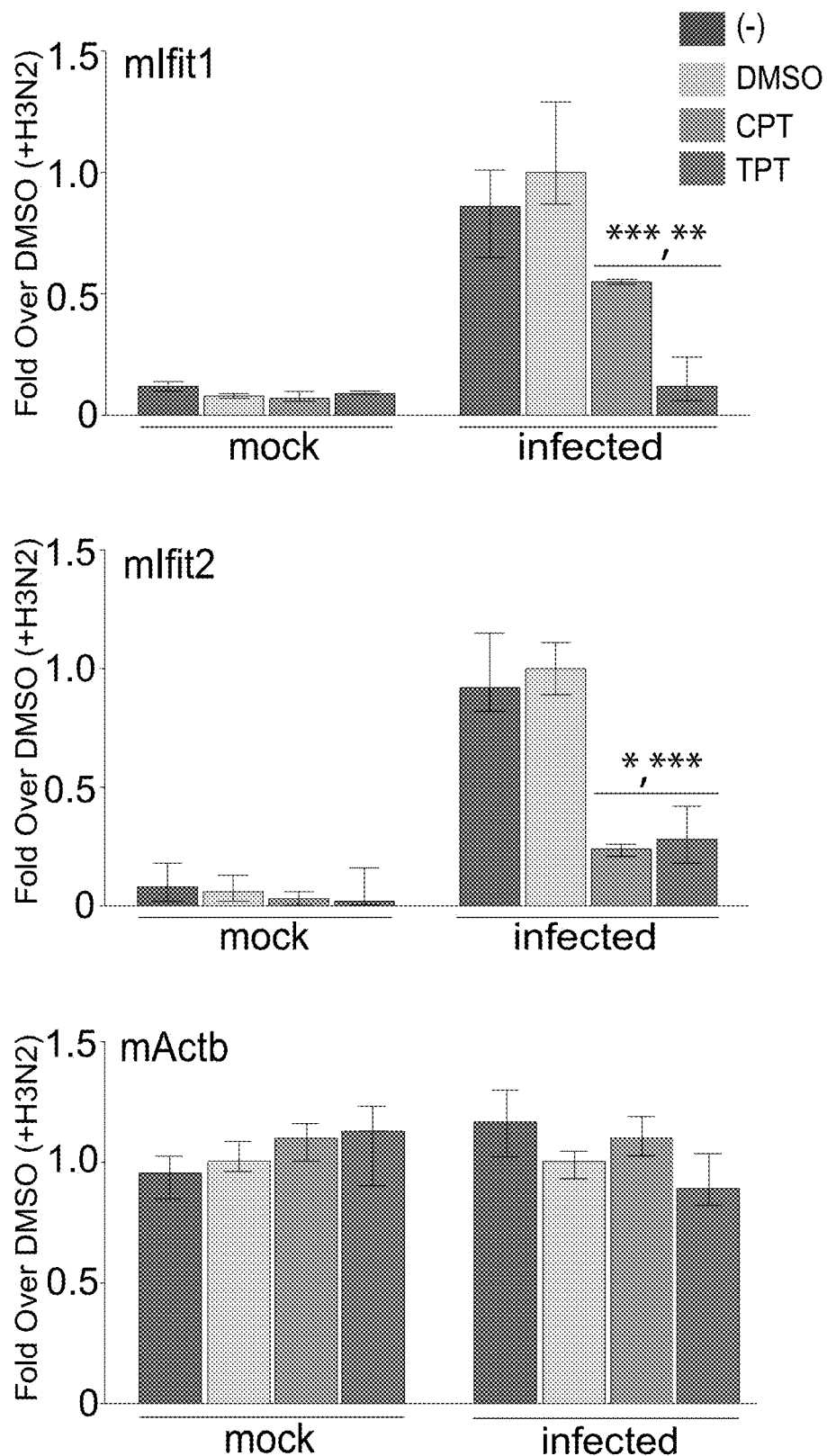
FIG. 7A-B shows Top1 inhibition in macrophages. (7A) Gene expression in murine RAW 264.7 cells left untreated (−) or treated with 0.5 μM DMSO, CPT or 100 nM TPT, assessed 4 hours after mock treatment or H3N2 virus infection. (7B) ChIP-qPCR analysis of endogenous RNAPII and Top1 at the transcriptional start sites of mIfit1, mIfit2 and mActb in RAW 264.7 cells treated with 0.5 μM of DMSO or CPT, assessed 4 hours after mock treatment or infection with a H3N2 virus. *P<0.05, P<0.005 and *P<0.0005 (calculated with a student's t-test). Data are from two (7B) or three (7A) independent experiments. Mean and s.d. are indicated.

To confirm the specificity of Top1 activity in this system, it was first investigated whether the inhibition of PAW-induced genes could be reproduced using a different Top1 inhibitor. Topotecan (TPT), a Food and Drug Administration (FDA)-approved Top1 inhibitor was therefore used. The results indicate that both CPT and TPT suppress viral PAMP responsive genes (FIG. 2A). Furthermore, parallel experiments were performed using both inhibitors in a different cell type, the murine macrophage cell line RAW 264.7. In these cells an inhibitory effect on PAMP-induced gene expression upon Top1 inhibition was also observed with both compounds (FIG. 7A). Notably, as suggested by the loss-of-function experiments, and in line with other results (26), neither TPT- nor CPT-treated cells displayed DNA damage at the concentration used (FIG. 6B, 6C). In fact, DNA damage was only detectable at the concentrations of CPT and TPT 20 and 100 times higher than those selected for these experiments, respectively. (FIG. 6B, 6C).

Figure 2B:
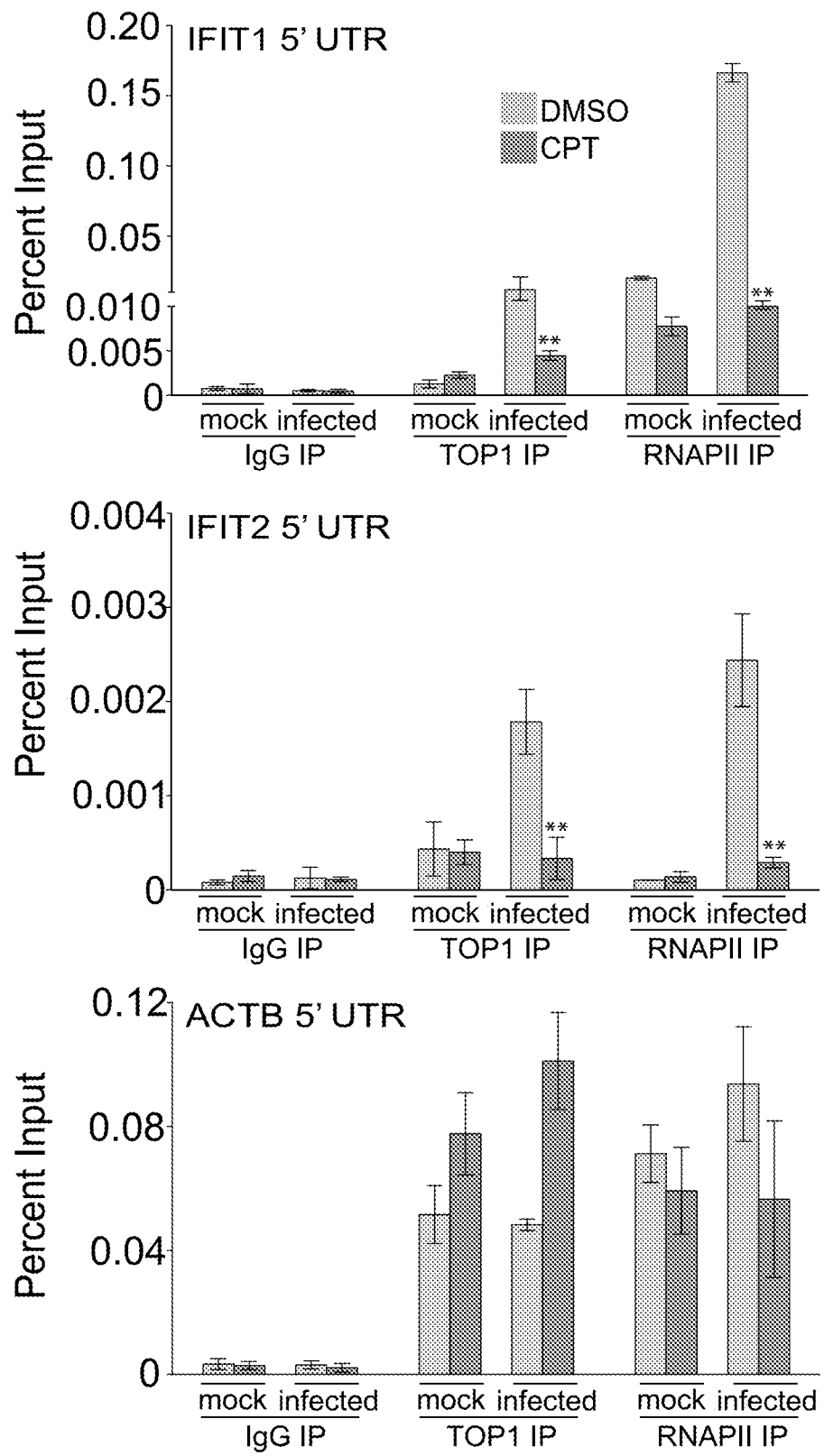
Figure 7B:
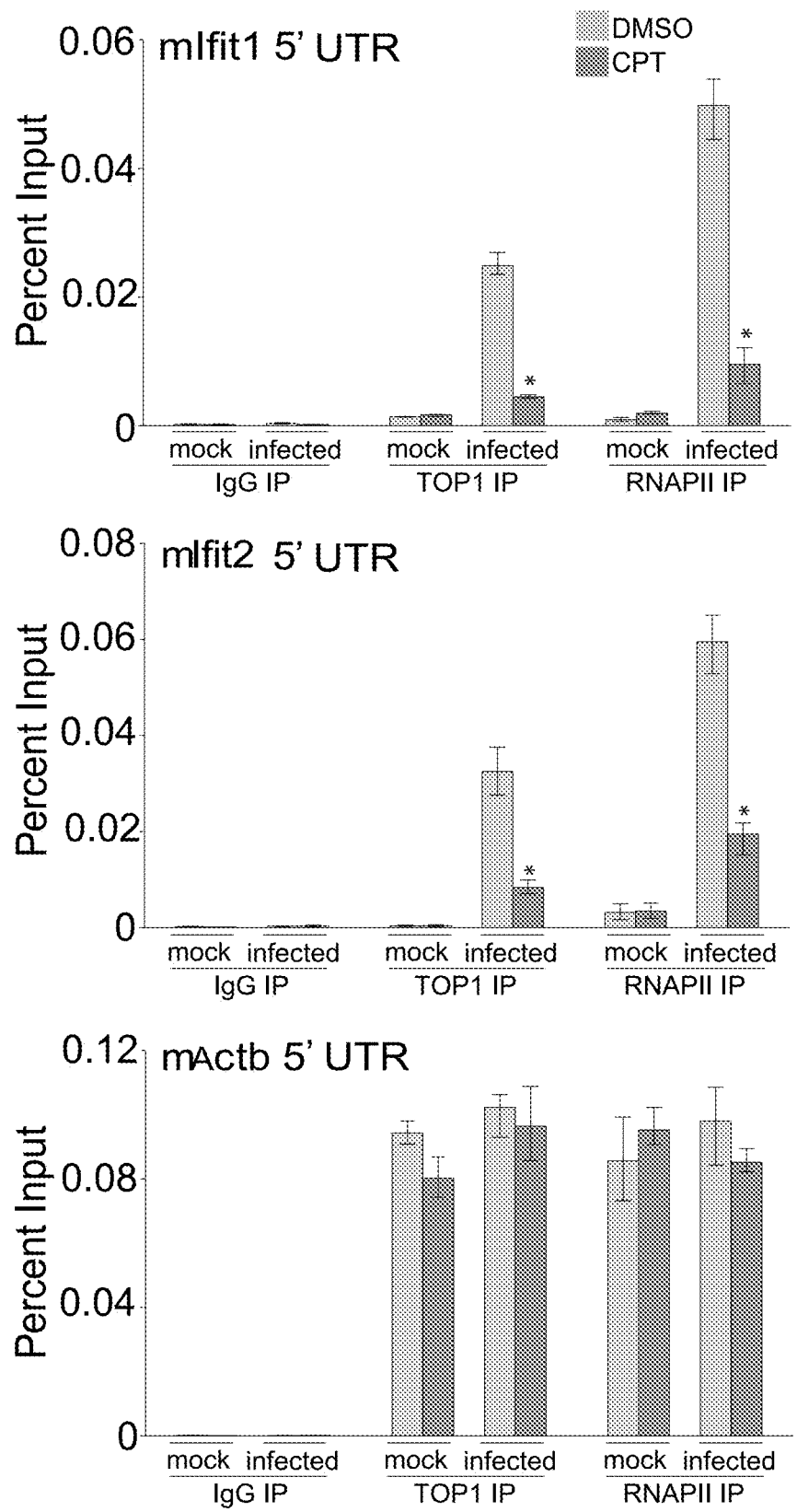

The genomic distribution of RNAPII and Top1 was characterized during infection, in the presence and absence of Top1 inhibition. The results show reduced promoter levels of RNAPII and Top1 at PAMP-induced genes in infected A549 cells (FIG. 2B) and macrophages (FIG. 7B) when Top1 is inhibited. Notably, RNAPII and Top1 levels at housekeepers are not reduced as a result of Top1 inhibition (FIG. 2B, FIG. 7B), consistent with their unaffected gene expression (FIG. 2A and FIG. 7A).

Figure 2C:
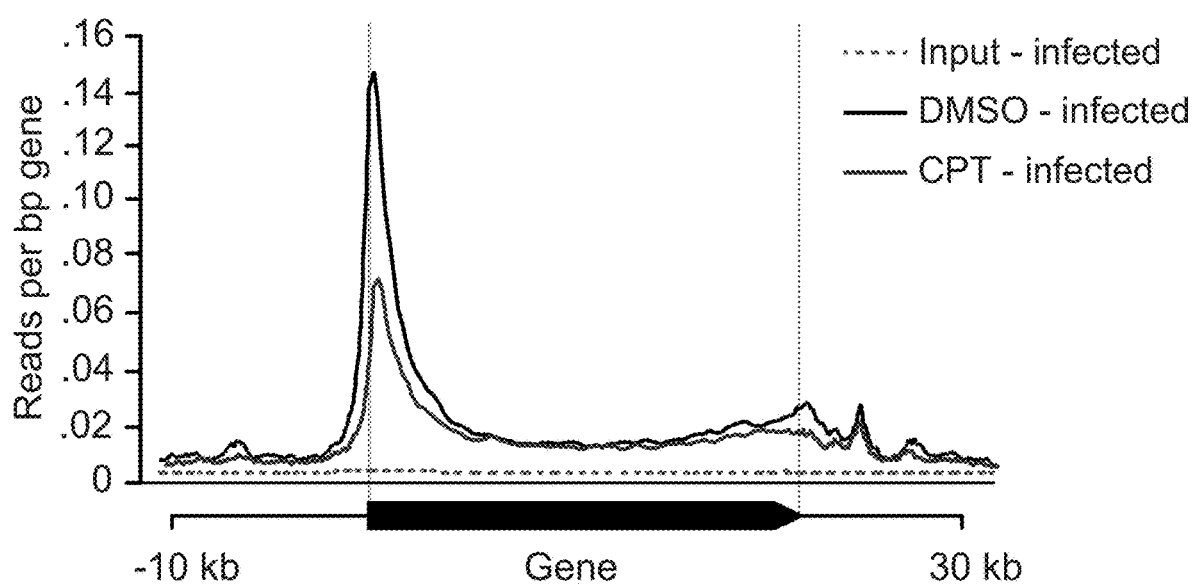
Figure 2D:
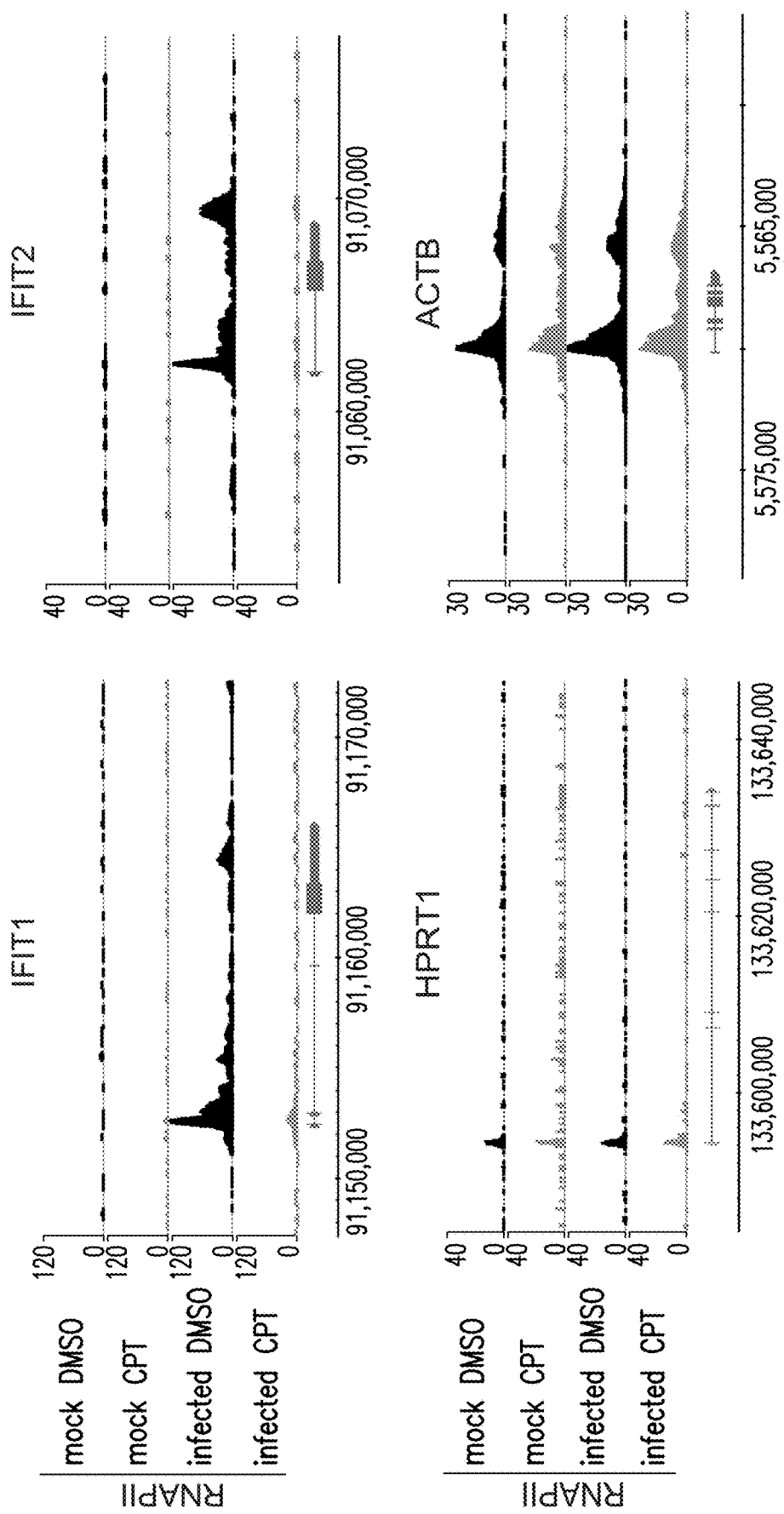
Figure 2E:
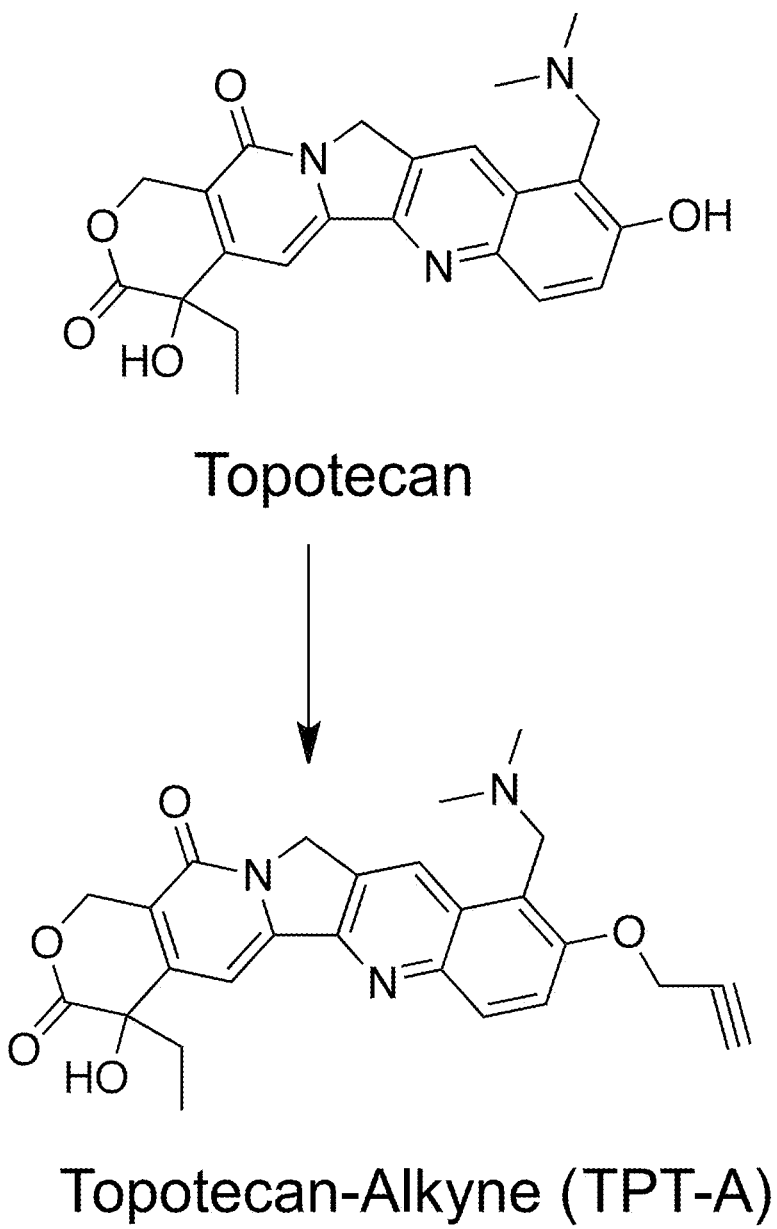

Reduced RNAPII targeting at PAMP-induced loci was confirmed by ChIP-sequencing (FIG. 2C) and by the analysis of the RNAPII tracks at representative PAMP-induced genes and housekeepers (FIG. 2D). To link cause (Top1 inhibition) and effect (RNAPII levels at promoters), a novel strategy was devised to map the genomic distribution of Top1 inhibitors via chem-ChIP, a method used to reveal the genomic localization of drugs (32). In brief, the inventors first 'in house' synthesized an analog of TPT (we did not succeed with CPT), which is amenable for coupling with a derivative of biotin. This compound was called TPT alkyne [(TPT-A; FIG. 2E). TPT-A purification and the experimental strategy are shown in FIG. 8A; the validation that TPT-A is as effective as TPT is shown in FIG. 8B, 8C. Chem-ChIP was then performed and analyzed the distribution of TPT-A on chromatin. TPT-A was enriched at promoter regions of active genes (FIG. 2F), as expected based on the genome-wide distribution of Top1 (28, 33).

Figure 2F:
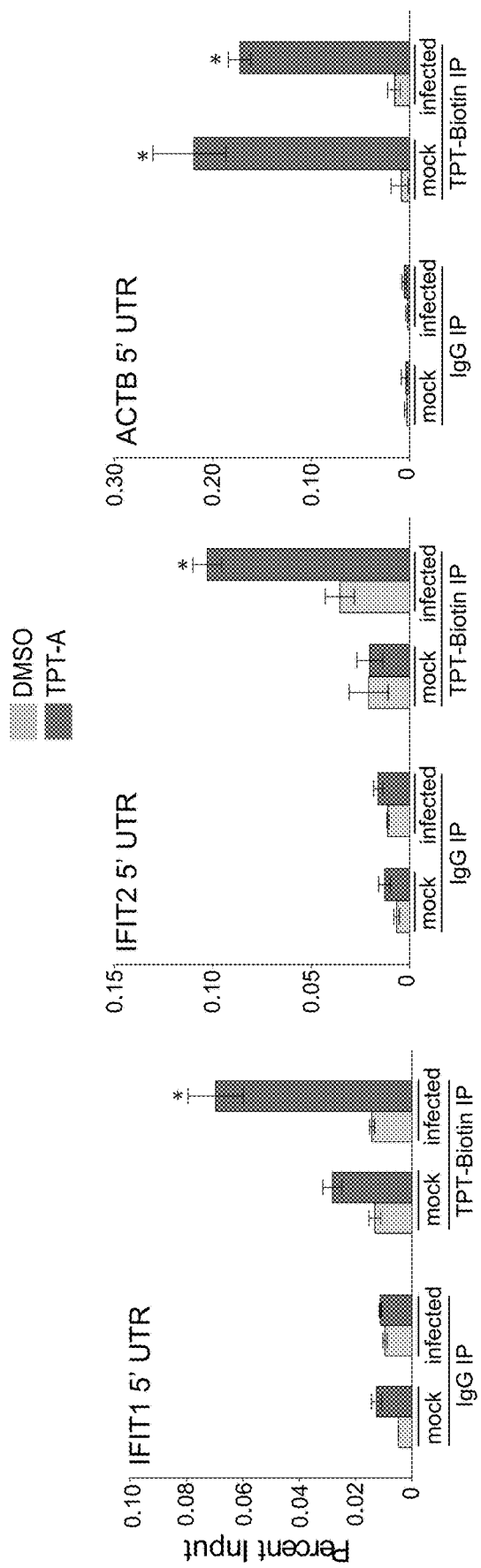

Strikingly, TPT-A distribution is inversely correlated with RNAPII and Top1 density only at promoters of PAMP-induced genes and indicates that TPT-A suppression of Top1 activity leads to a specific inhibition of RNAPII targeting at PAMP-responsive loci (FIG. 2F). These results i) corroborate the absence of an effect of Top1 inhibition at housekeepers, ii) indicate that such genes can escape the transcriptional consequences of Top1 inhibition, and iii) designate an RNAPII activator-like function for Top1 at PAMP-induced loci.

Top1 Inhibition Suppresses the Response to Bacterial Stimuli and Pro-Inflammatory Cytokines.

Figure 3A:
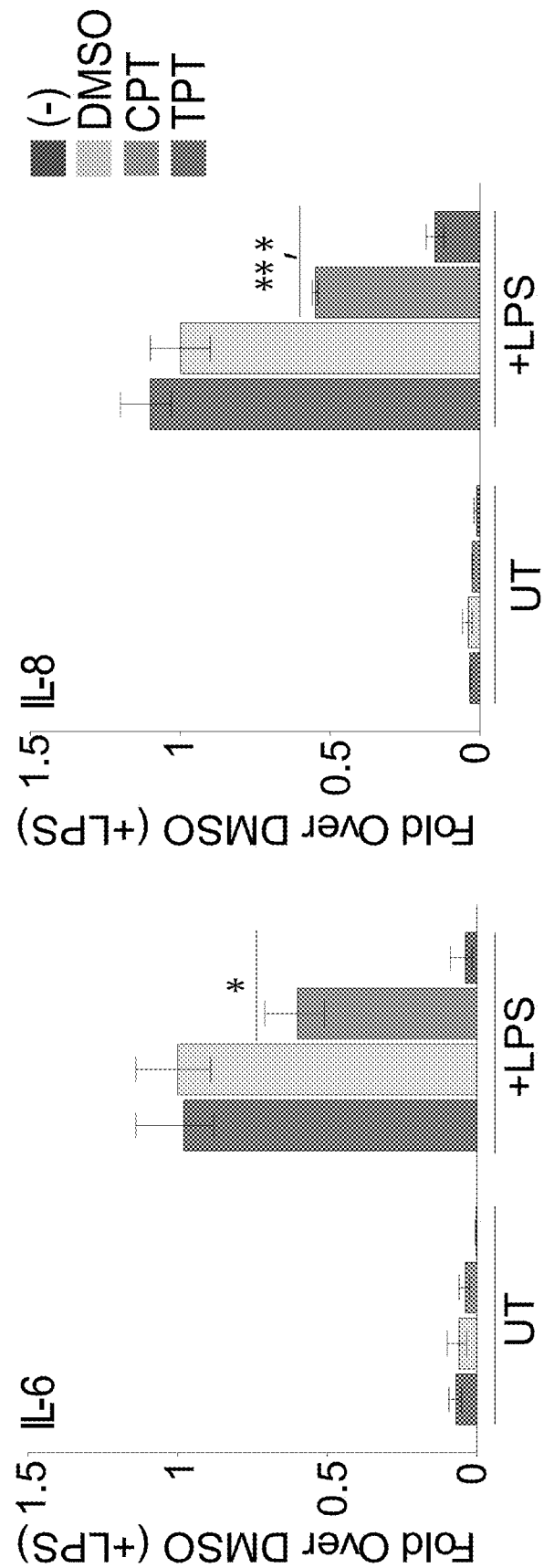
Figure 3B:
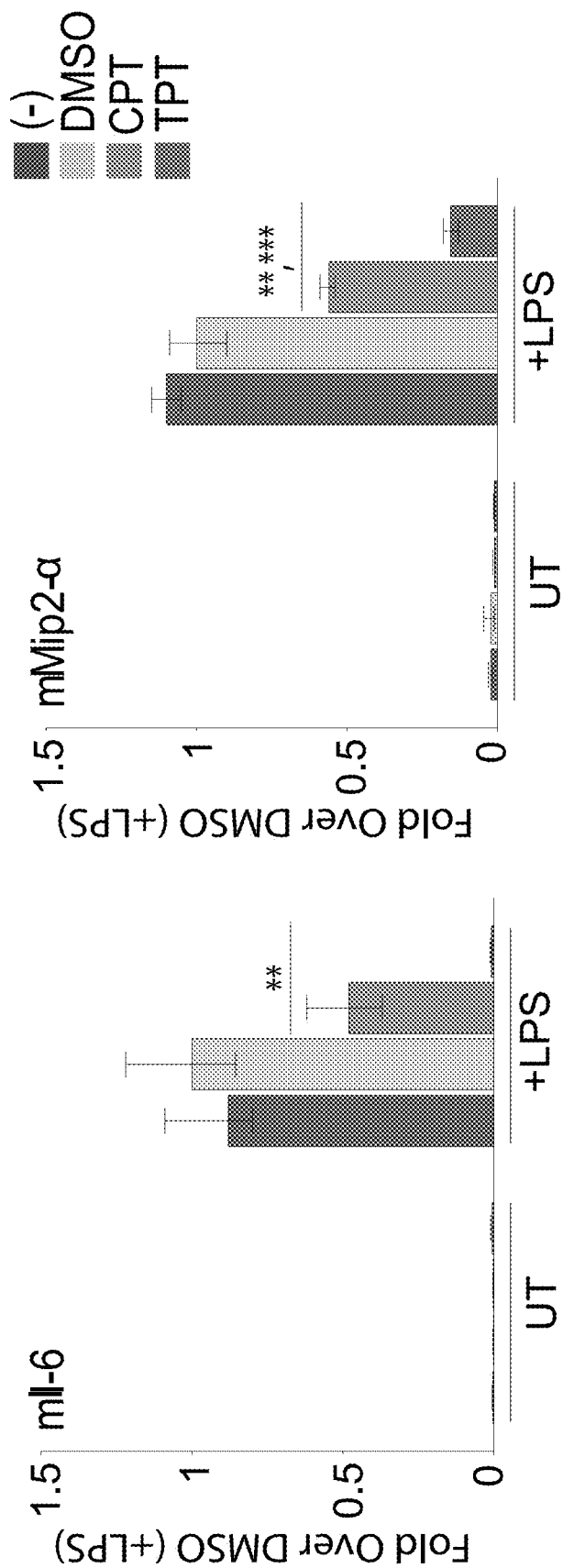

To understand whether Top1 is required to activate the expression of pro-inflammatory genes induced by stimuli other than viruses, the effect of Top1 inhibition after exposure to bacterial PAMPs and exogenous cytokines was characterized. First, both epithelial and macrophage cell lines were treated with the bacterial-PAMP lipopolysaccharide (LPS). Top1 inhibition suppressed the expression of anti-microbial genes, as indicated by the transcriptional analysis of the representative pro-inflammatory cytokines interleukin (IL)-6 and IL-8 in A549 cells (FIG. 3A) and IL-6 and macrophage inflammatory protein 2-alpha (Mip2-alpha) in RAW cells (FIG. 3B). Accordingly, Top1 inhibition resulted in reduced levels of Top1 and RNAPII at promoters of the affected genes (FIG. 9A, 9B).

The expression of anti-microbial genes upon PRR stimulation induces the secretion of proinflammatory signals, which trigger the maturation and activation of other innate immune cells expressing the corresponding receptors(34). To further extend the findings on cells activated via stimulation by inflammatory cytokines, both A549 and RAW cells were incubated with exogenous IFN-β and tumor necrosis factor-α (TNFα). Gene expression changes, as well as promoter levels of RNAPII and Top1, were monitored in untreated and Top1-inhibited cells. As shown by the expression of multiple target genes (FIG. 10A, 10B) and respective chromatin occupancies (FIG. 10C, 10D), repression of Top1 activity inhibited IFN-β- and TNFα-induced gene expression in both cell types analyzed, paralleling the results using viral and bacterial stimuli.

Top1 Protects Against Exacerbated Inflammation.

Figure 3C:
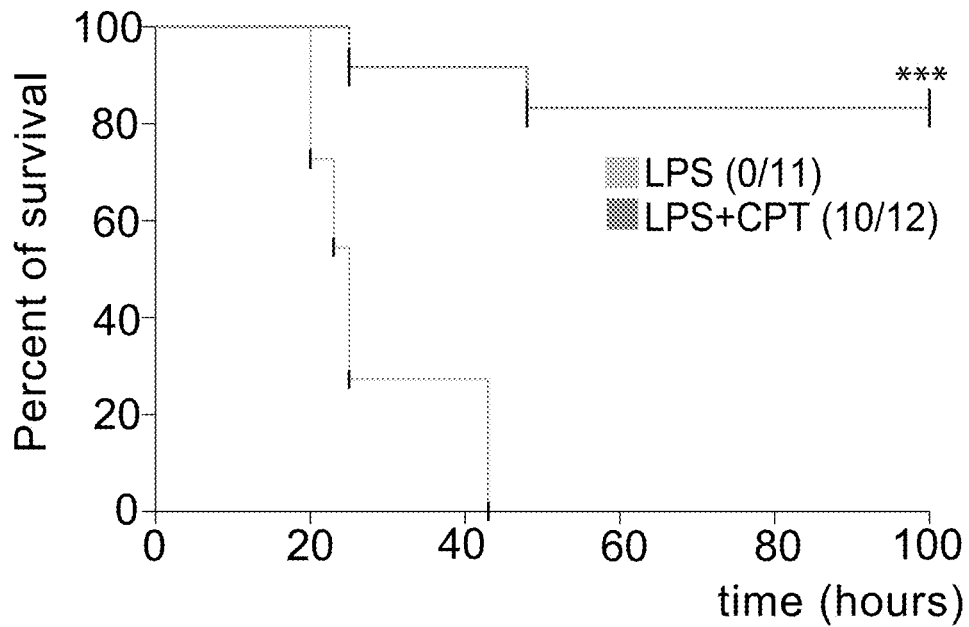
Figure 3D:
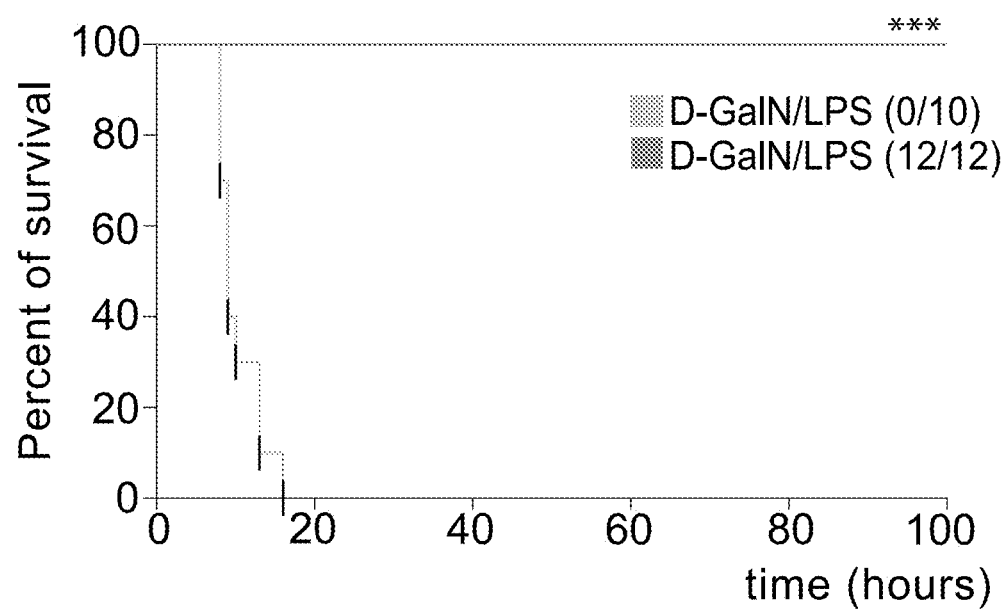
Figure 3E:
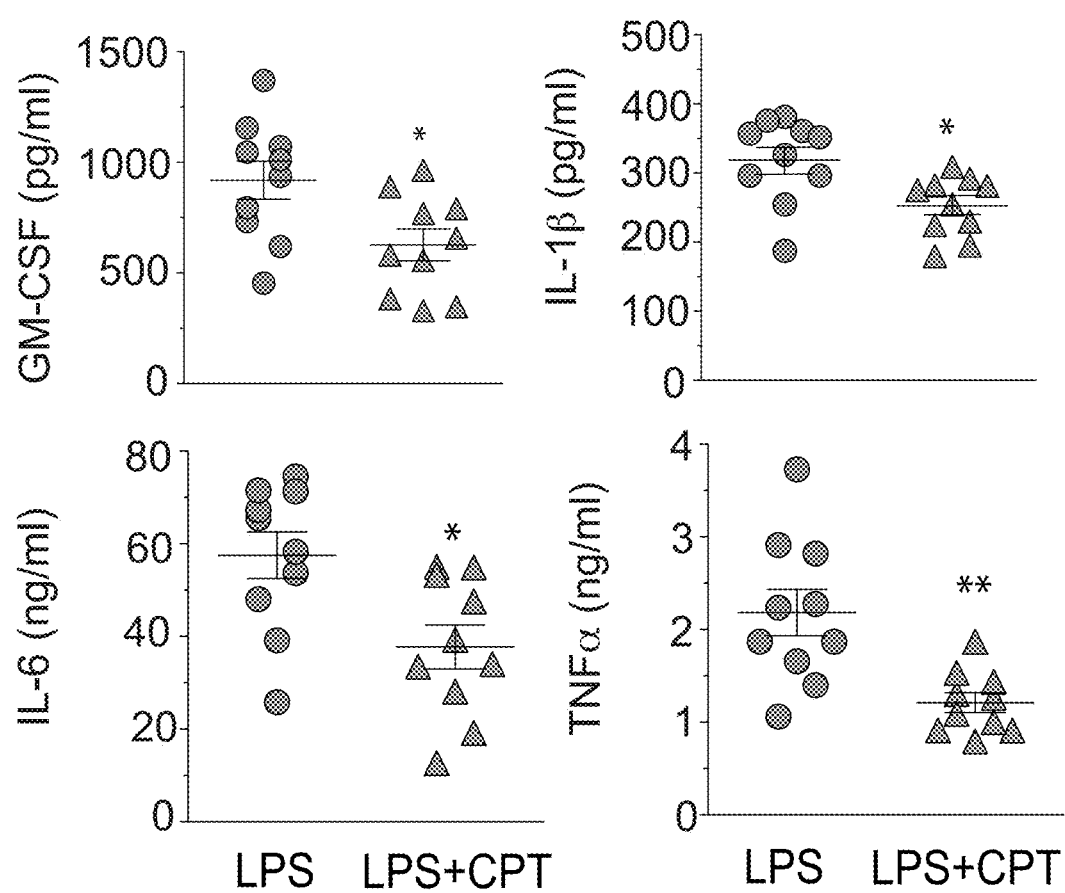
Figure 3F:
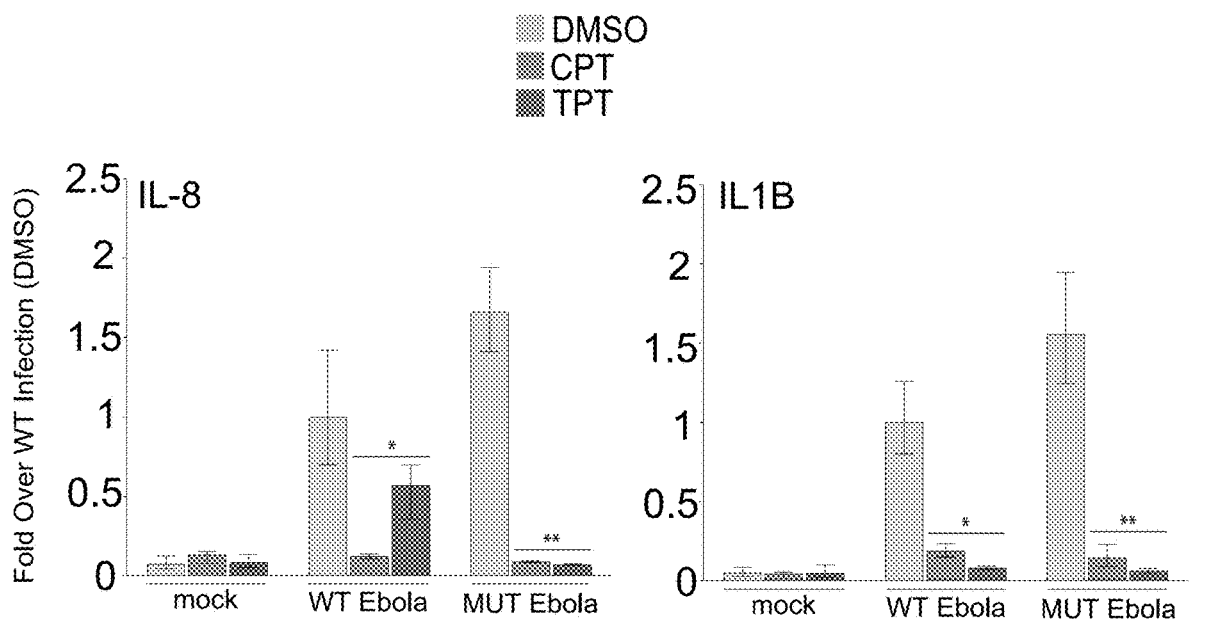
Figure 11A:
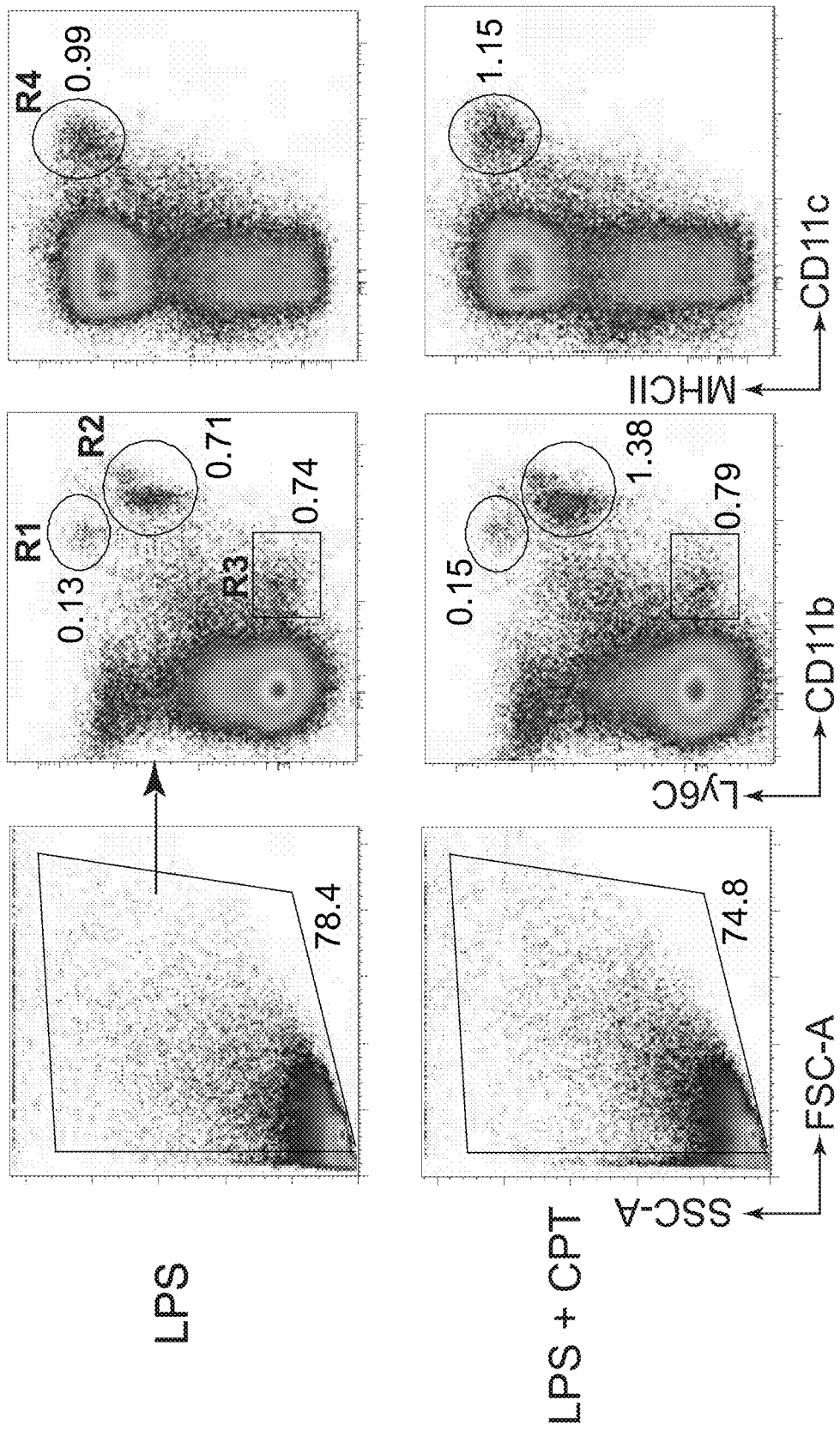
Figure 11B:
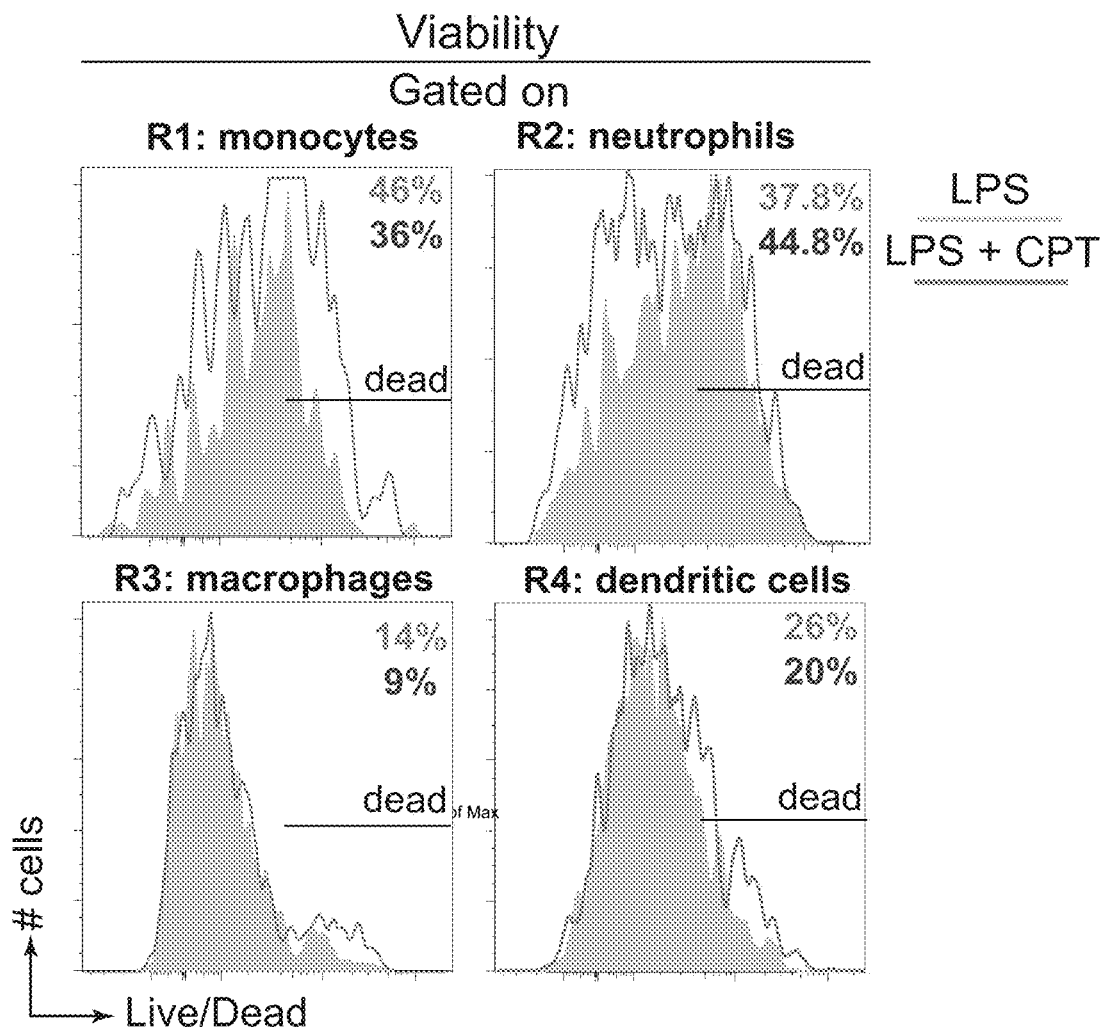
Figure 11C:
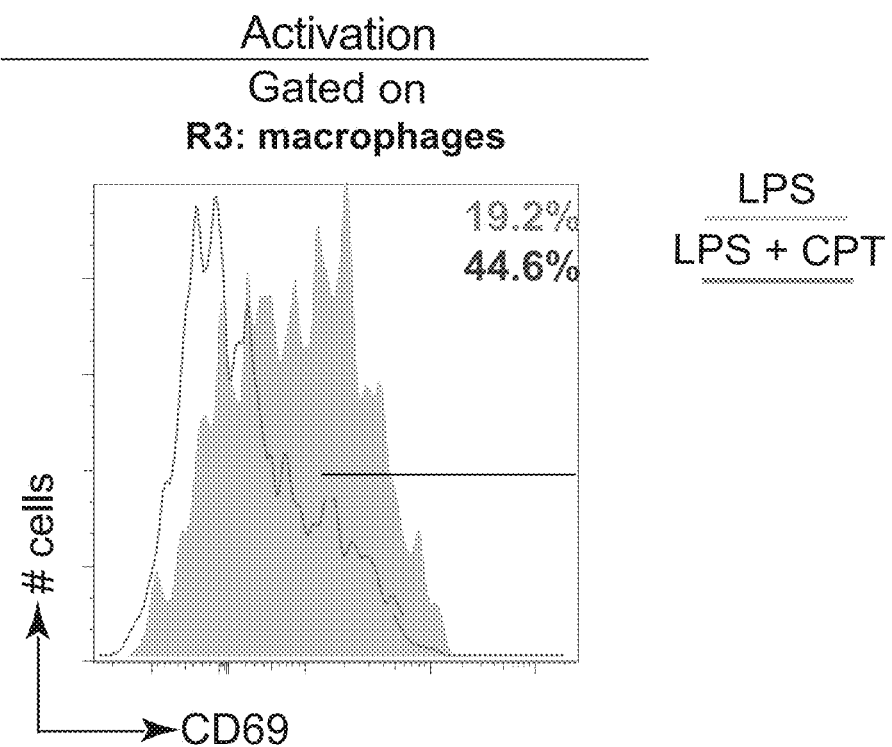
Figure 11D:
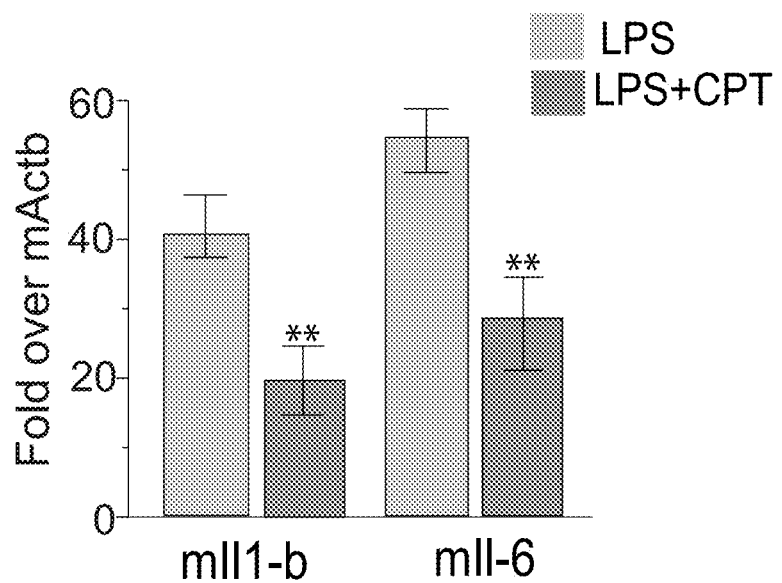

Altogether, this data suggested that Top1 inhibition could be an effective way to suppress the exacerbated response to pathogenic stimuli, and prompted the characterization of the role of Top1 inhibition in vivo. As indicated in FIG. 3C, in vivo inhibition of Top1 activity rescued animals from lethal endotoxic shock. This effect was not caused by cellular damage (FIG. 11A-11C). In contrast, analysis of pro-inflammatory genes and cytokine expression in both untreated and CPT-treated animals indicate that the protective effect of Top1 inhibition in vivo is a consequence of their suppression (FIG. 3E and FIG. 11D). Strikingly, a similar protective effect is also present when inhibiting Top1 in an endotoxininduced mouse model of acute liver-failure, where the pathology is caused by high levels of cytokine secretion such as TNFα (FIG. 3D)(35). Finally, since an elevated mortality rate associated with an exacerbated pro-inflammatory response and clinical symptoms similar to septic shock is also observed in humans after infection with highly pathogenic viruses, the next disease focused on was Zaire ebolavirus (Ebola virus), which recently caused a large outbreak of illness with a high fatality rate in West Africa (36). The global gene expression response was profiled during Ebola (WT strain Zaire-Mayinga) infection in the human leukemic cell line THP-1 in the presence and absence of Top1 inhibition. The analysis shows that Ebola virus-induced genes IL-6 and IL-1B are suppressed by Top1 inhibition (FIG. 3F and Table 3). Overall, these data highlight a protective role for Top1 inhibition during infections both in vitro and in vivo.

Discussion

Topoisomerase activities are required at all genes in order to resolve topological constrains that result from RNAPII activity. Recent work (26, 27) has shown that short and reversible Top1 inhibition specifically suppresses the expression of long genes. This indicated a differential susceptibility of genes to Top1 inhibition and redundant Top1 activities at the promoters of housekeepers. The above examples demonstrate the surprising evidence that during infection, short and reversible inhibition of Top1, as well as Top1 depletion, specifically suppresses genes induced by microbial agents and other agents that result in an exacerbated immune response. These results reveal a novel gene specific activator-like role for Top1. Concordantly, such an effect was shown using in vitro transcriptional assays (29, 30). The consequence of Top1 inhibition during such immune response is a suppression of promoter recruitment of Top1 and RNAPII at PAMP-induced loci. This effect is likely caused by the presence of the inhibitor that creates a local chromatin environment non-permissive to transcription. Alternatively, Top1 inhibitors could titrate out new recruitment of Top1. Both scenarios would lead to defects in RNAPII recycling and re-initiation and cause the observed suppressive effects at pathogen-induced genes and/or genes involved in cytokine storms including inflammatory genes. Since Top1 facilitates the expression of such inflammatory genes, Top1 depletion or chemical inhibition during infection reduces the immune response associated with pathogen recognition and can also reduce an exacerbated immune response caused by a disease, condition, disorder, state or infection that results in such a cytokine storm. This effect was evident in vitro by chemical inhibition of Top1 causing suppression of both virus- and inflammatory signal-induced host gene expression, and in vivo by displaying a complete protective effect in mouse models of septic shock and liver failure. The cell response against microbes and other pathogens is essential in protecting against infection, but its hyper-activation can have fatal consequences. The above results suggest that Top1-inhibition therapy could be useful in many instances where an overt immune response is elicited.

Materials and Methods

Cell Lines and Viruses

The following cell lines were originally obtained from the American Type Culture Collection: A549 cells (adenocarcinomic human alveolar basal epithelial cells), 293T cells (human embryonic kidney cells), and RAW 264.7 cells (mouse leukemic monocyte macrophage cell line). The 293T-FF cell line was generated by transfection with the plasmid pGL4.17-IFN-FF, encoding a cassette with the firefly luciferase gene under the control of the murine IFN-β promoter, as previously described(37), and was a kind gift from P. Palese. Cells were maintained in culture at 37° C. with 5% CO2 in Dulbecco's minimal essential medium (DMEM, Gibco, Life Technologies) supplemented with 2 mM glutamine (Life Technologies), 10% FBS (Hyclone), 100 U/ml penicillin (Life technologies) and 100 m/ml streptomycin (Gibco, Life Technologies).

The influenza virus PR8ΔNS1, which is the H1N1 PR8 A/Puerto Rico/8/1934 strain lacking the expression of the NS1 protein, was propagated in MDCK cells expressing the viral nonstructural protein 1 (NS1)(38). The PR8ΔNS1 virus and MDCK cells were both a kind gift from A. García-Sastre. The influenza virus H3N2, which is the strain A/Philippines/2/82, was propagated in 10-day-old embryonated chicken eggs and was a kind gift from F. Kramer.

Sendai virus (SeV), Cantell strain, was propagated in 10-day old embryonated chicken eggs(39).

All viral infections using the strains described above were performed at a multiplicity of infection (MOI) of 3 and cells were analyzed at different time points as indicated in the figures.

Infections with the Ebola virus were performed in the THP1 cell line, derived from THP-1, a human monocytic cell line that naturally expresses many pattern-recognition receptors. The wild-type Ebola Zaire-Mayinga strain and its VP-35 mutant, which fails to block the type I Interferon response in the host, were used (40). Cells were recovered 24 hours after Ebola infection.

Cell Viability Assay

The Cell Titer Glo Cell Viability Assay (Promega) was used to detect adenosine triphosphate (ATP) levels as a function of cell viability, according to manufacturer's specifications. Briefly, cells were seeded into 96-well plates (5000 cells/well). Eighteen hours later, 25 µL of fresh media containing the indicated compounds (serially diluted) were included. After 20 hours of incubation, 50 µL of CellTiter-Glo was added and the luminescence was measured. Vehicle treated cells were used to normalize (100%) the ATP activity.

Inhibitors and Cell Treatments

For cell culture: Camptothecin (CPT, Sigma) was dissolved in a 4:1 mixture of chloroform:methanol at the concentration of 0.5 mM, heated at 55° C. until fully dissolved and then added to cells in DMEM medium at the final concentration of 0.5 µM. Topotecan (TPT, Sigma) and TPT-Alkyne (TPT-A) were dissolved in dimethyl sulfoxide (DMSO, Fisher) at the concentration of 100 µM and then added to cells in DMEM medium at the final concentration of 100 nM. Flavopiridol and (+/−)-JQ1 (both from Sigma) were dissolved in DMSO at the concentration of 0.5 mM and then added to cells in DMEM medium at the final concentration of 0.5 µM. For all in vitro experiments, cells were treated with DMSO (as a control), CPT, Flavopiridol, (+/−)-JQ1, or TPT one hour before and one hour after stimulation.

Lipopolysaccharide (LPS, Sigma, L3012) was added to cells in DMEM medium at the final concentration of 100 ng/mL for two hours. TNFα (Sigma, human: T6674 and mouse: T7539) and Interferon-β (IFN-β, PBL Assay Science, human: 11415-1 and mouse: 12400-1) were added to cells in DMEM medium at the final concentration of 10 ng/mL and 100 U/mL respectively, for 4 hours.

For in vivo experiments: CPT was dissolved in a 4:1 mixture of chloroform:methanol, followed by heating at 55° C. until fully dissolved. CPT was then brought up with water to the necessary volume corresponding to 200 µl/mouse and centrifuged for 5 minutes at 4,000 rpm. The top aqueous fraction, containing the CPT, was recovered and dissolved at the final concentration of 30 mg/kg of mouse weight in 200 μl of water for each injection.

Immunofluorescence

A549 and RAW 264.7 cells were cultured on coverslips overnight and then pre-treated for 1 hour with 0.5 and 10 μM for CPT or 100 nM and 10 μM for TPT, infected with PR8ΔNS1 or H3N2 virus, and then re-treated with the same inhibitors 1 hour post-infection (p.i.). At 6 hours p.i., cells were fixed for 10 minutes at 4° C. in 4% formaldehyde (EMS). Coverslips were washed in PBS (Life Technologies) and cells were permeabilized for 10 minutes at room temperature in 0.5% NP-40 (Sigma). Coverslips were washed again in PBS and nonspecific binding was blocked by incubation for 30 minutes at room temperature with a solution containing 3% BSA (Sigma) in PBS. Cells were then probed for 2 hours with a rabbit anti-phospho-histone H2A.X antibody (dilution 1:200, 2577S, Cell Signaling), followed by detection with Alexa Fluor 488-conjugated (green) goat anti-rabbit IgG (heavy and light chain, A-11034, Life Technologies). DNA was counterstained with 4,6-diamidino-2-phenylindole (DAPI, Thermo Scientific).

Quantitative PCR

For RNA extraction, cells were homogenized with QIAshredder columns (79656; Qiagen). RNA was extracted using a RNeasy Mini Kit (74106; Qiagen) and then treated with a RNase free DNase kit (Qiagen). Proteins were also simultaneously recovered from cell lysates by acetone precipitation of the flow-through from RNeasy spin columns, according to manufacturer's instructions (Qiagen). cDNA was in vitro transcribed using a High-Capacity cDNA RT Kit (4368814; Thermo Fisher Scientific) or a SuperScript III First-Strand Synthesis SuperMix (18080-400; Life Technologies). Quantitative PCR (qPCR) was performed using the iTaq™ Universal SYBR® Green One-Step Kit (Bio-Rad), according to manufacturer's instructions.

Primers

Sequences of primers used for quantitative RT-PCR were as follows.

```
Human.
β-actin forward,
                                  (SEQ ID NO: 1)
5'-ACCTTCTACAATGAGCTGCG-3',
and β-actin reverse,
                                  (SEQ ID NO: 2)
5'-CCTGGATAGCAACGTACATGG-3';, GAPDH forward
                                  (SEQ ID NO: 3)
5'-GCAAATTCCATGGCACCGT-3',
and GAPDH reverse,
                                  (SEQ ID NO: 4)
5'-GCCCCACTTGATTTTGGAGG-3';

18S forward,
                                  (SEQ ID NO: 5)
5'-GTAACCCGTTGAACCCCATT-3',
and 18S reverse,
                                  (SEQ ID NO: 6)
5'-CCATCCAATCGGTAGTAGCG-3';

IFIT2 forward,
                                  (SEQ ID NO: 7)
5'-AGGCTTTGCATGTCTTGG-3',
and IFIT2 reverse,
                                  (SEQ ID NO: 8)
5'GAGTCTTCATCTGCTTGTTGC-3';

IFIT1 forward,
                                  (SEQ ID NO: 9)
5'-TTCGGAGAAAGGCATTAGA,
and IFIT1 reverse,
                                  (SEQ ID NO: 10)
5'-TCCAGGGCTTCATTCATAT;

IFNB1 forward,
                                  (SEQ ID NO: 11)
5'-TCTGGCACAACAGGTAGTAGGC,
and IFNB1 reverse,
                                  (SEQ ID NO: 12)
5'-GAGAAGCACAACAGGAGAGCAA;

HPRT1 forward,
                                  (SEQ ID NO: 13)
5'-GAAAAGGACCCCACGAAGTGT,
and HPRT1 reverse,
                                  (SEQ ID NO: 14)
5'-AGTCAAGGGCATATCCTACAACA;

BRD4 forward,
                                  (SEQ ID NO: 15)
5'-GAGCTACCCACAGAAGAAACC,
and BRD4 reverse,
                                  (SEQ ID NO: 16)
5'-GAGTCGATGCTTGAGTTGTGTT;

IL-1β forward,
                                  (SEQ ID NO: 17)
5'-ATGATGGCTTATTACAGTGGCAA,
and IL-1β reverse,
                                  (SEQ ID NO: 18)
5'-GTCGGAGATTCGTAGCTGGA;

IL-6 forward,
                                  (SEQ ID NO: 19)
5'-ACTCACCTCTTCAGAACGAATTG,
and IL-6 reverse,
                                  (SEQ ID NO: 20)
5'-CCATCTTTGGAAGGTTCAGGTTG;

IL-8 forward,
                                  (SEQ ID NO: 21)
5'-TTTTGCCAAGGAGTGCTAAAGA,
and IL-8 reverse,
                                  (SEQ ID NO: 22)
5'-AACCCTCTGCACCCAGTTTTC;

CDK9 forward,
                                  (SEQ ID NO: 23)
5'-ATGGCAAAGCAGTACGACTCG,
and CDK9 reverse,
                                  (SEQ ID NO: 24)
5'-GCAAGGCTGTAATGGGGAAC;
```

-continued

CCNT1 forward,
(SEQ ID NO: 25)
5'-ACAACAAACGGTGGTATTTCACT,
and

CCNT1 reverse,
(SEQ ID NO: 26)
5'-CCTGCTGGCGATAAGAAAGTT.

Mouse.
Actb forward,
(SEQ ID NO: 27)
5'-TTACGGATGTCAACGTCACAGTTC,
and

Actb reverse,
(SEQ ID NO: 28)
5'-ACTATTGGCAACGAGCGGTTC;

Mip1a forward,
(SEQ ID NO: 29)
5'-CGAGTACCAGTCCCTTTTCTGTTC,
and

Mip1a reverse,
(SEQ ID NO: 30)
5'-AAGACTTGGTTGCAGAGTGTCATG;

Il-6 forward,
(SEQ ID NO: 31)
5'-TGAGATCTACTCGGCAAACCTAGTG,
and

Il-6 reverse,
(SEQ ID NO: 32)
5'-CTTCGTAGAGAACAACATAAGTCAGATACC;

Ifit1 forward,
(SEQ ID NO: 33)
5'-GCCTATCGCCAAGATTTAGATGA,
and

Ifit1 reverse,
(SEQ ID NO: 34)
5'-TTCTGGATTTAACCGGACAGC;

Ifit2 forward,
(SEQ ID NO: 35)
5'-AGAACCAAAACGAGAGAGAGTGAGG,
and

Ifit2 reverse,
(SEQ ID NO: 36)
5'-TCCAGACGGTAGTTCGCAATG;

Mip-2 forward,
(SEQ ID NO: 37)
5'-GTCCCTCAACGGAAGAACCAA,
and

Mip-2 reverse,
(SEQ ID NO: 38)
5'-ACTCTCAGACAGCGAGGCACAT;

Rantes forward,
(SEQ ID NO: 39)
5'-TGCCCACGTCAAGGAGTATTTC,
and

Rantes reverse,
(SEQ ID NO: 40)
5'-TCCTAGCTCATCTCCAAATAGTTGATG;

Il-10 forward,
(SEQ ID NO: 41)
5'-GCAACTGTTCCTGAACTCAACT,
and

Il-10 reverse,
(SEQ ID NO: 42)
5'-ATCTTTTGGGGTCCGTCAACT.

Sequences of primers used for ChIP followed by qPCR were as follows:

Human.
ACTB 5' forward,
(SEQ ID NO: 43)
GAGGGGAGAGGGGGTAAAA,
and

ACTB 5' reverse,
(SEQ ID NO: 44)
AGCCATAAAAGGCAACTTTCG;

IFIT1 5' forward,
(SEQ ID NO: 45)
AGAGGAGCCTGGCTAAGCA,
and

IFIT1 5' reverse,
(SEQ ID NO: 46)
GGTTGCTGTAAATTAGGCAGC;

IFIT2 5' forward,
(SEQ ID NO: 47)
TGCACTGCAACCATGAGG,
and

IFIT2 5' reverse,
(SEQ ID NO: 48)
TGACTCAACAGCACTACCGA;

IL-6 5' forward,
(SEQ ID NO: 49)
CCCAATAAATATAGGACTGGAGATG,
and

IL-6 5' reverse,
(SEQ ID NO: 50)
GAGTTCATAGCTGGGCTCCT;

IL-8 5' forward,
(SEQ ID NO: 51)
TATAAAAGCCACCGGAGCA,
and

IL-8 5' reverse,
(SEQ ID NO: 52)
GCCAGCTTGGAAGTCATGTT.

Mouse.
Actb 5' forward,
(SEQ ID NO: 53)
GGGCTACAGTGGGTGAAAGG,
and

Actb 5' reverse,
(SEQ ID NO: 54)
GGGCTACAGTGGGTGAAAGG;

Ifit1 5' forward,
(SEQ ID NO: 55)
TGAAAAGAGCACACCCCCTA,
and

Ifit1 5' reverse,
(SEQ ID NO: 56)
CTCCTCAGAAACCTGCCTTG;

Ifit2 5' forward,
(SEQ ID NO: 57)
AGCCACACCCGACTAACG,
and

Ifit2 5' reverse,
(SEQ ID NO: 58)
CTTGGTGCTTTGAGGGATCT;

-continued

```
Il-6 5' forward,
                                        (SEQ ID NO: 59)
AATGTGGGATTTTCCCATGA,
and Il-6 5' reverse,
                                        (SEQ ID NO: 60)
GCGGTTTCTGGAATTGACTATC;

Mip2-a 5' forward,
                                        (SEQ ID NO: 61)
GGGCTTTTCCAGACATCGT,
and Mip2-a 5' reverse,
                                        (SEQ ID NO: 62)
TGAAGTGTGGCTGGAGTCTG.
```

Transfection with siRNA

Transfection experiments were performed using the Lipofectamine RNAiMAX transfection reagents according to the manufacturer's instructions (Invitrogen). Cells were transfected with small interfering (si)RNA pools targeting the genes encoding human Top1 (L-005278-00-0005; Dharmacon), BRD4 (L-004937-00-0005; Dharmacon), CDK9 (L-003243-00-0005; Dharmacon), CCNT1 (L-003220-00-0005; Dharmacon), or with a control non-targeting pool (D-001810-10-05; Dharmacon) at the final concentration of 50 nM. Transfected cells were used 48 hours after transfection, and the efficiency of gene knockdown was determined by qPCR.

Microarray Analysis

A549 cells were transfected with siRNA targeting the gene encoding Top1 or control nontargeting siRNA (siCtrl), then infected in triplicate with the PR8ΔNS1 virus (MOI=3). Nontransfected cells were also infected, as a further control. RNA was isolated from infected and uninfected cells with a Qiagen RNeasy kit and 200 ng of RNA per sample was then used to prepare labeled RNA that was hybridized to Human HT-12 v4 Expression BeadChips (Illumina). Data were analyzed with Genespring software (version 12.5). To determine the effect of Top1 depletion on the magnitude of cell response during infection, raw signal values obtained from uninfected and infected cells in all siRNA treatments were quantile-normalized before being baseline-transformed to the medians of signal values for the corresponding uninfected siRNA-treated samples. For the identification of probe sets with statistically significant differences in magnitude of response ($P<0.01$), the statistical ANOVA test followed by a post-hoc (Tukey's honest significant difference) test was conducted. Genes differentially expressed after treatment were selected with siTop1 using a threshold ≥1.5-fold change ($P<0.01$) in their expression relative to siCtrl-treated cells. When indicated, infection-induced genes were identified as the ones showing a fold change≥1.5 ($P<0.01$) in their expression in infected-siCtrl-treated cells as compared to uninfected siCtrl-treated cells. All computations of P values were subjected to multiple-testing correction using the Benjamini-Hochberg method. For purposes of presentation in the heat maps, genes represented by multiple probe sets in the microarray were plotted as the averaged values of those probe sets.

To determine the effect of Top1 depletion under basal conditions, raw signal values from uninfected siRNA-treated cells were quantile-normalized before being baseline-transformed to the median of all samples. A statistical ANOVA test followed by a post-hoc test was then conducted. Genes regulated by the siRNA targeting the Top1 gene were defined as genes with a fold change≥1.5 ($P<0.01$) in their expression as compared to the siCtrl-controls. Normalized signal-intensity values of a list of canonical housekeeping genes were also used to determine the overall effect of the depletion of Top1 in cells. A full list of the affected genes is shown in Table 1 ("Top1 depletion").

Functional analyses of differentially regulated genes were conducted with the Ingenuity Pathways Analysis (Ingenuity Systems). This system was used for the identification of canonical pathways that showed "enrichment" among groups of genes with significant changes in their expression by microarray analysis. A right-tailed Fisher's exact test was used for calculation of P values determining the probability that each pathway assigned to a specific data set was due to chance alone. In addition, the DAVID gene-ontology analysis was also used to identify genes associated with cytokine activity(41, 42).

Mice and Related Experiments

C57BL/6J female mice were purchased from The Jackson Laboratories and housed under specific pathogen-free conditions in the animal care facility at the Icahn School of Medicine at Mount Sinai (ISMMS). Mice were studied at 7-12 weeks of age. All experiments were approved by the institutional animal care and use committee and carried out in accordance with the 'Guide for the Care and Use of Laboratory Animals' (NIH publication 86-23, revised 1985).

For the septic shock model, mice were injected intraperitoneally (i.p.) with 10 mg/kg of ultra pure LPS (from E.coli 0111:B4 strain-TLR4 ligand, InvivoGen) resuspended in 200 µl of water. After isoflurane anesthesia, one group of mice also received a first retro-orbital intravenous injection with a dose of 30 mg/kg of CPT 30 minutes before LPS treatment followed by an i.p. challenge with the same dose of CPT one hour after LPS injection. For the acute liver failure model, mice were injected i.p. with a mixture of 5 mg of D-(+)-galactosamine (Sigma) and 500 ng of ultrapure LPS (Invivogen) (referred as D-GalN/LPS), in 200 ml of water. One group of mice was also injected i.p. with 110 mg/kg of CPT one hour before GalN/LPS treatment.

During both LPS and D-GalN/LPS treatments, mice were monitored 8 times daily for a total of 6 days. In case of survival, animals were under observation twice per day for the following month and every week for additional months. No side effect of the treatment was detected in mice monitored for at least 3 months.

Quantitative mRNA analysis for inflammatory gene expression was conducted after RNA isolation from the spleens of untreated and CPT-treated mice 90 minutes after LPS injection. For this, spleens were homogenized in 1 mL of TRIzol® Reagent (Life Technologies) using a mechanical homogenizer. RNA separation and isolation were performed using chloroform and isopropanol (both from Sigma), respectively, according to manufacturer's instructions (Life Technologies). cDNA synthesis and qPCR were performed as described above. A piece of the same spleen was also analyzed by flow cytometry. Cell suspensions were obtained after cutting the organs into small pieces followed by 30 minutes incubation at 37° C. in DMEM containing 1 mg/mL collagenase D (Roche) and 20 µg/mL DNase (Roche). Tissue suspensions were then filtered through a 70 µm cell strainer (BD Falcon) and red blood cells were lysed using 1 mL of RBC Lysis Buffer (Affimetrix eBioscience). For surface staining, cells were suspended in PBS containing 2% FBS and anti-mouse CD16/32. All antibodies were purchased from Biolegend: anti-mouse CD45 (clone 30-F11), CD11c (N418), CD11b (M1/70), Ly6C (HK 4.1), CD69 (H1.2F3) and MHC-II (M5/114.15.2). Dead cells were discriminated using the Zombie Aqua™ Fixable Viability Kit (Biolegend), referred to as Life/Death dye. Acquisition of stained cells was made with a BD LSRII flow cytometer (BD Bioscience) and data was analyzed with FlowJo software (Treestar).

To determine the cytokine concentration during the treatment, 50 μL of blood was collected retro-orbitally 4 hours after LPS injection. Serum and plasma were separated after centrifugation at 10,000 rpm for 10 minutes. Quantitative determination of GM-CSF, IL-1β, IL-6 and TNFα in mouse serum was performed using a Mouse Inflammatory Magnetic 4-Plex Panel (Novex Life Technology), according to the manufacturer's instructions. Data was acquired using a Luminex® 100/200™ plate reader.

ChIP

ChIP experiments were conducted as described(43). For experiments with ChIP followed by qPCR, 10 minutes of crosslinking was performed for both the anti-RNA polymerase II (RNAPII) (MMS-126R; Covance) and the anti-Top1 (A302-589A; Bethyl) antibodies. Sonication was performed in a refrigerated Bioruptor (Diagenode), and conditions were optimized to generate DNA fragments of approximately 200-1,000 bp. Lysates were pre-cleared for 3 hours with the appropriate isotype-matched control antibody (rabbit IgG 2729; Cell Signaling) or mouse IgG (5415; Cell Signaling). Specific antibodies were coupled for 6 hours with magnetic beads bound to anti-mouse IgG (Dynabeads M-280 Sheep Anti-Mouse IgG; 112-02; Invitrogen) or anti-rabbit IgG (Dynabeads M-280 Sheep Anti-Mouse IgG; 112-04; Invitrogen). Antibody-bound beads and chromatin were then immunoprecipitated overnight at 4° C. with rotation. After the wash steps, reverse crosslinking was carried out overnight at 65° C. After digestion with RNase and proteinase K (Roche), the DNA obtained by ChIP was then isolated with a MinElute kit (28004; Qiagen) and used for downstream applications. The statistical significance of ChIP qPCR analysis was determined with a two-tailed Student's paired t-test.

ChIP-Seq Sample Preparation and Sequencing

Following sonication on a Bioruptor Pico (Diagenode), input and IP samples were analyzed on an Agilent Bioanalyzer (DNA High Sensitivity kit) to confirm that fragment distributions were within the expected size range. Sheared Input and ChIP DNA samples were then end repaired using NEB End repair module (New England Biolabs) and cleaned up using 1.5× AMPure XP beads (Beckman Coulter Inc.) according to the manufacturer's instructions, but omitting the final elution step. Next, A-tailing was done on-beads using the NEB A-tailing module, followed by addition of 20% PEG/NaCl in a 1.5× ratio to AMPure XP bead cleanup, again omitting the final elution step. Adaptor ligation was performed on the sample with beads using the NEB Quick Ligation Module and 80 uM of DNA Multiplex Adaptor. 20% PEG/NaCl was added in a 1.5× ratio followed by AMPure XP cleanup. Samples were then eluted from beads and split into two aliquots. Each aliquot was amplified for 28 cycles using KAPA HiFi HotStart ReadyMix and 25 uM of PE Forward Primer, and 25 uM of an indexed reverse primer. PCR reactions were cleaned using 1.5× AMPure XP beads according to the manufacturer's protocol and size selected for 250-500 nt fragments on the BluePippin platform using 2% M1 Marker gels. Size selected libraries were cleaned using 1.8× AMPure XP beads and sequenced on the HiSeq 2500 platform in a 100 nt single-end read format.

Adapters Used in Ligation

```
Adapter1
                                        (SEQ ID NO: 63)
    5'P-GATCGGAAGAGCACACGTCT Adapter2
                                        (SEQ ID NO: 64)
    5' ACACTCTTTCCCTACACGACGCTCTTCCGATC*T
* = phosphorothioate
```

Barcode PCR Primers:

```
                                        (SEQ ID NO: 65)
5'AATGATACGGCGACCACCGAGATCTACACTCTTTCCCTACACGACGCT
CTTCCGATC*T (SEQ ID NO: 66)
5'CAAGCAGAAGACGGCATACGAGAT[NNNNNN]GTGACTGGAGTTCAGA
CGTGTGCTCTTCCGATC*T
```

Where 'N' corresponds to the barcode sequences used.

ChIP-Seq Data Processing

ChIP-Seq reads were trimmed for adapter sequences using 'cutadapt'. Reads were then filtered using 'sickle' with a minimum quality threshold of 20 and retaining only sequences containing at least 20 bases. QC-filtered reads were then aligned against the human reference genome (GRCh37) using STAR, selecting only non-ambiguous alignments and allowing up to 5 mismatches for each alignment. The resulting BAM files were processed using the R package "Pasha" with default parameters in order to exclude artefactual enrichments, estimate fragments elongation, and prepare genome-wide read coverage tracks in variable-step WIG format. WIG scores were finally rescaled for each sample by dividing all values by the average genome wide enrichment value.

Average Profiles Computation

The average read coverage for selected genes was calculated across the annotated gene regions including 2 kb flanking regions. For each gene, coverage in flanking regions was sampled across 167 equally spaced bins and the resulting values were averaged across the upstream and downstream regions of all selected genes. Coverage across the annotated region of each gene was calculated in 666 equally spaced bins within the annotated start and end coordinates and the resulting vectors were averaged across all genes and combined with the gene-flanking regions to create a composite average profile of 1000 points covering selected annotations and 2 kb of each flanking region. All average profiles were normalized based on the average ChIP signal across the third quartile (i.e. last 50-75%) of the gene body of active genes (previously identified by Gro-Seq profiling(44)), to account for differences in ChIP-efficiency between experiments.

Chemical Synthesis of Topotecan-Alkyne.

The 10-hydroxyl of topotecan does not contribute to the binding between human topoisomerase I covalently joined to double-stranded DNA and topotecan (according to the reported x-ray crystal structure(45)). Therefore, an alkyne group was introduced to the 10-hydroxyl group of TPT through a Mitsunobu reaction(46). Topotecan hydrochloride was dissolved in distilled water and further neutralized by adding (dropwise) a saturated solution of sodium bicarbonate (NaHCO3) until the pH reached 9-10. Hydrochloride-free topotecan was extracted from this solution by washing the aqueous phase with dichloromethane (DCM) 3 times, combining the organic phase, drying it by incubation with sodium sulfate (Na2SO4) for one hour, and finally evaporating DCM under reduced pressure. The topotecan was then fully dissolved together with 5 eq. triphenylphospine (Ph3P) and 5 eq. propargyl alcohol in a small volume of anhydrous tetrahydrofuran (THF). Five eq. of diethyl azodicarboxylate (DEAD) was then added dropwise into the solution. The reaction was monitored by running thin layer chromotography (TLC). The reaction was finished at room temperature in 2 hours. The solvents were removed by using a rotary evaporator (Rotovap). The product was purified by applying preparative HPLC with a gradient elution consisting of methanol (MeOH) and $H_2O$. Purity was ≥95% and the rude yield was 74%. $^1$HNMR (MeOH-$d_6$, 600 MHz): δ 8.95 (1H, s), 8.43 (1H, d, J=9.5 Hz), 8.02 (1H, d, J=9.5 Hz), 7.68 (1H, s), 5.61 (1H, d, J=16.2 Hz), 5.43 (1H, d, J=16.2 Hz), 5.39 (2H, s), 5.20 (2H, d, J=2.1 Hz), 4.18 (2H, s), 3.31 (1H, s), 3.03 (6H, s), 1.99 (2H, m), 1.04 (3H, t, J=7.3 Hz). Calculation for $C_{26}H_{26}N_3O_5$, $[M+H]^+$, and $C_{52}H_{51}N_6O_{10}$, $[2M+H]^-$, were 460.1871 and 919.3667, respectively, 460.2103 and 919.3643 were found in HRMS(47). All chemical reagents and solvents were commercially purchased from Sigma-Aldrich.

Chemical Immunoprecipitation (Chem-ChIP)

A549 cells (100 million/condition) were pre-treated for one hour with 100 nM of Topotecan-Alkyne (TPT-A) or DMSO, infected with influenza PR8ΔNS1 virus, and at one hour postinfection, treated again with TPT-A or DMSO. Cells were collected at 6 hours p.i. and treated as described above for the ChIP procedure. Sonicated DNA fragments for each condition were separated into 500 μL aliquots. The following reagents were added sequentially with vortexing after each addition: 11.3 μL of 5 mM biotin-azide (final concentration: 100 μM), 11.3 μL of 50 mM tris(2-carboxyethyl)phosphine (TCEP, final concentration: 1 mM), 34 μL of 1.7 mM tris(benzyltriazolylmethyl)amine (TBTA, final concentration: 100 μM), and 11.3 μL of 50 mM copper(II) sulfate pentahydrate ($CuSO_4 \cdot 5H_2O$, final concentration: 1 mM). These mixtures were then incubated at room temperature for one hour, with vortexing after the first 30 minutes.

Chromatin aliquots were combined and centrifuged for 5 minutes at 6,500 g at 4° C. Supernatant was then removed for downstream immunoprecipitation. Lysates were precleared for 3 hours with the appropriate isotype-matched control antibody (rabbit IgG 2729; Cell Signaling). IgG antibody was coupled for 6 hours with magnetic beads bound to anti-rabbit IgG (Dynabeads M-280 Sheep Anti-Mouse IgG; 112-04; Invitrogen). Antibody-bound beads and chromatin were then immunoprecipitated overnight at 4° C. with rotation. Chromatin used for the TPT-A-biotin pulldown was immunoprecipitated for 30 minutes at 4° C. with rotation using streptavidin beads (Life Technologies, 65001). After the wash steps, reverse crosslinking was carried out overnight at 65° C. After digestion with RNase and proteinase K (Roche), DNA obtained by ChIP was isolated with a MinElute kit (28004; Qiagen) and used for downstream applications. The statistical significance of ChIP qPCR analysis was determined with a two-tailed Student's paired t-test.

Stranded RNA-Sequencing 1 ug of RNA was treated using Illumina's Ribo-Zero Gold rRNA Removal Kit (Human/Mouse/Rat), and purified post-depletion with 1.6× ratio AMPureXP beads. Directional RNA libraries were prepared using NEBNext Ultra Directional RNA Library Prep kit for Illumina, per kit instructions. Fragment size distribution and concentration of the PCR amplified libraries were assessed using the Qbit and Agilent Bioanalyzer. Finally, samples were sequenced on the Hi Seq2500 platform in a 100 bp single-end read format.

RNA-Seq Data Analysis

Following adapter removal with cutadapt and base quality trimming to remove 3' ends if more than 20 bases with Q<20 were present, reads were mapped to the human (hg19) and Ebola (*H. sapiens*-tc/COD/1976/Yambuku-Mayinga, NC 002549) reference genomes using STAR(48) and gene- and transcript count summaries were generated using Featurecounts(49). Read counts were then combined into a numeric matrix with genes in rows and experiments in columns, and used as input for differential gene expression analysis with the Bioconductor edgeR package(50). Normalization factors were computed using the weighted trimmed mean of M-values (TMM), and dispersions (common, trended, and tagwise) were estimated before fitting a negative binomial General Linearized Model that accounted for experimental conditions with two biological replicates each. Finally, a likelihood ratio test was carried against selected contrasts. P-values were corrected for multiple testing using the Benjamin-Hochberg (BH) method and used to select genes with significant expression differences (FDR q<0.05).

Proteomic Analysis

A549 cells were treated with CPT or DMSO and infected with the influenza PR8ΔNS1 virus as described above, collected at 6 hours p.i., washed 3 times with PBS (including protease inhibitors (Roche), then frozen as cell pellets. These pellets were sent to Bioproximity LLC, where global proteomic profiling was acquired using UPLC-MS/MS. For the analysis of mass spectrometry "hits," initial thresholds were calculated in duplicate experiments for protein abundances in both DMSO and CPT treated, uninfected cells. Next, protein abundances were calculated in the respective infected conditions, and normalized using non-infected abundances. Upregulated hits were considered as having a normalized unique protein score above 5 in the DMSO treated, infected cells. The statistical comparison between normalized infected identifications was determined with a two-tailed Student's t-test under the assumption of equal variances between groups.

Statistical Methods

The statistical significance of all pairwise comparisons in qPCR assays' change in cycling threshold (ΔCT) values was determined with a two-tailed Student's t-test under the assumption of equal variances between groups. The inventors did not find significant differences (false-discovery rate, q<0.05) between contrast groups in Levene's tests of equality of variances, or departures from normality as assessed by Shapiro-Wilk tests. Survival significance in in vivo experiments was calculated using a Log-Rank Test.

TABLE 1

List of genes affected by siTop and siCTRL siRNAs

A. UI_siTOP1_affected_genes.
This table provides a list of genes that were shown to be affected by siTOP1 treatment in uninfected cells. siTOP1 affected genes are defined as genes that display >1.5 fold change (p < 0.01) difference between siTOP1 and siCtrl treated cells. *Note that there were no siCtrl affected cells found in uninfected conditions.

| Symbol | Entrez_Gene_ID | Accession | Probe_Id | LOG2(siTOP1 ui/siCtrl ui) | LOG2(UT ui/siCTRL ui) |
|---|---|---|---|---|---|
| TNFRSF12A | 51330 | NM_016639.1 | ILMN_1689004 | 0.79688612 | 0.200222969 |
| LOC729580 | 729580 | XM_001130700.1 | ILMN_3300198 | −0.68153903 | −0.0361096 |
| CHFR | 55743 | NM_018223.1 | ILMN_1653828 | −0.641814846 | 0.185488224 |
| C1orf97 | 84791 | NM_032705.2 | ILMN_1808769 | 0.690006575 | −0.016222954 |
| FGL1 | 2267 | NM_201553.1 | ILMN_2366192 | −0.664460823 | 0.113610901 |
| PDLIM7 | 9260 | NM_213636.1 | ILMN_1690125 | 0.903765657 | −0.124062223 |
| MYBL1 | 4603 | NM_001080416.1 | ILMN_3241046 | 0.75487485 | −0.07453664 |
| LOC100130506 | 100130506 | XM_001724500.1 | ILMN_3263225 | −0.591507259 | 0.014842987 |
| TOP1 | 7150 | NM_003286.2 | ILMN_2192316 | −1.85568837 | −0.11454359 |
| FGFR3 | 2261 | NM_022965.1 | ILMN_1723123 | −1.02693973 | 0.06241035 |
| MT1G | 4495 | NM_005950.1 | ILMN_1715401 | 0.749953906 | −0.267073944 |
|  |  | BX104737 | ILMN_1820787 | 0.71171713 | 0.21025372 |
| NT5E | 4907 | NM_002526.1 | ILMN_1697220 | 1.01761214 | −0.57406106 |
| ARV1 | 64801 | NM_022786.1 | ILMN_1800935 | −1.047615977 | 0.037604651 |
| RAB26 | 25837 | NM_014353.4 | ILMN_1790317 | −0.62864812 | 0.18708055 |
| H1F0 | 3005 | NM_005318.2 | ILMN_1757467 | −0.63556194 | −0.077735271 |
| POM121C | 100101267 | NM_001099415.1 | ILMN_3235808 | −0.605417553 | −0.011170706 |
| AIF1L | 83543 | NM_031426.2 | ILMN_3246401 | 0.95308523 | 0.075160347 |
| TOP1P2 | 7152 | NR_001283.1 | ILMN_2043109 | −2.471033446 | −0.05332343 |
| TCEA3 | 6920 | NM_003196.1 | ILMN_1726928 | 0.867808457 | −0.107756773 |
| GBP1 | 2633 | NM_002053.1 | ILMN_2148785 | 0.64881214 | 0.054281074 |
| C15orf48 | 84419 | NM_032413.2 | ILMN_1805410 | 0.609870253 | −0.050237972 |
| GLIPR2 | 152007 | NM_022343.2 | ILMN_1652631 | 0.92787743 | 0.119988282 |
| KIAA0114 | 57291 | NR_024031.1 | ILMN_3248882 | −0.586027801 | 0.105688099 |
| HTR2B | 3357 | NM_000867.3 | ILMN_1735764 | −0.681951706 | 0.125425654 |
| AXIN2 | 8313 | NM_004655.2 | ILMN_1724480 | −1.239182586 | −0.046579356 |
| SMOX | 54498 | NM_175840.1 | ILMN_2367258 | 0.684064231 | −0.112607953 |
| TERC | 7012 | NR_001566.1 | ILMN_1766573 | 0.690799258 | −0.145799482 |
| AMHR2 | 269 | NM_020547.1 | ILMN_1736412 | 0.98354087 | 0.053880844 |
| TAGLN | 6876 | NM_003186.3 | ILMN_1778668 | 2.11941162 | 0.26548624 |
| TAGLN | 6876 | NM_003186.3 | ILMN_2400935 | 1.22026697 | 0.288511106 |
| CPS1 | 1373 | NM_001875.2 | ILMN_1792748 | −0.79366204 | −0.131956414 |
| RBM20 | 282996 | XM_939337.2 | ILMN_1749540 | −0.683412575 | −0.129894895 |
| SNORA12 | 677800 | NR_002954.1 | ILMN_3238435 | 1.321049354 | −0.194807046 |
| DRAP1 | 10589 | NM_006442.2 | ILMN_2112301 | 0.61248845 | −0.003748894 |
| HMGCS1 | 3157 | NM_002130.6 | ILMN_1797728 | 0.9025529 | 0.05592473 |
| IL32 | 9235 | NM_001012633.1 | ILMN_2368530 | 0.87103527 | 0.134050364 |
| UBE2A | 7319 | NM_181762.1 | ILMN_2307455 | −0.999205317 | 0.124403313 |
| ANKRD30A | 91074 | XM_001131823.1 | ILMN_1813607 | −0.78561463 | −0.16655349 |
| RP2 | 6102 | NM_006915.1 | ILMN_1659255 | 0.62947829 | 0.154788334 |
| HSPA5 | 3309 | NM_005347.2 | ILMN_1773865 | −0.6029415 | −0.044481914 |
| LOC642031 | 642031 | XM_936101.2 | ILMN_1655694 | −0.70744637 | 0.016355514 |
| PTGER4 | 5734 | NM_000958.2 | ILMN_1795930 | 0.59165698 | 0.01362864 |
| RARRES3 | 5920 | NM_004585.3 | ILMN_1701613 | 0.809372087 | 0.028225897 |
| KLF13 | 51621 | NM_015995.2 | ILMN_1679929 | −0.78709221 | −0.102007553 |
| TDO2 | 6999 | NM_005651.1 | ILMN_1716859 | 0.707775417 | 0.016151267 |
| POLA1 | 5422 | NM_016937.2 | ILMN_2191436 | −0.60391042 | 0.00652504 |
| AXL | 558 | NM_021913.2 | ILMN_1701877 | 0.624198611 | −0.376123419 |
| ETS1 | 2113 | NM_005238.2 | ILMN_2122103 | 1.2781992 | 0.077920595 |
| ADHFE1 | 137872 | NM_144650.2 | ILMN_1702858 | 0.603352825 | −0.006806055 |
| DKK3 | 27122 | NM_013253.4 | ILMN_2398159 | 1.13973013 | −0.22420183 |
| HAS3 | 3038 | NM_005329.2 | ILMN_1794501 | 0.64983495 | −0.30576771 |
| KIAA0494 | 9813 | NM_014774.1 | ILMN_1697597 | −1.0006275 | −0.039633113 |
| CTGF | 1490 | NM_001901.1 | ILMN_1699829 | 1.09646861 | 0.120506607 |
| MT1A | 4489 | NM_005946.2 | ILMN_1691156 | 0.786111493 | −0.111468631 |
| GLIPR1 | 11010 | NM_006851.2 | ILMN_1769245 | 1.014209864 | −0.101455846 |
| EMP1 | 2012 | NM_001423.1 | ILMN_1801616 | 0.919857981 | −0.214182539 |
| FLNB | 2317 | NM_001457.1 | ILMN_1664922 | 0.62071417 | 0.118080452 |
| HES4 | 57801 | NM_021170.2 | ILMN_1653466 | −0.637434977 | 0.028224313 |
| ITGB1 | 3688 | NM_133376.1 | ILMN_1784454 | 0.632910074 | −0.255707116 |
| RNF182 | 221687 | NM_152737.2 | ILMN_3243112 | 0.679615183 | −0.148406347 |
| LRIG1 | 26018 | NM_015541.2 | ILMN_1707342 | 0.62043334 | 0.081970217 |
| LRIG1 | 26018 | NM_015541.2 | ILMN_2128795 | 0.96961721 | 0.219930966 |
| JUN | 3725 | NM_002228.3 | ILMN_1806023 | 1.21744315 | −0.11976338 |
| DDC | 1644 | NM_000790.2 | ILMN_2228463 | −0.73583285 | 0.14660422 |
| GADD45A | 1647 | NM_001924.2 | ILMN_2052208 | 0.67682391 | −0.043294906 |
| SCARNA13 | 677768 | NR_003002.1 | ILMN_3235325 | 1.553394666 | −0.355927774 |
| STEAP1 | 26872 | NM_012449.2 | ILMN_1733094 | −0.687007248 | 0.048107148 |
| FBN2 | 2201 | NM_001999.3 | ILMN_1670899 | 0.709334684 | −0.031893096 |

TABLE 1-continued

List of genes affected by siTop and siCTRL siRNAs

| | | | | | |
|---|---|---|---|---|---|
| NEXN | 91624 | NM_144573.3 | ILMN_1783276 | 0.69781925 | −0.11239687 |
| KRT86 | 3892 | NM_002284.3 | ILMN_2178226 | 0.70274321 | 0.015918252 |
| SUSD2 | 56241 | NM_019601.3 | ILMN_1693270 | −0.817718204 | −0.129961649 |
| ENC1 | 8507 | NM_003633.1 | ILMN_1779147 | 0.603307102 | −0.059571902 |
| SCARNA16 | 677781 | NR_003013.1 | ILMN_3237446 | 0.98795954 | −0.04826228 |
| NASP | 4678 | NM_002482.2 | ILMN_2348975 | −0.620953557 | −0.006125451 |
| FGA | 2243 | NM_021871.2 | ILMN_1656487 | −1.25749299 | −0.05046654 |
| PMEPA1 | 56937 | NM_199169.1 | ILMN_1734276 | −0.614819204 | −0.105595904 |
| RNFT2 | 84900 | NM_032814.3 | ILMN_3299905 | −0.58586771 | −0.058777177 |
| IFITM2 | 10581 | NM_006435.2 | ILMN_1673352 | 0.59410446 | 0.067030589 |
| PPARGC1A | 10891 | NM_013261.3 | ILMN_1750062 | −0.624065695 | −0.070328394 |
| DCP2 | 167227 | NM_152624.4 | ILMN_1669905 | 0.866223634 | 0.036874134 |
| SNORA62 | 6044 | NR_002324.1 | ILMN_1700074 | 0.913416545 | −0.211138735 |
| CCL2 | 6347 | NM_002982.3 | ILMN_1720048 | 0.94992603 | 0.187575334 |
| UGT1A6 | 54578 | NM_205862.1 | ILMN_1752813 | 0.624857427 | 0.074409485 |
| RAB40B | 10966 | NM_006822.1 | ILMN_2230566 | 0.95001886 | 0.109544437 |
| CMTM3 | 123920 | NM_001048251.1 | ILMN_2370208 | 0.588918964 | −0.005254108 |
| SCARNA18 | 677765 | NR_003139.1 | ILMN_3241373 | 0.911872527 | −0.225079853 |
| COL1A1 | 1277 | NM_000088.3 | ILMN_1701308 | −0.664565879 | 0.107578281 |
| SNORA63 | 6043 | NR_002586.1 | ILMN_3249167 | 0.912852749 | −0.067656196 |
| PLOD2 | 5352 | NM_182943.2 | ILMN_1799139 | 0.710374538 | −0.122722622 |
| | | AK123915 | ILMN_1915076 | −0.878267263 | 0.088602707 |
| RHBDF1 | 64285 | NM_022450.2 | ILMN_1808404 | 0.672701163 | −0.023297943 |
| DEF8 | 54849 | NM_017702.2 | ILMN_1656718 | 0.62197113 | 0.168039324 |
| MYL5 | 4636 | NM_002477.1 | ILMN_2203588 | 0.78584083 | 0.102180161 |
| ANGPTL4 | 51129 | NM_139314.1 | ILMN_1707727 | 0.631161996 | −0.257258734 |
| TP53I3 | 9540 | NM_147184.1 | ILMN_2358919 | 0.63178318 | 0.070819216 |
| C2orf76 | 130355 | NM_001017927.2 | ILMN_1726729 | 0.59960779 | 0.134934421 |
| ANKRD16 | 54522 | NM_019046.1 | ILMN_1659156 | −0.604109908 | 0.133609453 |
| FGL1 | 2267 | NM_201552.1 | ILMN_2326197 | −0.796826524 | −0.058797521 |
| SLC22A3 | 6581 | NM_021977.2 | ILMN_2048478 | −0.597435136 | 0.054885546 |
| UGT1A1 | 54658 | NM_000463.2 | ILMN_1744817 | −0.994615876 | 0.10921796 |
| FGL1 | 2267 | NM_004467.3 | ILMN_1672872 | −0.67326575 | 0.049304168 |
| LOC730316 | 730316 | XM_001128149.1 | ILMN_1662130 | −0.761429458 | 0.009098371 |
| CXXC5 | 51523 | NM_016463.5 | ILMN_1745256 | −0.704693149 | 0.166418721 |
| | | BI254341 | ILMN_1898692 | −0.591407135 | −0.003606319 |
| HLA-B | 3106 | NM_005514.5 | ILMN_1778401 | 0.65215175 | 0.1271294 |
| C4orf18 | 51313 | NM_016613.5 | ILMN_1761941 | −0.92490433 | −0.113853777 |
| SNORA67 | 26781 | NR_002912.1 | ILMN_3247018 | 0.960535664 | −0.076859476 |
| ARHGDIB | 397 | NM_001175.4 | ILMN_1678143 | 0.90150307 | 0.021739326 |
| FGB | 2244 | NM_005141.2 | ILMN_1678049 | −1.0170466 | −0.195286106 |
| FGA | 2243 | NM_000508.3 | ILMN_1779017 | −1.00596718 | −0.053325334 |
| SLC39A1 | 27173 | NM_014437.3 | ILMN_2116714 | −0.731780731 | 0.126303989 |
| SCARNA23 | 677773 | NR_003007.1 | ILMN_3243966 | 0.917700614 | −0.091152506 |
| ANXA3 | 306 | NM_005139.2 | ILMN_1694548 | 0.90890246 | 0.08219083 |
| CXXC5 | 51523 | NM_016463.7 | ILMN_3307729 | −0.720864627 | 0.148050633 |
| IL27RA | 9466 | NM_004843.2 | ILMN_1688152 | 0.708206152 | −0.078108472 |
| NID2 | 22795 | NM_007361.3 | ILMN_1698706 | −0.907045405 | −0.063390734 |
| SLC7A5 | 8140 | NM_003486.5 | ILMN_1720373 | −0.60141438 | −0.081911405 |
| GPR64 | 10149 | NM_005756.2 | ILMN_2349071 | −0.74489117 | −0.169772783 |
| GPR64 | 10149 | NM_001079859.1 | ILMN_1751885 | −0.691600795 | −0.062260945 |
| PLAU | 5328 | NM_002658.2 | ILMN_1656057 | 0.75594963 | −0.42777889 |
| DEFB1 | 1672 | NM_005218.3 | ILMN_1686573 | −0.739463816 | 0.339210514 |
| DKK3 | 27122 | NM_015881.5 | ILMN_1815673 | 1.170641575 | −0.225254855 |

B. INF_siTOP1_affected_genes.

This table provides a list of genes that are affected by siTOP1 treatment in infected cells.
siTOP1 affected genes are defined as genes that display >1.5 fold change (p < 0.01) difference
between siTOP1 and siCtrl treated cells.

| Symbol | Entrez_Gene_ID | Accession | Probe_Id | LOG2(siTOP1 inf/siCtrl inf) | LOG2(siCtrl inf/UT inf) |
|---|---|---|---|---|---|
| FOSB | 2354 | NM_006732.1 | ILMN_1751607 | −0.8999169 | −0.3322195 |
| IL29 | 282618 | NM_172140.1 | ILMN_2149624 | −1.2842454 | −0.258628 |
| CDKN2C | 1031 | NM_078626.2 | ILMN_1656415 | −1.1744431 | −0.3720087 |
| NFKBIE | 4794 | NM_004556.2 | ILMN_1717313 | −0.7878439 | −0.2262368 |
| MX2 | 4600 | NM_002463.1 | ILMN_2231928 | −0.9684901 | −0.0884007 |
| C7orf40 | 285958 | NR_003697.1 | ILMN_3248773 | −0.6210584 | −0.1893482 |
| MDM2 | 4193 | NM_002392.2 | ILMN_1736829 | −0.64931265 | −0.3586847 |
| IL28A | 282616 | NM_172138.1 | ILMN_1662302 | −1.0281136 | −0.2855572 |
| TRIM21 | 6737 | NM_003141.3 | ILMN_1678054 | −0.6874728 | −0.296319 |
| FZD4 | 8322 | NM_012193.2 | ILMN_1743367 | −0.9890267 | −0.2382403 |
| FST | 10468 | NM_006350.2 | ILMN_1712896 | −0.6647269 | −0.1697988 |
| SNPH | 9751 | NM_014723.2 | ILMN_1757532 | −1.09863586 | −0.2964713 |
| EGR1 | 1958 | NM_001964.2 | ILMN_1762899 | −0.8086867 | −0.4593686 |
| IFITM1 | 8519 | NM_003641.3 | ILMN_1801246 | −0.7570722 | 0.0615399 |
| GBP1 | 2633 | NM_002053.1 | ILMN_1701114 | −1.094183 | −0.1940406 |

TABLE 1-continued

List of genes affected by siTop and siCTRL siRNAs

| | | | | | |
|---|---|---|---|---|---|
| GBP1 | 2633 | NM_002053.1 | ILMN_2148785 | −1.3046168 | −0.2415828 |
| ARL4A | 10124 | NM_001037164.1 | ILMN_1743241 | −0.6331816 | −0.2679663 |
| NFKBIA | 4792 | NM_020529.1 | ILMN_1773154 | −0.803072 | −0.2785054 |
| DDX60L | 91351 | NM_001012967.1 | ILMN_3243928 | −0.7132029 | −0.1755512 |
| CEACAM1 | 634 | NM_001024912.1 | ILMN_1716815 | −1.0066406 | −0.1494194 |
| PR1C285 | 85441 | NM_033405.2 | ILMN_1787509 | −0.8756521 | −0.1566705 |
| IFI6 | 2537 | NM_022873.2 | ILMN_1687384 | −1.0527268 | −0.0410035 |
| CCL4L2 | 388372 | NM_207007.2 | ILMN_1716276 | −1.3485759 | −0.4698985 |
| HMGCS1 | 3157 | NM_002130.6 | ILMN_1797728 | −0.61780995 | −0.26354349 |
| ATF3 | 467 | NM_001040619.1 | ILMN_2374865 | −1.054543 | −0.39262 |
| PLA2G4C | 8605 | NM_003706.1 | ILMN_1810191 | −1.0017092 | −0.4082267 |
| FST | 10468 | NM_013409.1 | ILMN_1700081 | −0.7882775 | −0.2796862 |
| MSX1 | 4487 | NM_002448.3 | ILMN_1777397 | −0.66818966 | −0.2943649 |
| ZFP36 | 7538 | NM_003407.2 | ILMN_1720829 | −0.7250638 | −0.0688505 |
| PTGER4 | 5734 | NM_000958.2 | ILMN_1795930 | −1.1175186 | −0.2579415 |
| RARRES3 | 5920 | NM_004585.3 | ILMN_1701613 | −1.092596 | −0.0491276 |
| BAMBI | 25805 | NM_012342.2 | ILMN_1691410 | −0.7962943 | −0.3390822 |
| CCL4L1 | 9560 | NM_001001435.2 | ILMN_2100209 | −1.2559795 | −0.247615 |
| CD83 | 9308 | NM_004233.3 | ILMN_2328666 | −1.0053185 | −0.423587 |
| LRRN3 | 54674 | NM_001099660.1 | ILMN_1773650 | −1.4017909 | 0.0450371 |
| CTGF | 1490 | NM_001901.1 | ILMN_1699829 | −0.9002167 | −0.3554051 |
| CD83 | 9308 | NM_001040280.1 | ILMN_1780582 | −0.9526702 | −0.336248 |
| NCOA7 | 135112 | NM_181782.2 | ILMN_1687768 | −0.6093724 | −0.2375341 |
| IL28B | 282617 | NM_172139.1 | ILMN_1768900 | −1.263338 | −0.422839 |
| IFNB1 | 3456 | NM_002176.2 | ILMN_1682245 | −0.7334064 | −0.4856274 |
| TRAF1 | 7185 | NM_005658.3 | ILMN_1698218 | −1.0188707 | −0.5337936 |
| PARP14 | 54625 | NM_017554.1 | ILMN_1691731 | −0.7569081 | −0.0350115 |
| JUN | 3725 | NM_002228.3 | ILMN_1806023 | −1.6177514 | −0.2607955 |
| GADD45A | 1647 | NM_001924.2 | ILMN_2052208 | −0.8326409 | −0.290334 |
| ISG20 | 3669 | NM_002201.4 | ILMN_1659913 | −0.8643268 | −0.0428237 |
| HBEGF | 1839 | NM_001945.1 | ILMN_2121408 | −0.7118685 | −0.3566133 |
| ARL5B | 221079 | NM_178815.3 | ILMN_2120022 | −0.65708705 | −0.1352305 |
| LOC728835 | 728835 | XM_001133190.1 | ILMN_3235832 | −1.386984 | −0.426881 |
| HERPUD1 | 9709 | NM_001010990.1 | ILMN_2374159 | −0.6192996 | −0.4323092 |
| BIRC3 | 330 | NM_182962.1 | ILMN_2405684 | −0.92493374 | −0.1164249 |
| SPRY2 | 10253 | NM_005842.2 | ILMN_2089329 | −1.1413693 | −0.4456402 |
| RSAD2 | 91543 | NM_080657.4 | ILMN_1657871 | −1.1078113 | −0.049854 |
| SP8 | 221833 | NM_182700.2 | ILMN_2306630 | −0.7489643 | −0.2925744 |
| SP8 | 221833 | NM_182700.2 | ILMN_2306631 | −0.9144443 | −0.1518735 |
| LOC728014 | 728014 | XM_001127981.1 | ILMN_1812721 | −0.9150528 | −0.4309773 |
| FAM53C | 51307 | NM_016605.1 | ILMN_1744508 | −0.6088298 | −0.25553927 |
| ISG15 | 9636 | NM_005101.1 | ILMN_2054019 | −1.2210255 | −0.1233649 |
| IFIT3 | 3437 | NM_001031683.1 | ILMN_1701789 | −1.2236887 | −0.234428 |
| IDO1 | 3620 | NM_002164.4 | ILMN_3239965 | −1.6760498 | −0.2057302 |
| PMEPA1 | 56937 | NM_199169.1 | ILMN_1734276 | 0.62065028 | 0.17065205 |
| UBE2L6 | 9246 | NM_004223.3 | ILMN_1769520 | −0.8067324 | −0.0230805 |
| IFITM2 | 10581 | NM_006435.2 | ILMN_1673352 | −0.9048199 | −0.0753632 |
| IFITM3 | 10410 | NM_021034.2 | ILMN_1805750 | −0.8953429 | 0.0224376 |
| HOXD11 | 3237 | NM_021192.2 | ILMN_1746158 | −0.9893214 | −0.1177107 |
| INDO | 3620 | NM_002164.3 | ILMN_1656310 | −1.727806 | −0.1583151 |
| OTUD1 | 220213 | XM_001134465.1 | ILMN_1723141 | −1.0304127 | −0.2235839 |
| TNFAIP3 | 7128 | NM_006290.2 | ILMN_1702691 | −1.1599584 | −0.3866343 |
| CFB | 629 | NM_001710.4 | ILMN_1774287 | −1.4131196 | −0.3546948 |
| SERTAD1 | 29950 | NM_013376.3 | ILMN_1794017 | −0.8687901 | −0.4876618 |
| MXD1 | 4084 | NM_002357.2 | ILMN_2214678 | −1.0458506 | −0.3412399 |
| DDX58 | 23586 | NM_014314.3 | ILMN_1797001 | −0.8250834 | −0.0974414 |
| OLR1 | 4973 | NM_002543.3 | ILMN_1723035 | −1.3565716 | −0.3180419 |
| HERC5 | 51191 | NM_016323.2 | ILMN_1729749 | −1.501234 | −0.3039805 |
| IFI44 | 10561 | NM_006417.3 | ILMN_1760062 | −0.963241 | −0.188345 |
| OASL | 8638 | NM_003733.2 | ILMN_1681721 | −1.0641896 | −0.141858 |
| C14orf138 | 79609 | NM_001040662.1 | ILMN_1781102 | −0.6440385 | −0.0861217 |
| RARRES1 | 5918 | NM_206963.1 | ILMN_1800091 | −0.64606526 | −0.20404976 |
| LRRN3 | 54674 | NM_018334.3 | ILMN_2048591 | −1.6341819 | −0.2861779 |
| IFIT2 | 3433 | NM_001547.4 | ILMN_1739428 | −0.9369783 | −0.2324524 |
| GBP4 | 115361 | NM_052941.3 | ILMN_1771385 | −1.170217 | −0.4831044 |
| IFIH1 | 64135 | NM_022168.2 | ILMN_1781373 | −1.2917093 | −0.4102563 |
| BIRC3 | 330 | NM_001165.3 | ILMN_1776181 | −1.1260916 | −0.2714224 |
| ZC3HAV1 | 56829 | NM_020119.3 | ILMN_1724837 | −1.2021345 | −0.0859957 |
| IFIT1 | 3434 | NM_001548.3 | ILMN_1707695 | −0.991368 | −0.372861 |
| TRIM22 | 10346 | NM_006074.3 | ILMN_1779252 | −1.0265094 | −0.2607589 |
| OASL | 8638 | NM_198213.1 | ILMN_1674811 | −1.0072826 | −0.305529 |
| CCL5 | 6352 | NM_002985.2 | ILMN_1773352 | −0.641016 | −0.4722466 |
| CXCL10 | 3627 | NM_001565.2 | ILMN_1791759 | −1.032864 | −0.1736704 |

TABLE 1-continued

List of genes affected by siTop and siCTRL siRNAs

| | | | | | |
|---|---|---|---|---|---|
| OAS2 | 4939 | NM_001032731.1 | ILMN_2248970 | −1.0200633 | −0.0173484 |
| RPPH1 | 85495 | NR_002312.1 | ILMN_1704056 | −0.8189202 | −0.6259048 |
| TNFSF9 | 8744 | NM_003811.2 | ILMN_1751464 | −0.60449315 | −0.3378804 |
| SRPK2 | 6733 | NM_182691.1 | ILMN_1657451 | −1.19846104 | −0.397986 |
| CITED2 | 10370 | NM_006079.3 | ILMN_1663092 | −0.7303138 | −0.1319532 |

C. INF_siCtrl_affected_genes.

This table provides a list of genes that are affected by siCtrl treatment in infected cells. siCtrl affected genes are defined as genes that display >1.5 fold change (p < 0.01) difference between siCtrl and untreated (ut) cells.

| Symbol | Entrez_Gene_ID | Accession | Probe_Id | LOG2(siTOP1 inf/siCTRL inf) | LOG2(ut inf/siCTRL inf) |
|---|---|---|---|---|---|
| RPPH1 | 85495 | NR_002312.1 | ILMN_1704056 | −0.8189202 | −0.6259048 |

D. IPA_canonical Pathways.

This table provides the output of IPA analyses for canonical pathways on siTOP1 affected genes during infection.

| Ingenuity Canonical Pathways | -log(p-value) | Ratio | Molecules |
|---|---|---|---|
| Activation of IRF by Cytosolic Pattern Recognition Receptors | 9.44 | 0.111 | IFIH1, JUN, NFKBIA, NFKBIE, DDX58, IFNB1, IFIT2, ISG15 |
| TNFR2 Signaling | 8.63 | 0.182 | JUN, NFKBIA, NFKBIE, TNFAIP3, BIRC3, TRAF1 |
| 4-1BB Signaling in T Lymphocytes | 6.61 | 0.139 | JUN, NFKBIA, NFKBIE, TNFSF9, TRAF1 |
| Role of RIG1-like Receptors in Antiviral Innate Immunity | 5.82 | 0.102 | IFIH1, NFKBIA, NFKBIE, DDX58, IFNB1 |
| TNFR1 Signaling | 5.67 | 0.0962 | JUN, NFKBIA, NFKBIE, TNFAIP3, BIRC3 |
| CD40 Signaling | 5.04 | 0.0714 | JUN, NFKBIA, NFKBIE, TNFAIP3, TRAF1 |
| Hypoxia Signaling in the Cardiovascular System | 4.94 | 0.0746 | JUN, NFKBIA, NFKBIE, MDM2, UBE2L6 |
| Role of MAPK Signaling in the Pathogenesis of Influenza | 4.91 | 0.0714 | CXCL10, PLA2G4C, IFNB1, RARRES3, CCL5 |
| TWEAK Signaling | 4.86 | 0.105 | NFKBIA, NFKBIE, BIRC3, TRAF1 |
| Interferon Signaling | 4.8 | 0.111 | IFIT3, IFIT1, IFNB1, IFITM1 |
| April Mediated Signaling | 4.61 | 0.093 | JUN, NFKBIA, NFKBIE, TRAF1 |
| B Cell Activating Factor Signaling | 4.52 | 0.0889 | JUN, NFKBIA, NFKBIE, TRAF1 |
| MIF Regulation of Innate Immunity | 4.47 | 0.08 | JUN, NFKBIA, NFKBIE, PLA2G4C |
| Role of Hypercytokinemia/hyperchemokinemia in the Pathogenesis of Influenza | 4.35 | 0.0909 | CXCL10, IFNB1, IFNL1, CCL5 |
| Role of Pattern Recognition Receptors in Recognition of Bacteria and Viruses | 4.15 | 0.0472 | IFIH1, OAS2, DDX58, IFNB1, CCL5 |
| Toll-like Receptor Signaling | 3.94 | 0.0645 | JUN, NFKBIA, TNFAIP3, TRAF1 |
| Induction of Apoptosis by HIV1 | 3.85 | 0.0615 | NFKBIA, NFKBIE, BIRC3, TRAF1 |
| ATM Signaling | 3.82 | 0.0645 | JUN, NFKBIA, GADD45A, MDM2 |
| IL-17A Signaling in Gastric Cells | 3.73 | 0.12 | CXCL10, JUN, CCL5 |
| Role of PI3K/AKT Signaling in the Pathogenesis of Influenza | 3.68 | 0.0541 | NFKBIA, NFKBIE, IFNB1, CCL5 |
| VDR/RXR Activation | 3.38 | 0.0494 | CXCL10, GADD45A, MXD1, CCL5 |
| MIF-mediated Glucocorticoid Regulation | 3.37 | 0.0714 | NFKBIA, NFKBIE, PLA2G4C |
| IL-17A Signaling in Fibroblasts | 3.29 | 0.075 | JUN, NFKBIA, NFKBIE |
| RANK Signaling in Osteoclasts | 3.2 | 0.0421 | JUN, NFKBIA, NFKBIE, BIRC3 |
| Pathogenesis of Multiple Sclerosis | 3.15 | 0.222 | CXCL10, CCL5 |
| Communication between Innate and Adaptive Immune Cells | 3.13 | 0.0367 | CXCL10, IFNB1, CD83, CCL5 |
| Role of PKR in Interferon Induction and Antiviral Response | 3.12 | 0.0652 | NFKBIA, NFKBIE, IFNB1 |
| Molecular Mechanisms of Cancer | 3.07 | 0.0184 | JUN, FZD4, NFKBIA, NFKBIE, CDKN2C, MDM2, BIRC3 |
| PPAR Signaling | 3.07 | 0.0381 | JUN, NFKBIA, NFKBIE, CITED2 |
| Antioxidant Action of Vitamin C | 3.04 | 0.037 | NFKBIA, NFKBIE, PLA2G4C, RARRES3 |
| iNOS Signaling | 3 | 0.0566 | JUN, NFKBIA, NFKBIE |
| CD27 Signaling in Lymphocytes | 2.81 | 0.0526 | JUN, NFKBIA, NFKBIE |
| Role of IL-17A in Arthritis | 2.74 | 0.0476 | NFKBIA, NFKBIE, CCL5 |
| Death Receptor Signaling | 2.65 | 0.0469 | NFKBIA, NFKBIE, BIRC3 |
| Role of Macrophages, Fibroblasts and Endothelial Cells in Rheumatoid Arthritis | 2.61 | 0.0179 | JUN, FZD4, NFKBIA, NFKBIE, CCL5, TRAF1 |
| PI3K Signaling in B Lymphocytes | 2.58 | 0.0286 | JUN, ATF3, NFKBIA, NFKBIE |
| Eicosanoid Signaling | 2.57 | 0.037 | PLA2G4C, RARRES3, PTGER4 |
| Role of Osteoblasts, Osteoclasts and | 2.52 | 0.0208 | JUN, FZD4, NFKBIA, |

TABLE 1-continued

List of genes affected by siTop and siCTRL siRNAs

| | | | |
|---|---|---|---|
| Chondrocytes in Rheumatoid Arthritis | | | NFKBIE, BIRC3 |
| Erythropoietin Signaling | 2.47 | 0.0385 | JUN, NFKBIA, NFKBIE |
| Retinoic acid Mediated Apoptosis Signaling | 2.47 | 0.0417 | ZC3HAV1, IFNB1, PARP14 |
| IL-10 Signaling | 2.45 | 0.0385 | JUN, NFKBIA, NFKBIE |
| Small Cell Lung Cancer Signaling | 2.4 | 0.0337 | NFKBIA, NFKBIE, TRAF1 |
| LPS-stimulated MAPK Signaling | 2.36 | 0.0366 | JUN, NFKBIA, NFKBIE |
| Role of Lipids/Lipid Rafts in the Pathogenesis of Influenza | 2.29 | 0.0741 | RSAD2, IFNB1 |
| Regulation of IL-2 Expression in Activated and Anergic T Lymphocytes | 2.27 | 0.0337 | JUN, NFKBIA, NFKBIE |
| B Cell Receptor Signaling | 2.24 | 0.0234 | JUN, NFKBIA, EGR1, NFKBIE |
| Prostate Cancer Signaling | 2.21 | 0.0303 | NFKBIA, NFKBIE, MDM2 |
| OX40 Signaling Pathway | 2.17 | 0.0316 | JUN, NFKBIA, NFKBIE |
| Acute Phase Response Signaling | 2.15 | 0.0222 | JUN, NFKBIA, NFKBIE, CFB |
| Apoptosis Signaling | 2.14 | 0.0316 | NFKBIA, NFKBIE, BIRC3 |
| UVA-Induced MAPK Signaling | 2.1 | 0.0316 | JUN, ZC3HAV1, PARP14 |
| PPAR Activation | 2.09 | 0.0207 | JUN, NFKBIA, HELZ2, NFKBIE |
| Dendritic Cell Maturation | 2.07 | 0.0191 | NFKBIA, NFKBIE, IFNB1, CD83 |
| p53 Signaling | 2.07 | 0.0312 | JUN, GADD45A, MDM2 |
| IL-1 Signaling | 2.07 | 0.0275 | JUN, NFKBIA, NFKBIE |
| Role of Tissue Factor in Cancer | 1.86 | 0.0259 | CTGF, EGR1, HBEGF |
| CD28 Signaling in T Helper Cells | 1.81 | 0.0227 | JUN, NFKBIA, NFKBIE |
| PKC Signaling in T Lymphocytes | 1.81 | 0.021 | JUN, NFKBIA, NFKBIE |
| IL-6 Signaling | 1.81 | 0.0242 | JUN, NFKBIA, NFKBIE |
| Gαi 12/13 Signaling | 1.79 | 0.0236 | JUN, NFKBIA, NFKBIE |
| Cell Cycle: G2/M DNA Damage Checkpoint Regulation | 1.78 | 0.0408 | GADD45A, MDM2 |
| PI3K/AKT Signaling | 1.75 | 0.0208 | NFKBIA, NFKBIE, MDM2 |
| Relaxin Signaling | 1.62 | 0.0185 | JUN, NFKBIA, NFKBIE |
| Lymphotoxin 1 Receptor Signaling | 1.61 | 0.0328 | NFKBIA, TRAF1 |
| Hepatic Cholestasis | 1.61 | 0.0171 | JUN, NFKBIA, NFKBIE |
| Hepatic Fibrosis/Hepatic Stellate Cell Activation | 1.61 | 0.0205 | CTGF, BAMBI, CCL5 |
| Aryl Hydrocarbon Receptor Signaling | 1.6 | 0.0185 | NCOA7, JUN, MDM2 |
| Role of Cytokines in Mediating Communication between Immune Cells | 1.6 | 0.0364 | IFNB1, IFNL1 |
| Phospholipases | 1.57 | 0.0299 | PLA2G4C, RARRES3 |
| Glucocorticoid Receptor Signaling | 1.52 | 0.0136 | JUN, NFKBIA, NFKBIE, CCL5 |
| IL-17A Signaling in Airway Cells | 1.47 | 0.0274 | NFKBIA, NFKBIE |
| Angiopoietin Signaling | 1.46 | 0.027 | NFKBIA, NFKBIE |
| Tryptophan Degradation to 2-amino-3-carboxymuconate Semialdehyde | 1.45 | 0.0556 | IDO1 |
| Neurotrophin/TRK Signaling | 1.43 | 0.0263 | JUN, SPRY2 |
| Chemokine Signaling | 1.41 | 0.0274 | JUN, CCL5 |
| NF-kB Signaling | 1.41 | 0.0172 | NFKBIA, NFKBIE, TNFAIP3 |
| CCR5 Signaling in Macrophages | 1.4 | 0.0208 | JUN, CCL5 |
| PEDF Signaling | 1.39 | 0.0256 | NFKBIA, NFKBIE |
| IL-17 Signaling | 1.38 | 0.027 | CXCL10, JUN |
| Role of NFAT in Regulation of the Immune Response | 1.38 | 0.0151 | JUN, NFKBIA, NFKBIE |
| Endothelin-1 Signaling | 1.38 | 0.0159 | JUN, PLA2G4C, RARRES3 |
| Wnt-catenin Signaling | 1.38 | 0.0171 | JUN, FZD4, MDM2 |
| Granulocyte Adhesion and Diapedesis | 1.37 | 0.0169 | CXCL10, CCL5, CCL4L1/CCL4L2 |
| NF-kB Activation by Viruses | 1.36 | 0.0241 | NFKBIA, NFKBIE |
| BMP signaling pathway | 1.35 | 0.0241 | JUN, FST |
| Production of Nitric Oxide and Reactive Oxygen Species in Macrophages | 1.33 | 0.0142 | JUN, NFKBIA, NFKBIE |
| Ketogenesis | 1.32 | 0.0476 | HMGCS1 |
| Role of Wnt/GSK-3 Signaling in the Pathogenesis of Influenza | 1.31 | 0.0244 | FZD4, IFNB1 |
| Agranulocyte Adhesion and Diapedesis | 1.3 | 0.0159 | CXCL10, CCL5, CCL4L1/CCL4L2 |
| ErbB Signaling | 1.25 | 0.023 | JUN, HBEGF |
| CDK5 Signaling | 1.23 | 0.0211 | FOSB, EGR1 |
| NAD biosynthesis II (from tryptophan) | 1.21 | 0.0294 | IDO1 |
| Crosstalk between Dendritic Cells and Natural Killer Cells | 1.21 | 0.0208 | IFNB1, CD83 |
| Mevalonate Pathway I | 1.19 | 0.0345 | HMGCS1 |
| Glioma Signaling | 1.17 | 0.0179 | CDKN2C, MDM2 |
| SAPK/JNK Signaling | 1.17 | 0.0194 | JUN, GADD45A |
| IGF-1 Signaling | 1.15 | 0.019 | JUN, CTGF |
| T Cell Receptor Signaling | 1.15 | 0.0183 | JUN, NFKBIA |
| Differential Regulation of Cytokine Production in Macrophages and T Helper Cells by IL-17A and IL-17F | 1.11 | 0.0556 | CCL5 |
| HIF1 Signaling | 1.11 | 0.0185 | JUN, MDM2 |
| Superpathway of Geranylgeranyldiphosphate Biosynthesis I (via Mevalonate) | 1.09 | 0.027 | HMGCS1 |

TABLE 1-continued

List of genes affected by siTop and siCTRL siRNAs

| | | | |
|---|---|---|---|
| iCOS-iCOSL Signaling in T Helper Cells | 1.08 | 0.0163 | NFKBIA, NFKBIE |
| Pancreatic Adenocarcinoma Signaling | 1.08 | 0.0167 | HBEGF, MDM2 |
| Type I Diabetes Mellitus Signaling | 1.07 | 0.0167 | NFKBIA, NFKBIE |
| GADD45 Signaling | 1.06 | 0.0435 | GADD45A |
| fMLP Signaling in Neutrophils | 1.06 | 0.0154 | NFKBIA, NFKBIE |
| Renin-Angiotensin Signaling | 1.06 | 0.0159 | JUN, CCL5 |
| Tryptophan Degradation III (Eukaryotic) | 1.04 | 0.0208 | IDO1 |
| Polyamine Regulation in Colon Cancer | 1.03 | 0.0345 | MXD1 |
| Colorectal Cancer Metastasis Signaling | 1.02 | 0.0115 | JUN, FZD4, PTGER4 |
| Type II Diabetes Mellitus Signaling | 1.02 | 0.0124 | NFKBIA, NFKBIE |
| 14-3-3-mediated Signaling | 1.01 | 0.0165 | SRPK2, JUN |
| Differential Regulation of Cytokine Production in Intestinal Epithelial Cells by IL-17A and IL-17F | 1.01 | 0.0435 | CCL5 |
| Sperm Motility | 1.01 | 0.0141 | PLA2G4C, RARRES3 |
| Role of JAK1, JAK2 and TYK2 in Interferon Signaling | 0.989 | 0.037 | IFNB1 |
| Atherosclerosis Signaling | 0.988 | 0.0146 | PLA2G4C, RARRES3 |
| Protein Ubiquitination Pathway | 0.97 | 0.0112 | MDM2, BIRC3, UBE2L6 |
| G-Protein Coupled Receptor Signaling | 0.959 | 0.0109 | NFKBIA, NFKBIE, PTGER4 |
| IL-15 Production | 0.941 | 0.0323 | IFNB1 |
| GNRH Signaling | 0.936 | 0.0132 | JUN, EGR1 |
| Superpathway of Cholesterol Biosynthesis | 0.898 | 0.0115 | HMGCS1 |
| Role of p14/p19ARF in Tumor Suppression | 0.898 | 0.0312 | MDM2 |
| Synaptic Long Term Depression | 0.884 | 0.0125 | PLA2G4C, RARRES3 |
| Complement System | 0.86 | 0.0286 | CFB |
| Glioblastoma Multiforme Signaling | 0.85 | 0.0121 | FZD4, MDM2 |
| Inhibition of Angiogenesis by TSP1 | 0.848 | 0.0256 | JUN |
| G protein Signaling | 0.845 | 0.0118 | NFKBIA, NFKBIE |
| CXCR4 Signaling | 0.822 | 0.0118 | JUN, EGR1 |
| Thyroid Cancer Signaling | 0.783 | 0.0238 | CXCL10 |
| Melanoma Signaling | 0.763 | 0.0217 | MDM2 |
| UVC-Induced MAPK Signaling | 0.763 | 0.0238 | JUN |
| Role of IL-17F in Allergic Inflammatory Airway Diseases | 0.736 | 0.0208 | CXCL10 |
| RAR Activation | 0.735 | 0.0105 | JUN, CITED2 |
| NRF2-mediated Oxidative Stress Response | 0.713 | 0.0104 | JUN, HERPUD1 |
| Regulation of the Epithelial-Mesenchymal Transition Pathway | 0.709 | 0.0104 | FZD4, EGR1 |
| IL-8 Signaling | 0.688 | 0.00962 | JUN, HBEGF |
| UVB-Induced MAPK Signaling | 0.673 | 0.0182 | JUN |
| IL-2 Signaling | 0.673 | 0.0172 | JUN |
| Thrombopoietin Signaling | 0.658 | 0.0159 | JUN |
| EGF Signaling | 0.651 | 0.0161 | JUN |
| ErbB2-ErbB3 Signaling | 0.645 | 0.0167 | JUN |
| TREM1 Signaling | 0.632 | 0.0141 | CD83 |
| Role of BRCA1 in DNA Damage Response | 0.625 | 0.0154 | GADD45A |
| Cell Cycle: G1/S Checkpoint Regulation | 0.613 | 0.0149 | MDM2 |
| Estrogen-Dependent Breast Cancer Signaling | 0.607 | 0.0137 | JUN |
| LPS/IL-1 Mediated Inhibition of RXR Function | 0.583 | 0.0083 | JUN, HMGCS1 |
| Agrin Interactions at Neuromuscular Junction | 0.578 | 0.0145 | JUN |
| GDNF Family Ligand-Receptor Interactions | 0.578 | 0.0137 | JUN |
| Renal Cell Carcinoma Signaling | 0.567 | 0.0135 | JUN |
| IL-3 Signaling | 0.562 | 0.0135 | JUN |
| Basal Cell Carcinoma Signaling | 0.557 | 0.0133 | FZD4 |
| Prolactin Signaling | 0.552 | 0.0125 | JUN |
| HER-2 Signaling in Breast Cancer | 0.537 | 0.0125 | MDM2 |
| VEGF Family Ligand-Receptor Interactions | 0.537 | 0.0119 | PLA2G4C |
| PDGF Signaling | 0.533 | 0.0118 | JUN |
| Ceramide Signaling | 0.519 | 0.0112 | JUN |
| Cyclins and Cell Cycle Regulation | 0.519 | 0.0111 | CDKN2C |
| TGF-beta Signaling | 0.505 | 0.0112 | JUN |
| TR/RXR Activation | 0.497 | 0.0104 | MDM2 |
| Neuregulin Signaling | 0.485 | 0.0098 | HBEGF |
| Factors Promoting Cardiogenesis in Vertebrates | 0.485 | 0.0105 | FZD4 |
| Bladder Cancer Signaling | 0.481 | 0.0109 | MDM2 |
| G Beta Gamma Signaling | 0.481 | 0.00847 | HBEGF |
| HMGB1 Signaling | 0.465 | 0.0101 | JUN |
| Chronic Myeloid Leukemia Signaling | 0.461 | 0.00952 | MDM2 |
| Mouse Embryonic Stem Cell Pluripotency | 0.458 | 0.0101 | FZD4 |
| Amyotrophic Lateral Sclerosis Signaling | 0.443 | 0.00847 | BIRC3 |
| HGF Signaling | 0.44 | 0.00943 | JUN |
| Cholecystokinin/Gastrin-mediated Signaling | 0.436 | 0.00943 | JUN |
| Rac Signaling | 0.43 | 0.0082 | JUN |
| Fc Epsilon RI Signaling | 0.41 | 0.00855 | PLA2G4C |
| Role of NANOG in Mammalian Embryonic Stem Cell Pluripotency | 0.404 | 0.00862 | FZD4 |
| Androgen Signaling | 0.401 | 0.0069 | JUN |
| G protein Signaling | 0.401 | 0.00806 | PTGER4 |

TABLE 1-continued

List of genes affected by siTop and siCTRL siRNAs

| | | | |
|---|---|---|---|
| Corticotropin Releasing Hormone Signaling | 0.398 | 0.00725 | JUN |
| CCR3 Signaling in Eosinophils | 0.392 | 0.00781 | PLA2G4C |
| Hereditary Breast Cancer Signaling | 0.39 | 0.00781 | GADD45A |
| p38 MAPK Signaling | 0.384 | 0.00847 | PLA2G4C |
| P2Y Purigenic Receptor Signaling Pathway | 0.373 | 0.00709 | JUN |
| Ovarian Cancer Signaling | 0.345 | 0.00699 | FZD4 |
| IL-12 Signaling and Production in Macrophages | 0.343 | 0.00641 | JUN |
| Human Embryonic Stem Cell Pluripotency | 0.343 | 0.00637 | FZD4 |
| Tight Junction Signaling | 0.302 | 0.00621 | JUN |
| Protein Kinase A Signaling | 0.291 | 0.00499 | NFKBIA, NFKBIE |
| Cdc42 Signaling | 0.286 | 0.00562 | JUN |
| Sertoli Cell-Sertoli Cell Junction Signaling | 0.259 | 0.0051 | JUN |
| Clathrin-mediated Endocytosis Signaling | 0.246 | 0.0051 | MDM2 |
| ILK Signaling | 0.243 | 0.00515 | JUN |
| ERK/MAPK Signaling | 0.242 | 0.00481 | PLA2G4C |
| cAMP-mediated signaling | 0.2 | 0.00442 | PTGER4 |

E. Housekeeping Genes (from FIG. 6)
This table shows the fold change of housekeeping gene probe sets in siTOP1 and siCtrl treatment in untreated cells.

| Symbol | Entrez_Gene_ID | Accession | Probe_Id | Fold change (ut/siCtrl) | Fold Change (siTop1/siCtrl) |
|---|---|---|---|---|---|
| ACTB | 60 | NM_001101.2 | ILMN_2038777 | 1.030442776 | 0.91376372 |
| ACTB | 60 | NM_001101.2 | ILMN_1777296 | 0.997219147 | 1.033785873 |
| ACTB | 60 | NM_001101.2 | ILMN_2152131 | 0.976084988 | 0.904851702 |
| ACTG1 | 71 | NM_001614.2 | ILMN_1704961 | 0.987280826 | 1.082083725 |
| ACTG1 | 71 | NM_001614.2 | ILMN_2053178 | 0.940614897 | 0.984845395 |
| GAPDH | 2597 | NM_002046.3 | ILMN_1802252 | 1.003571774 | 1.040955715 |
| GAPDH | 2597 | NM_002046.3 | ILMN_2038778 | 0.98623087 | 1.012285524 |
| GAPDH | 2597 | NM_002046.3 | ILMN_1343295 | 0.994769941 | 0.994512422 |
| GUSB | 2990 | NM_000181.2 | ILMN_1669878 | 1.063641392 | 1.006459269 |
| HPRT1 | 3251 | NM_000194.1 | ILMN_2056975 | 0.964896826 | 0.980897955 |
| HPRT1 | 3251 | NM_000194.1 | ILMN_1736940 | 0.977764237 | 0.942614179 |
| HSP90AB1 | 3326 | NM_007355.2 | ILMN_1673711 | 0.965039924 | 0.968017673 |
| LOC100008588 | 100008588 | NR_003286.1 | ILMN_3243593 | 0.925751153 | 1.068491897 |
| PPIA | 5478 | NM_021130.3 | ILMN_1704529 | 0.990372373 | 0.898282956 |
| RPL13A | 23521 | NM_012423.2 | ILMN_1713369 | 0.961541295 | 0.927157474 |
| RPLP0 | 6175 | NM_001002.3 | ILMN_2402090 | 1.036057724 | 0.98036327 |
| RPLP0 | 6175 | NM_001002.3 | ILMN_1709880 | 0.936566104 | 0.977908811 |
| RPLP0 | 6175 | NM_053275.3 | ILMN_1745075 | 1.020752347 | 1.021331001 |
| TBP | 6908 | NM_003194.3 | ILMN_1697117 | 1.017125925 | 0.929903992 |
| TFRC | 7037 | NM_003234.1 | ILMN_1674243 | 1.007466603 | 0.984137776 |

TABLE 2

Length of genes affected by Top1 depletion.

| Gene Name | Length (kB) |
|---|---|
| PMEPA1 | 63.145 |
| IFITM1 | 1.767 |
| IFITM3 | 7.869 |
| CEACAM1 | 53.931 |
| UBE2L6 | 16.676 |
| ISG20 | 20.847 |
| PARP14 | 50.223 |
| RSAD2 | 32.434 |
| CDKN2C | 13.893 |
| RARRES3 | 9.662 |
| OAS2 | 33.329 |
| ZFP36 | 2.6 |
| IFITM2 | 7.642 |
| MX2 | 47.448 |
| SRPK2 | 288.605 |
| ARL5B | 22.305 |
| DDX58 | 71.023 |
| RARRES1 | 35.962 |
| IFI6 | 6.158 |
| HOXD1 | 2.239 |
| ISG15 | 13.404 |
| CITED2 | 2.844 |
| LRRN3 | 34.449 |
| PRIC285 | 16.154 |
| CXCL10 | 2.421 |
| DDX60L | 181.052 |
| C7orf40 | 3.939 |
| IFI44 | 14.287 |
| C14orf138 | 10.39 |
| OASL | 18.951 |
| IDO1 | 26.516 |
| NFKBIE | 7.623 |
| ARL4A | 4.108 |
| ZC3HAV1 | 66.201 |
| FZD4 | 9.724 |
| BIRC3 | 21.954 |
| IL29 | 2.349 |
| NCOA7 | 150.91 |
| GBP1 | 13.057 |
| MDM2 | 42.515 |
| IFIT2 | 7.328 |
| CCL4L1 | 1.955 |
| PTGER4 | 17.363 |
| FST | 6.78 |
| TRIM22 | 47.503 |
| JUN | 3.54 |
| FAM53C | 17.795 |
| NFKBIA | 3.245 |

TABLE 2-continued

Length of genes affected by Top1 depletion.

| Gene Name | Length (kB) |
|---|---|
| IFIT3 | 13.127 |
| HERPUD1 | 12.816 |
| HMGCS1 | 26.043 |
| OTUD1 | 3.122 |
| IL28A | 1.579 |
| SP8 | 4.616 |
| MSX1 | 4.272 |
| SNPH | 43.025 |
| CTGF | 3.203 |
| TRIM21 | 8.801 |
| CD83 | 19.663 |
| HERC | 49.054 |
| OLR1 | 13.892 |
| FOSB | 7.185 |
| BAMBI | 5.598 |
| CCL5 | 9.303 |
| MXD1 | 45.258 |
| TNFSF9 | 7.367 |
| CFB | 6.435 |
| HBEGF | 13.789 |
| GADD45A | 3.278 |
| ATF3 | 55.444 |
| TNFAIP3 | 16.127 |
| IFIT1 | 13.942 |
| TRAF1 | 26.781 |
| PLA2G4C | 63.01 |
| IFIH1 | 51.63 |
| SPRY2 | 4.993 |
| IL28B | 1.577 |
| CCL4L2 | 1.808 |
| EGR1 | 3.826 |
| IFNB1 | 0.859 |
| SERTAD1 | 4.434 |
| GBP4 | 17.803 |
| RPPH1 | 0.638 |

TABLE 3

Uninfected cells vs. cells infected with WT Ebola.

| GeneID | Name | log2 fold-change | Fold-change | logCPM | LR | PValue | FDR |
|---|---|---|---|---|---|---|---|
| ENSG00000135722 | FBXL8 | −1.002 | −2.003 | 1.493833 | 25.464 | $4.507 \times 10^{-7}$ | 0.009 |
| ENSG00000169429 | CXCL8 | −0.820 | −1.766 | 4.098721 | 20.9099 | $4.814 \times 10^{-6}$ | 0.038 |
| ENSG00000118515 | SGK1 | −0.733 | −1.662 | 4.354329 | 20.604 | $5.648 \times 10^{-6}$ | 0.038 |
| ENSG00000150527 | CTAGE5 | −1.169 | −2.249 | 0.141056 | 17.8579 | $2.38 \times 10^{-5}$ | 0.120 |
| ENSG00000212195 | U3 | −0.846 | −1.798 | 2.107056 | 16.8564 | $4.032 \times 10^{-5}$ | 0.150 |
| ENSG00000219085 | NPM1P37 | −1.765 | −3.398 | −0.47311 | 16.3816 | $5.179 \times 10^{-5}$ | 0.150 |
| ENSG00000198576 | ARC | −2.687 | −6.438 | 0.960089 | 16.3743 | $5.199 \times 10^{-5}$ | 0.150 |
| ENSG00000261546 | CTD-2555A7.3 | 3.117 | 8.675 | −2.19662 | 15.6646 | $7.562 \times 10^{-5}$ | 0.191 |
| ENSG00000197989 | SNHG12 | −0.435 | −1.352 | 5.304464 | 15.0721 | 0.0001035 | 0.209 |
| ENSG00000010327 | STAB1 | −2.168 | −4.493 | −1.06599 | 15.0694 | 0.0001036 | 0.209 |
| ENSG00000240053 | LY6G5B | −0.850 | −1.802 | 1.407376 | 13.772 | 0.0002064 | 0.343 |
| ENSG00000232810 | TNF | −0.977 | −1.969 | 2.801278 | 13.7228 | 0.0002119 | 0.343 |
| ENSG00000204253 | HNRNPCP2 | 1.081 | 2.115 | −0.10604 | 13.5959 | 0.0002267 | 0.343 |
| ENSG00000075826 | SEC31B | −0.596 | −1.511 | 3.158147 | 13.1914 | 0.0002812 | 0.366 |
| ENSG00000265206 | RP5-1171I10.5 | −0.659 | −1.579 | 4.081323 | 13.0288 | 0.0003067 | 0.366 |
| ENSG00000137331 | IER3 | −1.354 | −2.557 | 1.139216 | 12.8214 | 0.0003427 | 0.366 |
| ENSG00000124216 | SNAI1 | −1.271 | −2.413 | 1.943637 | 12.8123 | 0.0003443 | 0.366 |
| ENSG00000167615 | LENG8 | −0.559 | −1.473 | 5.890983 | 12.5331 | 0.0003998 | 0.392 |
| ENSG00000134709 | HOOK1 | 3.031 | 8.173 | −2.23558 | 12.3697 | 0.0004364 | 0.392 |
| ENSG00000143333 | RGS16 | −0.567 | −1.482 | 4.49602 | 12.2926 | 0.0004548 | 0.392 |
| ENSG00000222043 | AC079305.10 | −5.207 | −36.936 | −2.56755 | 12.2467 | 0.0004661 | 0.392 |
| ENSG00000185304 | RGPD2 | −0.895 | −1.860 | 0.411116 | 12.246 | 0.0004663 | 0.392 |
| ENSG00000197774 | EME2 | −0.670 | −1.591 | 4.396867 | 11.8387 | 0.0005801 | 0.468 |
| ENSG00000222489 | SNORA79 | −0.556 | −1.470 | 4.071252 | 11.6244 | 0.0006509 | 0.485 |
| ENSG00000100941 | PNN | −0.381 | −1.302 | 7.068696 | 11.5289 | 0.0006852 | 0.485 |
| ENSG00000231066 | NPM1P9 | −1.253 | −2.383 | −0.44106 | 11.4604 | 0.0007109 | 0.485 |
| ENSG00000255031 | RP11-802E16.3 | −0.589 | −1.504 | 2.156791 | 11.3758 | 0.0007441 | 0.485 |
| ENSG00000208892 | SNORA49 | −0.693 | −1.617 | 3.468492 | 11.3313 | 0.0007621 | 0.485 |
| ENSG00000237721 | AF064858.11 | 1.343 | 2.537 | −0.90433 | 11.3143 | 0.0007691 | 0.485 |
| ENSG00000132424 | PNISR | −0.452 | −1.368 | 7.73851 | 11.2005 | 0.0008177 | 0.500 |

EXAMPLE 2

CPT Preparation and Treatment Protocol

For a mouse, a solution of 30 mg/kg CPT in 200 µl is prepared according to the following procedure. This method can be scaled up to provide 200 µl doses for additional mice.

First, 0.75 mg of CPT is dissolved in a 4:1 mixture chloroform:methanol as follows. The CPT is first dissolved in 112.5 µl of chloroform, to which 37.5 µl of methanol is subsequently added, giving a final volume of 150 µl). The solution is well mixed and then is heated at 55 to 65° C. for few minutes to ensure that the CPT dissolves properly, resulting in a clear solution.

A layer of 50 µl of water is then added to the top of the solution without mixing, resulting in a biphasic solution with a final volume of 200 µl. The water phase remains on top of the chloroform:methanol phase and care should be taken that the phases are maintained.

To separate the two phases (important because chloroform and methanol cannot be injected into the mouse), centrifuge at 4000 rpm for 5 minutes. Given the densities, this centrifugation will force the CPT into the upper water fraction. Remove the top water fraction, e.g., by pipetting, and bring this fraction to the appropriate injection volume, i.e., 200 µl for one mouse. This solution may be allowed to evaporate, e.g., left under a laboratory hood for 10 to 20 min, to allow any remaining chloroform contaminations to evaporate. This solution can then be injected into a mouse.

It is important to avoid pipetting any chloroform from the bottom organic phase, or any interphase material (which may result from impurities in the CPT itself). It is also important to avoid pipetting any suspended particle. The pipetted water fraction must be clear before proceeding to the injection step.

The aqueous CPT solution can be further purified to improve yield and/or purity, such as for example and not limitation, by running the solution over a cellulose-based filter, prior to the injection step.

EXAMPLE 3

Protective Effects of CPT in Animal Models and Ability to Cure Lethal Inflammatory Disorders In this Example, the protective effect of CPT was tested in three different animal models that correlate to human trials. First, the cecal ligation puncture (CPL) was tested in mice, which mimics peritoneal and polymicrobial sepsis in humans. The second model is the Ebola virus (EBOV) infection in mice, which recapitulates the human pathology by taking advantage of a murine-adapted EBOV strain. The third model is the *Legionella pneumophila* infection in guinea pigs, which reproduces the symptoms of Acute Respiratory Distress Syndrome (ARDS) and sepsis in patients.

The Cecal Ligation Puncture Model in Mice

The Cecal Ligation Puncture (CLP) in mice is a reliable model for the induction of peritoneal and polymicrobial sepsis, which closely mimics the human disorder (Rittirsch, Huber-Lang et al. 2009). The procedure has been extensively described (Rittirsch, Huber-Lang et al. 2009) and consists into performing an abdominal midline incision in adult C57BL/6 mice (8-12 weeks old) under anesthesia (a combination of ketamine and xylazine, as recommended by the Institutional Animal Care and Use Committee, IACUC, at ISMMS). The cecum is then isolated and ligated 5 mm from the cecal tip, away from the ileocecal valve, and the ligated cecal stump perforated by one single through-and-through puncture with 22-gauge needle outside of the blood vessels area. Then the cecum is retrieved back into the peritoneal cavity and the abdomen is sealed. Since the cecum is an endogenous source of bacteria, perforation of the cecum results in polymicrobial infection of the peritoneum, followed by translocation of enteric bacteria into the blood compartment. Bacteria release in the host periphery triggers systemic activation of the inflammatory response, subsequent septic shock, multiorgan dysfunction and death. Disease patterns with typical symptoms of human sepsis and septic shock, such as hypothermia, tachycardia and tachypnea, are also observed in mice.

In this example, 10-12 weeks old C57BL/6J mice underwent the cecal ligation puncture procedure. In order to test the protective effect of the Top1 inhibitor camptothecin (CPT), the mice were allowed to recover from surgery and anesthesia for 6 hours and then injected intravenously with CPT at the dose of 30 mg/kg of body weight. Animals were further injected intravenously with 30 mg/kg of CPT twice at day 2 post-surgery, and intraperitoneally (i.p.) with 60 mg/kg of the drug at day 3 post-surgery. n=4 individual mice per group.

As shown in FIG. 12, CPT treatment improved survival following CLP.

The Ebola Virus Infection Model in Mice

These studies were conducted in collaboration with Dr. Alexander Bukreyev (University of Texas Medical Branch & Galveston National Laboratory, Galveston, Tex.), which successfully established the mouse infection model with a murine adapted Ebola virus (EBOV) (Flyak, Shen et al. 2016; Rialdi, Campisi et al. 2016). Preliminary experiments were performed to test CPT treatment in mice that were intraperitoneally (i.p.) infected with $10^3$ plaque forming units (PFU) of the murine adapted EBOV. A dose of 30 mg/kg of CPT was given i.p. beginning on day 1 post-infection each day until day 4 post-infection (i.e., on day 1, day 2, day 3 and day 4 post-infection). As shown in FIG. 13, it was observed that animals that received the CPT treatment starting at day 1 post-viral inoculation had a one day delay to death relative to the control group and a survival rate of 20% (1 of 5 CPT-treated mice survived the EBOV infection, whereas none of the control mice survived).

The *Legionella pneumoniae* Infection Model in Guinea Pig

The guinea pig is a representative model of both human respiratory physiology (Canning and Chou 2008) and human Legionnaires' diseases (Edelstein 2013). *L. pneumophila* infection is known to induce pro-inflammatory cytokine expression and sepsis in the guinea pig model (Schmeck, Lorenz et al. 2008; Edelstein 2013), mimicking cytokine-driven syndromes such as Acute Respiratory Distress Syndrome (ARDS) and sepsis in humans. Additionally, the Hartley guinea pigs were used, which are outbred and thus more closely recapitulate the heterogeneous population of human patients.

Young female Hartley stock guinea pigs (4-5 weeks old) were infected intratracheally under anesthesia with a clinical isolate strain of *Legionella pneumophila* serogroup 1, isolated from a patient by the Mount Sinai Hospital clinical microbiology laboratory and designated *L. pneumophila* strain Mount Sinai 1. Each animal received $10^6$ colony-forming units (CFU) of *Legionella* in sterile water. Animals were injected intraperitoneally with 30 mg/kg of the compound CPT at 12 and 36 hours after infection and then with 60 mg/kg of the compound at 60 and 84 hours after infection. n=9 individuals guinea pigs per group.

As shown in FIG. 14, CPT treatment resulted in a delay of death relative to the control group and improved survival rates.

Sequence Listing

| SEQ ID NO | TYPE | SOURCE | SEQUENCE |
|---|---|---|---|
| 1 | DNA | Synthetic | 5'-ACCTTCTACAATGAGCTGCG-3' |
| 2 | | | 5'-CCTGGATAGCAACGTACATGG-3' |
| 3 | | | 5'-GCAAATTCCATGGCACCGT-3' |
| 4 | | | 5'-GCCCCACTTGATTTTGGAGG-3' |
| 5 | | | 5'-GTAACCCGTTGAACCCCATT-3' |
| 6 | | | 5'-CCATCCAATCGGTAGTAGCG-3' |
| 7 | | | 5'-AGGCTTTGCATGTCTTGG-3' |
| 8 | | | 5'GAGTCTTCATCTGCTTGTTGC-3' |
| 9 | | | 5'-TTCGGAGAAAGGCATTAGA |
| 10 | | | 5'-TCCAGGGCTTCATTCATAT |
| 11 | | | 5'-TCTGGCACAACAGGTAGTAGGC |
| 12 | | | 5'-GAGAAGCACAACAGGAGAGCAA |
| 13 | | | 5'-GAAAAGGACCCCACGAAGTGT |
| 14 | | | 5'-AGTCAAGGGCATATCCTACAACA |
| 15 | | | 5'-GAGCTACCCACAGAAGAAACC |
| 16 | | | 5'-GAGTCGATGCTTGAGTTGTGTT |
| 17 | | | 5'-ATGATGGCTTATTACAGTGGCAA |
| 18 | | | 5'-GTCGGAGATTCGTAGCTGGA |
| 19 | | | 5'-ACTCACCTCTTCAGAACGAATTG |
| 20 | | | 5'-CCATCTTTGGAAGGTTCAGGTTG |
| 21 | | | 5'-TTTTGCCAAGGAGTGCTAAAGA |
| 22 | | | 5'-AACCCTCTGCACCCAGTTTTC |
| 23 | | | 5'-ATGGCAAAGCAGTACGACTCG |
| 24 | | | 5'-GCAAGGCTGTAATGGGAAC |
| 25 | | | 5'-ACAACAAACGGTGGTATTTCACT |
| 26 | | | 5'-CCTGCTGGCGATAAGAAAGTT |
| 27 | | | 5'-TTACGGATGTCAACGTCACAGTTC |
| 28 | | | 5'-ACTATTGGCAACGAGCGGTTC |
| 29 | | | 5'-CGAGTACCAGTCCCTTTTCTGTTC |
| 30 | | | 5'-AAGACTTGGTTGCAGAGTGTCATG |
| 31 | | | 5'-TGAGATCTACTCGGCAAACCTAGTG |
| 32 | | | 5'-CTTCGTAGAGAACAACATAAGTCAGATACC |
| 33 | | | 5'-GCCTATCGCCAAGATTTAGATGA |
| 34 | | | 5'-TTCTGGATTTAACCGGACAGC |
| 35 | | | 5'-AGAACCAAAACGAGAGAGTGAGG |
| 36 | | | 5'-TCCAGACGGTAGTTCGCAATG |
| 37 | | | 5'-GTCCCTCAACGGAAGAACCAA |
| 38 | | | 5'-ACTCTCAGACAGCGAGGCACAT |
| 39 | | | 5'-TGCCCACGTCAAGGAGTATTTC |
| 40 | | | 5'-TCCTAGCTCATCTCCAAATAGTTGATG |
| 41 | | | 5'-GCAACTGTTCCTGAACTCAACT |
| 42 | | | 5'-ATCTTTTGGGGTCCGTCAACT |
| 43 | | | GAGGGGAGAGGGGTAAAA |
| 44 | | | AGCCATAAAAGGCAACTTTCG |
| 45 | | | AGAGGAGCCTGGCTAAGCA |
| 46 | | | GGTTGCTGTAAATTAGGCAGC |
| 47 | | | TGCACTGCAACCATGAGG |
| 48 | | | TGACTCAACAGCACTACCGA |
| 49 | | | CCCAATAAATATAGGACTGGAGATG |
| 50 | | | GAGTTCATAGCTGGGCTCCT |
| 51 | | | TATAAAAAGCCACCGGAGCA |
| 52 | | | GCCAGCTTGGAAGTCATGTT |
| 53 | | | GGGCTACAGTGGGTGAAAGG |
| 54 | | | GGGCTACAGTGGGTGAAAGG |
| 55 | | | TGAAAAGAGCACACCCCCTA |
| 56 | | | CTCCTCAGAAACCTGCCTTG |
| 57 | | | AGCCACACCCGACTAACG |
| 58 | | | CTTGGTGCTTTGAGGGATCT |
| 59 | | | AATGTGGGATTTTCCCATGA |
| 60 | | | GCGGTTTCTGGAATTGACTATC |
| 61 | | | GGGCTTTTCCAGACATCGT |
| 62 | | | TGAAGTGTGGCTGGAGTCTG |
| 63 | | | GATCGGAAGAGCACACGTCT |
| 64 | | | ACACTCTTTCCCTACACGACGCTCTTCCGAT C*T * = phosphorothioate |
| 65 | | | 5'AATGATACGGCGACCACCGAGATCTACAC TCTTTCCCTACACGACGCTCTTCCGAT C*T |
| 66 | | | 5'CAAGCAGAAGACGGCATACGAGAT [NNNNNN]GTGACTGGAGTTCAGACGTGTGC T CTTCCGATC*T |

REFERENCES

1. C. A. Janeway, Jr., R. Medzhitov, Innate immune recognition. *Annu Rev Immunol* 20, 197 (2002).
2. R. Medzhitov, Approaching the asymptote: 20 years later. *Immunity* 30, 766 (Jun. 19, 2009).
3. B. Beutler et al., Genetic analysis of resistance to viral infection. *Nat Rev Immunol* 7, 753 (October 2007).
4. J. W. Schoggins et al., A diverse range of gene products are effectors of the type I interferon antiviral response. *Nature* 472, 481 (Apr. 28, 2011).
5. Y. J. Crow, Type I interferonopathies: mendelian type I interferon up-regulation. *Curr Opin Immunol* 32, 7 (February 2015).
6. T. Hanada, A. Yoshimura, Regulation of cytokine signaling and inflammation. *Cytokine Growth Factor Rev* 13, 413 (August-October 2002).
7. F. McNab, K. Mayer-Barber, A. Sher, A. Wack, A. O'Garra, Type I interferons in infectious disease. *Nat Rev Immunol* 15, 87 (February 2015).
8. M. Brandes, F. Klauschen, S. Kuchen, R. N. Germain, A systems analysis identifies a feedforward inflammatory circuit leading to lethal influenza infection. *Cell* 154, 197 (Jul. 3, 2013).
9. Y. M. Loo, M. Gale, Jr., Influenza: fatal immunity and the 1918 virus. *Nature* 445, 267 (Jan. 18, 2007).
10. P. A. Ward, New approaches to the study of sepsis. *EMBO Mot Med* 4, 1234 (December 2012).
11. L. Strahle, D. Garcin, P. Le Mercier, J. F. Schlaak, D. Kolakofsky, Sendai virus targets inflammatory responses, as well as the interferon-induced antiviral state, in a multifaceted manner. *J Virol* 77, 7903 (July 2003).
12. G. L. Beretta, L. Gatti, P. Perego, N. Zaffaroni, Camptothecin resistance in cancer: insights into the molecular mechanisms of a DNA-damaging drug. *Curr Med Chem* 20, 1541 (2013).
13. Y. Chen et al., Cordycepin induces apoptosis of C6 glioma cells through the adenosine 2A receptor-p53-caspase-7-PARP pathway. *Chem Biol Interact* 216, 17 (Jun. 5, 2014).
14. S. Kubicek et al., Reversal of H3K9me2 by a small-molecule inhibitor for the G9a histone methyltransferase. *Mol Cell* 25, 473 (Feb. 9, 2007).
15. I. Kubo, T. J. Ha, K. Shimizu, Lipoxygenase inhibitory activity of 6-pentadecanylsalicylic acid without prooxidant effect. *Nat Prod Commun* 5, 85 (January 2010).
16. S. Menazza et al., Oxidative stress by monoamine oxidases is causally involved in myofiber damage in muscular dystrophy. *Hum Mol Genet* 19, 4207 (Nov. 1, 2010).
17. P. B. Rahl et al., c-Myc regulates transcriptional pause release. *Cell* 141, 432 (Apr. 30, 2010).
18. K. M. Regal, S. L. Mercer, J. E. Deweese, HU-331 is a catalytic inhibitor of topoisomerase II alpha. *Chem Res Toxicol* 27, 2044 (Dec. 15, 2014).
19. N. A. Smith, J. A. Byl, S. L. Mercer, J. E. Deweese, N. Osheroff, Etoposide quinone is a covalent poison of human topoisomerase IIbeta. *Biochemistry* 53, 3229 (May 20, 2014).
20. Q. Zhou, T. Li, D. H. Price, RNA polymerase II elongation control. *Annu Rev Biochem* 81, 119 (2012).
21. P. Filippakopoulos, S. Knapp, Targeting bromodomains: epigenetic readers of lysine acetylation. *Nat Rev Drug Discov* 13, 337 (May, 2014).
22. Y. Pommier, Topoisomerase I inhibitors: camptothecins and beyond. *Nat Rev Cancer* 6, 789 (October 2006).
23. E. Nicodeme et al., Suppression of inflammation by a synthetic histone mimic. *Nature* 468, 1119 (Dec. 23, 2010).
24. P. Filippakopoulos et al., Selective inhibition of BET bromodomains. *Nature* 468, 1067 (Dec. 23, 2010).
25. G. Egger, G. Liang, A. Aparicio, P. A. Jones, Epigenetics in human disease and prospects for epigenetic therapy. *Nature* 429, 457 (May 27, 2004).
26. I. F. King et al., Topoisomerases facilitate transcription of long genes linked to autism. *Nature* 501, 58 (Sep. 5, 2013).
27. S. Solier et al., Transcription poisoning by Topoisomerase I is controlled by gene length, splice sites, and miR-142-3p. *Cancer Res* 73, 4830 (Aug. 1, 2013).
28. F. Kouzine et al., Transcription-dependent dynamic supercoiling is a short-range genomic force. *Nat Struct Mol Biol* 20, 396 (March 2013).
29. M. Kretzschmar, M. Meisterernst, R. G. Roeder, Identification of human DNA topoisomerase I as a cofactor for activator-dependent transcription by RNA polymerase II. *Proc Natl Acad Sci USA* 90, 11508 (Dec. 15, 1993).
30. A. Merino, K. R. Madden, W. S. Lane, J. J. Champoux, D. Reinberg, DNA topoisomerase I is involved in both repression and activation of transcription. *Nature* 365, 227 (Sep. 16, 1993).
31. K. W. Kohn, Y. Pommier, Molecular and biological determinants of the cytotoxic actions of camptothecins. Perspective for the development of new topoisomerase I inhibitors. *Ann NY Acad Sci* 922, 11 (2000).
32. L. Anders et al., Genome-wide localization of small molecules. *Nat Biotechnol* 32, 92 (January 2014).
33. S. S. Teves, S. Henikoff, Transcription-generated torsional stress destabilizes nucleosomes. *Nat Struct Mot Blot* 21, 88 (January 2014).
34. S. Akira, S. Uematsu, O. Takeuchi, Pathogen recognition and innate immunity. *Cell* 124, 783 (Feb. 24, 2006).
35. G. Sass, K. Koerber, R. Bang, H. Guehring, G. Tiegs, Inducible nitric oxide synthase is critical for immune-mediated liver injury in mice. *J Clin Invest* 107, 439 (Febuary 2001).
36. M. Bray, S. Mahanty, Ebola hemorrhagic fever and septic shock. *J Infect Dis* 188, 1613 (Dec. 1, 2003).
37. L. Martinez-Gil et al., Identification of small molecules with type I interferon inducing properties by high-throughput screening. *PLoS One* 7, e49049 (2012).
38. A. Baum, R. Sachidanandam, A. Garcia-Sastre, Preference of RIG-I for short viral RNA molecules in infected cells revealed by next-generation sequencing. *Proc Natl Acad Sci USA* 107, 16303 (Sep. 14, 2010).
39. L. Martinez-Gil et al., A Sendai virus-derived RNA agonist of RIG-I as a virus vaccine adjuvant. *J Virol* 87, 1290 (Febuary 2013).
40. C. F. Basler et al., The Ebola virus VP35 protein functions as a type I IFN antagonist. *Proc Natl Acad Sci USA* 97, 12289 (Oct. 24, 2000).
41. W. Huang da, B. T. Sherman, R. A. Lempicki, Systematic and integrative analysis of large gene lists using DAVID bioinformatics resources. *Nat Protoc* 4, 44 (2009).
42. W. Huang da, B. T. Sherman, R. A. Lempicki, Bioinformatics enrichment tools: paths toward the comprehensive functional analysis of large gene lists. *Nucleic Acids Res* 37, 1 (January 2009).
43. T. I. Lee, S. E. Johnstone, R. A. Young, Chromatin immunoprecipitation and microarray-based analysis of protein location. *Nat Protoc* 1, 729 (2006).

44. M. S. Miller et al., Senataxin suppresses the antiviral transcriptional response and controls viral biogenesis. *Nat Immunol* 16, 485 (May, 2015).
45. B. L. Staker et al., The mechanism of topoisomerase I poisoning by a camptothecin analog. *Proc Natl Acad Sci USA* 99, 15387 (Nov. 26, 2002).
46. K. C. Swamy, N. N. Kumar, E. Balaraman, K. V. Kumar, Mitsunobu and related reactions: advances and applications. *Chem Rev* 109, 2551 (June 2009).
47. K. Hyz et al., Topotecan dynamics, tautomerism and reactivity—1H/13C NMR and ESI MS study. *Magn Reson Chem* 48, 575 (August 2010).
48. A. Dobin et al., STAR: ultrafast universal RNA-seq aligner. *Bioinformatics* 29, 15 (Jan. 1, 2013).
49. Y. Liao, G. K. Smyth, W. Shi, featureCounts: an efficient general purpose program for assigning sequence reads to genomic features. *Bioinformatics* 30, 923 (Apr. 1, 2014).
50. M. D. Robinson, D. J. McCarthy, G. K. Smyth, edgeR: a Bioconductor package for differential expression analysis of digital gene expression data. *Bioinformatics* 26, 139 (Jan. 1, 2010).

While several possible embodiments are disclosed above, embodiments of the present invention are not so limited. These exemplary embodiments are not intended to be exhaustive or to unnecessarily limit the scope of the invention, but instead were chosen and described in order to explain the principles of the present invention so that others skilled in the art may practice the invention. Indeed, various modifications of the invention in addition to those described herein will become apparent to those skilled in the art from the foregoing description. Such modifications are intended to fall within the scope of the appended claims. Further, the terminology employed herein is used for the purpose of describing exemplary embodiments only and the terminology is not intended to be limiting since the scope of the various embodiments of the present invention will be limited only by the appended claims and equivalents thereof. The scope of the invention is therefore indicated by the following claims, rather than the foregoing description and above-discussed embodiments, and all changes that come within the meaning and range of equivalents thereof are intended to be embraced therein.

What is claimed is:

1. A method for treating a disease, condition or state characterized by an exacerbated inflammatory immune response in a subject in need thereof, the method comprising: administering a therapeutically effective amount of at least one compound that inhibits topoisomerase I activity, wherein the at least one compound is selected from the group consisting of camptothecin, irinotecan, topotecan, and lamarellin D, and wherein the disease, condition or state to be treated is selected from sepsis, septic shock, acute liver failure, endotoxic shock.

2. A method of treating exacerbated inflammatory immune response in a subject in need thereof, the method comprising: administering a therapeutically effective amount of at least one compound that inhibits topoisomerase I activity, wherein the at least one compound is selected from the group consisting of camptothecin, irinotecan, topotecan, and lamarellin D, and wherein the exacerbated inflammatory immune response is caused by the microorganism selected from the group consisting of Ebola virus, and *Legionella pneumophila*.

3. The method of claim 2, wherein the method includes co-administration of at least one other therapeutic agent to aid in treating the disease, condition or state.

4. The method of claim 3, wherein the at least one co-administered therapeutic agent is selected from the group consisting of:

one or more antibiotics, anti-fungal drugs, anti-viral drugs, anti-parasitic drugs, or anti-protozoal drug.

5. A method for treating a disease, condition or state characterized by an exacerbated inflammatory immune response in a subject in need thereof, the method comprising: administering a therapeutically effective amount of at least one compound that inhibits topoisomerase I activity, wherein the at least one compound is selected from the group consisting of camptothecin, irinotecan, topotecan, and lamarellin D, and wherein the disease, condition or state to be treated, is selected from sepsis, septic shock, acute liver failure, endotoxic shock.

6. The method of claim 1, wherein the therapeutically effective amount of the at least one compound is less than the therapeutically effective amount for treating cancers and/or tumors.

7. The method of claim 1, wherein the therapeutically effective amount of the at least one compound is administered for a shorter period of time than the administration period of the therapeutically effective amount for treating cancers and/or tumors.

* * * * *